US008415322B2

(12) United States Patent
Clark

(10) Patent No.: US 8,415,322 B2
(45) Date of Patent: *Apr. 9, 2013

(54) MODIFIED FLUORINATED NUCLEOSIDE ANALOGUES

(75) Inventor: Jeremy Clark, Birmingham, AL (US)

(73) Assignee: Gilead Pharmasset LLC, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/878,262

(22) Filed: Sep. 9, 2010

(65) Prior Publication Data

US 2011/0038833 A1 Feb. 17, 2011

Related U.S. Application Data

(63) Continuation of application No. 12/240,342, filed on Sep. 29, 2008, now abandoned, which is a continuation of application No. 10/828,753, filed on Apr. 21, 2004, now Pat. No. 7,429,572.

(60) Provisional application No. 60/474,368, filed on May 30, 2003.

(51) Int. Cl.
*A01N 43/04* (2006.01)
*A61K 31/70* (2006.01)

(52) U.S. Cl. .................. 514/49; 514/50; 514/51

(58) Field of Classification Search .................. None
See application file for complete search history.

(56) References Cited

U.S. PATENT DOCUMENTS

| | | | |
|---|---|---|---|
| 3,798,209 A | 3/1974 | Witkowski |
| 4,814,477 A | 3/1989 | Wijnberg |
| 4,957,924 A | 9/1990 | Beauchamp |
| 5,026,687 A | 6/1991 | Yarchoan |
| 5,118,820 A | 6/1992 | Hertel |
| 5,149,794 A | 9/1992 | Yatvin |
| 5,157,027 A | 10/1992 | Biller |
| 5,194,654 A | 3/1993 | Hostetler |
| 5,223,263 A | 6/1993 | Hostetler |
| 5,256,641 A | 10/1993 | Yatvin |
| 5,372,808 A | 12/1994 | Blatt |
| 5,405,598 A | 4/1995 | Schinazi |
| 5,411,947 A | 5/1995 | Hostetler |
| 5,420,266 A | 5/1995 | Britton |
| 5,462,724 A | 10/1995 | Schinazi |
| 5,463,092 A | 10/1995 | Hostetler |
| 5,496,546 A | 3/1996 | Wang |
| 5,538,865 A | 7/1996 | Reyes |
| 5,543,389 A | 8/1996 | Yatvin |
| 5,543,390 A | 8/1996 | Yatvin |
| 5,543,391 A | 8/1996 | Yatvin |
| 5,554,728 A | 9/1996 | Basava |
| 5,610,054 A | 3/1997 | Draper |
| 5,633,358 A | 5/1997 | Gruetzke |
| 5,633,388 A | 5/1997 | Diana |
| 5,676,942 A | 10/1997 | Testa |
| 5,703,058 A | 12/1997 | Schinazi |
| 5,711,944 A | 1/1998 | Gilbert |
| 5,725,859 A | 3/1998 | Omer |
| 5,738,845 A | 4/1998 | Imakawa |
| 5,738,846 A | 4/1998 | Greenwald |
| 5,747,646 A | 5/1998 | Hakimi |
| 5,767,097 A | 6/1998 | Tam |
| 5,792,834 A | 8/1998 | Hakimi |
| 5,830,455 A | 11/1998 | Valtuena |
| 5,830,905 A | 11/1998 | Diana |
| 5,834,594 A | 11/1998 | Hakimi |
| 5,837,257 A | 11/1998 | Tsai |
| 5,846,964 A | 12/1998 | Ozeki |
| 5,849,696 A | 12/1998 | Chretien |
| 5,869,253 A | 2/1999 | Draper |
| 5,891,874 A | 4/1999 | Colacino |
| 5,905,070 A | 5/1999 | Schinazi |
| 5,908,621 A | 6/1999 | Glue |
| 5,922,757 A | 7/1999 | Chojkier |
| 5,928,636 A | 7/1999 | Alber |
| 5,942,223 A | 8/1999 | Bazer |
| 5,980,884 A | 11/1999 | Blatt |
| 5,990,276 A | 11/1999 | Zhang |
| 6,004,933 A | 12/1999 | Spruce |
| 6,034,134 A | 3/2000 | Gold |
| 6,043,077 A | 3/2000 | Barber |
| 6,056,961 A | 5/2000 | Lavie |
| 6,090,932 A | 7/2000 | McGee |
| 6,130,326 A | 10/2000 | Ramasamy |
| 6,156,501 A | 12/2000 | McGall |
| 6,232,300 B1 | 5/2001 | Schinazi |
| 6,239,159 B1 | 5/2001 | Brown |
| 6,348,587 B1 | 2/2002 | Schinazi |
| 6,372,883 B1 | 4/2002 | Attwood |
| 6,391,859 B1 | 5/2002 | Schinazi |
| 6,410,531 B1 | 6/2002 | Llinas-Brunet |
| 6,420,380 B2 | 7/2002 | Llinas-Brunet |
| 6,455,513 B1 | 9/2002 | McGuigan |
| 6,455,690 B1 | 9/2002 | Tam |
| 6,479,463 B1 | 11/2002 | Wang |
| 6,495,677 B1 | 12/2002 | Ramasamy |
| 6,509,320 B1 | 1/2003 | Wang |
| 6,534,523 B1 | 3/2003 | Llinas-Brunet |
| 6,552,183 B1 | 4/2003 | Ramasamy |
| 6,555,677 B2 | 4/2003 | Petrillo |
| 6,573,248 B2 | 6/2003 | Ramasamy |
| 6,642,206 B2 | 11/2003 | Ramasamy |

(Continued)

FOREIGN PATENT DOCUMENTS

DE 199 14 474 10/1989
EP 0 350 287 1/1990

(Continued)

OTHER PUBLICATIONS

Asif et aL., "Pharmacokinetics of the Antiviral Agent B-D-2'-Fluoro-2'-C-Methylcytidine in Rhesus Monkeys," Antimicrobial Agents and Chemotherapy, vol. 51, No. 8, 2877-2882, Aug. 2007.

(Continued)

*Primary Examiner* — Traviss C McIntosh, III
(74) *Attorney, Agent, or Firm* — Fitzpatrick, Cella, Harper & Scinto

(57) ABSTRACT

The disclosed invention provides compositions and methods of treating a Flaviviridae infection, including hepatitis C virus, West Nile Virus, yellow fever virus, and a rhinovirus infection in a host, including animals, and especially humans, using a (2'R)-2'-deoxy-2'-fluoro-2'-C-methyl nucleosides, or a pharmaceutically acceptable salt or prodrug thereof.

21 Claims, 4 Drawing Sheets

U.S. PATENT DOCUMENTS

| | | |
|---|---|---|
| 6,660,721 B2 | 12/2003 | Devos |
| 6,677,314 B2 | 1/2004 | Klecker |
| 6,677,315 B2 | 1/2004 | Klecker |
| 6,680,303 B2 | 1/2004 | Schinazi |
| 6,682,715 B2 | 1/2004 | Klecker |
| 6,683,045 B2 | 1/2004 | Klecker |
| 6,703,374 B1 | 3/2004 | Klecker |
| 6,753,309 B2 | 6/2004 | Klecker |
| 6,777,395 B2 | 8/2004 | Bhat |
| 6,787,305 B1 | 9/2004 | Li |
| 6,787,526 B1 | 9/2004 | Bryant |
| 6,815,542 B2 | 11/2004 | Hong |
| 6,897,201 B2 | 5/2005 | Boyer |
| 6,908,924 B2 | 6/2005 | Watanabe |
| 6,914,054 B2 | 7/2005 | Sommadossi |
| 6,962,991 B2 | 11/2005 | Dempcy |
| 7,018,985 B1 | 3/2006 | Boyer |
| 7,018,989 B2 | 3/2006 | McGuigan |
| 7,081,449 B2 | 7/2006 | Pietrzkowski |
| 7,105,499 B2 * | 9/2006 | Carroll et al. .................... 514/49 |
| 7,148,206 B2 | 12/2006 | Sommadossi |
| 7,163,929 B2 | 1/2007 | Sommadossi |
| 7,429,572 B2 * | 9/2008 | Clark ............................ 514/49 |
| 7,608,600 B2 * | 10/2009 | Storer et al. ................... 514/45 |
| 2002/0198173 A1 | 12/2002 | Schinazi |
| 2003/0060400 A1 | 3/2003 | LaColla Paulo |
| 2003/0120071 A1 | 6/2003 | McGuigan |
| 2003/0144502 A1 | 7/2003 | Pietrzkowski |
| 2003/0153744 A1 | 8/2003 | Mekouar |
| 2004/0006007 A1 | 1/2004 | Gosselin |
| 2004/0014108 A1 | 1/2004 | Elarup |
| 2004/0023901 A1 | 2/2004 | Cook |
| 2004/0059104 A1 | 3/2004 | Cook |
| 2004/0063622 A1 | 4/2004 | Sommadossi |
| 2004/0097461 A1 | 5/2004 | Sommadossi |
| 2004/0097462 A1 | 5/2004 | Sommadossi |
| 2004/0101535 A1 | 5/2004 | Sommadossi |
| 2004/0102414 A1 | 5/2004 | Sommadossi |
| 2004/0167140 A1 | 8/2004 | Schinazi |
| 2004/0191824 A1 | 9/2004 | Dempcy |
| 2004/0229839 A1 | 11/2004 | Babu |
| 2004/0248892 A1 | 12/2004 | Wang |
| 2004/0259934 A1 | 12/2004 | Olsen |
| 2004/0265969 A1 | 12/2004 | Li |
| 2004/0266996 A1 | 12/2004 | Rabi |
| 2005/0009737 A1 | 1/2005 | Clark |
| 2005/0026853 A1 | 2/2005 | Mekouar |
| 2005/0031588 A1 | 2/2005 | Sommadossi |
| 2005/0075309 A1 | 4/2005 | Storer |
| 2005/0080034 A1 | 4/2005 | Standring |
| 2005/0090660 A1 | 4/2005 | Watanabe |
| 2005/0124532 A1 | 6/2005 | Sommadossi |
| 2005/0130931 A1 | 6/2005 | Boyer |
| 2005/0137161 A1 | 6/2005 | Sommadossi |
| 2005/0148534 A1 | 7/2005 | Castellino |
| 2005/0164960 A1 | 7/2005 | Olsen |
| 2005/0215513 A1 | 9/2005 | Boojamra |
| 2005/0227947 A1 | 10/2005 | Chan |
| 2005/0261237 A1 | 11/2005 | Boojamra |
| 2006/0003951 A1 | 1/2006 | Mekouar |
| 2006/0014943 A1 | 1/2006 | Dempcy |
| 2006/0035866 A1 | 2/2006 | Cannizzaro |
| 2006/0040944 A1 | 2/2006 | Gosselin |
| 2006/0079478 A1 | 4/2006 | Boojamra |
| 2006/0110727 A9 | 5/2006 | McGall |
| 2006/0122146 A1 | 6/2006 | Chun |
| 2006/0122154 A1 | 6/2006 | Olsen |
| 2006/0142238 A1 | 6/2006 | McGuigan |
| 2006/0144502 A1 | 7/2006 | Weder |
| 2007/0015905 A1 | 1/2007 | LaColla |
| 2007/0037735 A1 | 2/2007 | Gosselin |
| 2007/0037773 A1 | 2/2007 | Sommadossi |
| 2007/0042939 A1 | 2/2007 | LaColla |
| 2007/0042990 A1 | 2/2007 | Gosselin |
| 2007/0060498 A1 | 3/2007 | Gosselin |
| 2007/0060541 A1 | 3/2007 | Gosselin |
| 2007/0087960 A1 | 4/2007 | Storer |
| 2007/0225249 A1 | 9/2007 | Shi |
| 2008/0253995 A1 | 10/2008 | Clark |

FOREIGN PATENT DOCUMENTS

| | | |
|---|---|---|
| EP | 0 180 276 | 5/1996 |
| WO | WO8902733 | 4/1989 |
| WO | WO9000555 | 1/1990 |
| WO | WO9116920 | 11/1991 |
| WO | WO9118914 | 12/1991 |
| WO | WO9119721 | 12/1991 |
| WO | WO9300910 | 1/1993 |
| WO | WO9426273 | 11/1994 |
| WO | WO9513090 | 5/1995 |
| WO | WO9524185 | 9/1995 |
| WO | WO9615132 | 5/1996 |
| WO | WO9632403 | 10/1996 |
| WO | WO9736654 | 10/1997 |
| WO | WO9816184 | 4/1998 |
| WO | WO9817679 | 4/1998 |
| WO | WO9822496 | 5/1998 |
| WO | WO9907734 | 2/1999 |
| WO | WO9915194 | 4/1999 |
| WO | WO9932139 | 7/1999 |
| WO | WO9932140 | 7/1999 |
| WO | WO9943691 | 9/1999 |
| WO | WO9959621 | 11/1999 |
| WO | WO9964016 | 12/1999 |
| WO | WO0009531 | 2/2000 |
| WO | WO0024355 | 5/2000 |
| WO | WO0037110 | 6/2000 |
| WO | WO0132153 | 5/2001 |
| WO | WO0160315 | 8/2001 |
| WO | WO0179246 | 10/2001 |
| WO | WO0181359 | 11/2001 |
| WO | WO0190121 | 11/2001 |
| WO | WO0191737 | 12/2001 |
| WO | WO0192282 | 12/2001 |
| WO | WO0196353 | 12/2001 |
| WO | WO0208187 | 1/2002 |
| WO | WO0208198 | 1/2002 |
| WO | WO0208251 | 1/2002 |
| WO | WO0208256 | 1/2002 |
| WO | WO0218404 | 3/2002 |
| WO | WO0232414 | 4/2002 |
| WO | WO0232920 | 4/2002 |
| WO | WO0242172 | 6/2002 |
| WO | WO0248116 | 6/2002 |
| WO | WO0248157 | 6/2002 |
| WO | WO0248165 | 6/2002 |
| WO | WO0248172 | 6/2002 |
| WO | WO0249165 | 6/2002 |
| WO | WO02048157 | 6/2002 |
| WO | WO02057287 | 7/2002 |
| WO | WO02057425 | 7/2002 |
| WO | WO02060926 | 8/2002 |
| WO | WO02100415 | 12/2002 |
| WO | WO03024461 | 3/2003 |
| WO | WO03051899 | 6/2003 |
| WO | WO03053989 | 7/2003 |
| WO | WO03061576 | 7/2003 |
| WO | WO03062256 | 7/2003 |
| WO | WO03068244 | 8/2003 |
| WO | WO03105770 | 12/2003 |
| WO | WO03106477 | 12/2003 |
| WO | WO04000858 | 12/2003 |
| WO | WO2004002422 | 1/2004 |
| WO | WO02004002999 | 1/2004 |
| WO | WO2004002999 | 1/2004 |
| WO | WO2004003000 | 1/2004 |
| WO | WO2004003138 | 1/2004 |
| WO | WO2004007512 | 1/2004 |
| WO | WO2004009020 | 1/2004 |
| WO | WO2004009610 | 1/2004 |
| WO | WO2004011478 | 2/2004 |
| WO | WO2004080466 | 9/2004 |
| WO | WO2004096234 | 11/2004 |
| WO | WO2004096235 | 11/2004 |
| WO | WO2004096286 | 11/2004 |
| WO | WO2004106356 | 12/2004 |
| WO | WO2005002626 | 1/2005 |

| | | |
|---|---|---|
| WO | WO2005003147 | 1/2005 |
| WO | WO2005007810 | 1/2005 |
| WO | WO2005008877 | 1/2005 |
| WO | WO2005009418 | 2/2005 |
| WO | WO02005012327 | 2/2005 |
| WO | WO2005020884 | 3/2005 |
| WO | WO2005021568 | 6/2005 |
| WO | WO2005072361 | 8/2005 |
| WO | WO2005087788 | 9/2005 |
| WO | WO2006000922 | 1/2006 |
| WO | WO2006012440 | 2/2006 |
| WO | WO2006029081 | 3/2006 |
| WO | WO2006031725 | 3/2006 |
| WO | WO2006037028 | 4/2006 |
| WO | WO2006061576 | 6/2006 |
| WO | WO2006065335 | 6/2006 |

OTHER PUBLICATIONS

Banker, et al., "Modern Pharmaceutics, 3 ed," Marcel Dekker, New York, 451, 596 (1996).

Battaglia, A. et al., "Combination Therapy with Interferon and Ribavirin in the Treatment of Chronic Hepatitis C Infection," The Annals of Pharmacotherapy, vol. 34, No. 4, pp. 487-494 Apr. 2000).

Bhat, B. et al., "Synthesis and Pharmacokinetic Properties of Nucleoside Analogues as Possible Inhibitors of HCV 3 RNA Replication," (Oral Session V: Hepatitis C Virus, Flaviviruses), 16th International Conference on Antiviral Research, Abstract No. 120, p. A15 (Apr. 27-May 1, 2003, Savannah, GA).

Berenguer, M. et al., "Hepatitis C Virus in the Transplant Setting," Antiviral Therapy. Second International Conference on Therapies for Viral Hepatitis, vol. 3, Supplement 3, pp. 125-136 (1998).

Chu, M. et al., "Isolation and structure of Sch 351633: A novel hepatitis C virus (HCV) NS3 protease inhibitor from the fungus *Penicillium griseofulvum*," Bioorganic a. Medicinal Chemistry Letters, vol. 9, pp. 1949-1952 (1999).

Chu, M. et al., "Structure of Sch 68631:L A New Hepatitis C Virus Proteinase Inhibitor from *Streptomyces* sp.," Tetrahedron Letters, vol. 37, No. 40, pp. 7229-7232 (1996).

Clark, J. et al., "Design, Synthesis and Antiviral Activity of 2'-Deoxy-2'-fluoro-2'-C-methylcytidine, a Potent Inhibitor of Hepatitis C Virus Replication," Journal of Medicinal Chemistry, vol. 48, No. 17, pp. 5504-5508 (2005).

Davis, G.L., "Current Therapy for Chronic Hepatitis C," Gastroenterology 118: 8104-S114 (2000).

De Lombaert, S. et al., "N-Phosphonomethyl Dipeptides and their Phosphonate Prod rugs, a New Generation of Neutral Endopeptidase (NEP, EO 3.4.24.11) Inhibitors," J. Med. Chem., vol. 37, No. 4, pp. 498-511 (1994).

Edmundson et al., "Cyclic Organophosphorus Compounds Part 23. Configurational Assignments in the 4-Phenyl-1,3,2λ5—dioxaphosphorinane Series. X-Ray Molecular Structure of cls-2-Benzylamino-4-phenylk-1 ,3,2-dioxaphosphorinane 2-Oxide," J. Chem. Res. Synop., 1989, 5:122.

Eldrup, A. et al., "Structure Activity Relationship of 2' Modified Nucleosides for Inhibition of Hepatitis C Virus," (Oral 10 Session V: Hepatitis C Virus, Flaviviruses), 16th International Conference on Antiviral Research, Abstract No. 119. p. A75 (Apr. 27-May 1, 2003, Savannah, GA).

Eldrup, A. et al., "Structure-Activity Relationship of Purine Ribonucleosides for Inhibition of Hepatitis C Virus RNA-Dependent RNA Polymerase," J. Med. Chem., VQI. 47, No. 9, pp. 2283-2296 (2004).

Farquhar, D. et al., "Synthesis and Biological Evaluation of Neutral Derivatives of 5-Fluoro-2'-deoxyuridlne 5'-Phosphate," J. Med. Chem., vol. 26, No. 8, pp. 1153-1158 (Aug. 1983).

Farquhar, D. et al., "Synthesis of Biological Evaluation of 9-[5'-(2-0xo-1 ,3,2-oxazaphosphorinan-2-yl)-3-D-arabinosyl] adenine and 9-r5'(2-0xo-1.3,2-dioxaphosphorinan-2-yl)-β-D-arabinosyl] adenine; Potential Neutral Precursors of 9-[β-D-Arabinofuranosyl] adenine 5'-Monophosphate," J. Med. Chem., vol. 28, No. 9, pp. 1358-1361 (Sep. 1985).

Freed, J. et al., "Evidence for acyloxymethyl esters of pyrimidine 5'-deoxyribonucleotides as extracellular sources of active 5'-deoxyribonucleotides in cultured cells," Biochemical Pharmacology, vol. 38, No. 19, pp. 3193-3198 (Oct. 1, 1989).

Hertel et al., "Synthesis of 2-Deoxy-2,2-difluoro-D-ribose and 2-Deoxy-2,2-difluoro-D-rlbofurnosyl Nucleosides," J. Org. Chem., vol. 53, pp. 2406-2409 (1988).

Hostetler, K. et al., "Greatly Enhanced Inhibition of Human Immunodeficiency Virus Type 1 Replication in CEM and 16 HT-4-6C Cells by7 3'-Deoxythymidine Diphosphate Dimyristoylglygerol, a Lipid Pro drug of 3'-Deoxythymidine," Antimicrob. Agents Chemother., vol. 36, No. 9, pp. 2025-2029 (Sep. 1992).

Hostetler, K. et al., "Synthesis and Antiretro-viral Activity of Phospholipid Analogs of Azidothymidine and Other Antiviral Nucleosides," J. Biol. Chem., vol. 265, No. 11, pp. 6112-6117 (Apr. 16, 1990).

Hunston, R. et al., "Synthesis and Biological Properties of Some Cyclic Phoshotriesters Derived from 2'-Deoxy-6 fluorouridine," J. Med. Chem vol. 27, No. 4, pp. 440-444 (Apr. 1984).

Jones, R. et al., "Minireview: Nucleotide prodrugs," Antiviral Research, vol. 27, pp. 1-17 (1995).

Khannei, S. et al., "Neighboring Group Catalysis in the Design of Nucleotide Prodrugs," J. Med. Chem., vol. 39, No. 20, pp. 4109-4116 (1996).

Kotra, L.P., "Structure-Activity Relationships of 2'-Deoxy-2',2'-dlfluoro-L-erythro-pentofuraNosyl Nucleosides," J. Med. Chem vol. 40, pp. 3635-3644 (1997).

Kryuchkov, A et al., "Influence of Solvent on the Strength of Cyclic Oxygen-Containing Phosphorus Acids," Bulletin of the Academy of Sciences of the USSR, Division of Chemical Science, vol. 36, No. 6, Part 1, pp. 1145-1148 (1987).

Kucera, L. et al., "Novel Membrane-Interactive Ether Lipid Analogs that Inhibit Infectious HIV-1 Production and Induce Defective Virus Formation," AIDS Research and Human Retroviruses, vol. 6, No. 4, pp. 491-501 (Apr. 1990).

Li et al., "Synthesis of the Phosphoramidite Derivative of 2'-Deoxy-2'-C-β-methylcytidine," 68 J. Org. Chem., 6799-6802 (2003).

Ma et al., "Characterization of the Metabolic Activation of Hepatitis C Virus Nucleoside Inhibitor β-D-2'-Deoxy-2-fluoro-2'-C-methylcytidine (PSI-6130) and Identification of a Novel Active 5'-Triphosphate Species," 282 J. Biol. Chem., 29812-29820 (Oct. 2007).

Meier, C. et al., "Cyclic Saligenyl Phosphotriesters of 2',3'-Dldeoxy-2',3'-didehydrothymidlne (d4T)—A New Pro-Nuoleotide Approach;" Bioorganic & Medicinal Chemistry Letters, vol. 7, No. 2, pp. 99-104 (1997).

Mitchell, A et al., "Bioreversible Protection for the Phospho Group: Bloactivation of the Di(4-acyloxybenzyl) and Mono (4-acyloxybenzyl) Phosphoesters of Methylphosphonate and Phosphonoacetate," Journal of the Chemical Society, Perkin Transactions 1, No. 18, pp. 2345-2353 (Sep. 21, 1992).

Murakami et al., "Mechanism of Activation of β-D-2'-Deoxy-2'-C-Methylcytidine and Inhibition of Hepatitis C Virus NS5B RNA Polymerase," Antimicrobial Agents and Chemotherapy, vol. 51, No. 2, 503-509 (2007).

Neidleln, R. et al., "Mild preparation of 1-benzyloxyminoalkylphosphonio dichlorides: Application to the synthesis of cyclic phosphonic diesters and cyclic monoester amides," Heterecycles, vol. 35, No. 2, pp. 1185-1203 (1993).

Nifantyev, E. et al., "Synthesis and structure of some stable phospholane-phospholanes," Phosphorus, Sulfur and Silicon and the Related Elements, vol. 113, pp. 1-13 (1996).

Olsen, D. et al "2'-Modified Nucleoside Analogs as Inhibitors of Hepatitis C RNA Replication." (Oral Session V: Hepatitis C Virus, Flaviviruses), 16th International Conference on Antiviral Research, Abstract No. 121, p. A76 (Apr. 27-May 1, 2003, Savannah, GA).

Otto, "Evaluation of nucleoside analogs in the Hepatitis C virus replicon system," Framing the Knowledge of Therapeutics for Viral Hepatitis, Ed. by R. Schinazi and ER Schiff, 247-261 (2006).

Piantadosi, C. at al., "(Synthesis and Evaluation of Novel Ether lipid Nucleoside Conjugates for Anti-HIV-1 Activity," J. Med. Chem., vol. 34, No. 4, pp. 1406-1414 (1991).

Shih, Y. et al., "Preparation and Structures of 2-Dimethylamino-4-phenyl-1,3,2-dloxaphosphofinane-2-oxides," Bull. Inst. Chem. Academia Sinioa, No. 41, pp. 9-16 (Mar. 1994).

Starrett, Jr., J. et al .. "Synthesis, Oral Bioavailability Determination, and in Vitro Evaluation of Prodrugs of the Antiviral Agent 9-[2,(Phosphonomethoxy)ethyl]adenine (PMEA)," J. Med. Chem., vol. 37, No. 12, pp. 1857-1864 (1994).

Stuyver, L. et al., "Dynamics of Subgenomic Hepatitis C Virus Replicon RNA Levels in Huh-7 Cells after Exposure to Nucleoside Antimetabolites," Journal of Virology, vol. 77, No. 19, pp. 10689-10694 (Oct. 2003).

Stuyver, L. et al., "Ribonucleoside Analogue that Blocks Replication of Bovine Viral Diarrhea and Hepatitis C Virus in Culture," Antimicrob. Agents Chemother., vol. 47, No. 1, pp. 244-254 (Jan. 2003).

Stuyver, L. et al., "Inhibition of the Subgenomic Hepatitis C Virus Replicon in Huh-7 Cells by 2'-Deoxy-2'-fluorocytidine," Antimicrob. Agents Chemother., vol. 48, No. 2, pp. 661-654 (Feb. 2004).

Wolff, M., "Burger's Medicinal Chemistry, 5th ed., Part I," John Wiley & Sons. 975-977 (1995).

Zon, G., "4 Cyclophosphamide Analogues," Progress in Medicinal Chemistry, vol. 19, pp. 205-246 (1982).

European Search Report for application No. EP 11 15 7832 dated Jun. 8, 2011.

European Search Report for application No. EP 11 15 7939 dated Jun. 8, 2011.

European Search Report for application No. EP 11 15 7942 dated Jun. 8, 2011.

European Search Report for application No. EP 11 15 7954 dated Jun. 8, 2011.

* cited by examiner

MODIFIED FLUORINATED NUCLEOSIDE ANALOGUES

CROSS-REFERENCE TO RELATED PATENT APPLICATION

This application is a continuation of U.S. patent application Ser. No. 12/240,342, filed Sep. 29, 2008, which is a continuation of U.S. patent application Ser. No. 10/828,753, filed Apr. 21, 2004, which issued on Sep. 30, 2008 as U.S. Pat. No. 7,429,572, which claims priority to U.S. Provisional Application No. 60/474,368, filed May 30, 2003 and which are assigned to the same assignee as this application. The aforementioned patent applications are expressly incorporated herein by reference.

FIELD OF THE INVENTION

The present invention includes (2'R)-2'-deoxy-2'-fluoro-2'-C-methyl nucleosides having the natural β-D configuration and methods for the treatment of Flaviviridae infections, especially hepatitis C virus (HCV).

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-α alone or in combination with the nucleoside analog ribavirin, are of limited clinical benefit as resistance develops rapidly. Moreover, there is no established vaccine for HCV. Consequently, there is an urgent need for improved therapeutic agents that effectively combat chronic HCV infection.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. Therefore, NS5B polymerase is considered to be an essential component in the HCV replication complex (K. Ishi, et al., "Expression of Hepatitis C Virus NS5B Protein: Characterization of Its RNA Polymerase Activity and RNA Binding," *Heptology*, 29: 1227-1235 (1999); V. Lohmann, et al., "Biochemical and Kinetic Analysis of NS5B RNA-Dependent RNA Polymerase of the Hepatitis C Virus," *Virology*, 249: 108-118 (1998)). Inhibition of HCV NS5B polymerase prevents formation of the double-stranded HCV RNA and therefore constitutes an attractive approach to the development of HCV-specific antiviral therapies.

HCV belongs to a much larger family of viruses that share many common features.

Flaviviridae Viruses

The Flaviviridae family of viruses comprises at least three distinct genera: pestiviruses, which cause disease in cattle and pigs; flavivruses, which are the primary cause of diseases such as dengue fever and yellow fever; and hepaciviruses, whose sole member is HCV. The flavivirus genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the Dengue Hemorrhagic Fever viruses (DHF), yellow fever virus, shock syndrome and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med*, 1988, 319, 641-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res*. 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H. J., Advances in Virus Research, 1996, 47, 53-118; Moennig V., et al, Adv. Vir. Res. 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are at least 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al. (1988) *Nature* 333:22; Bazan and Fletterick (1989) *Virology* 171: 637-639; Gorbalenya et al. (1989) *Nucleic Acid Res.* 17.3889-3897). Similarly, the NS5B proteins of pestiviruses and hepaciviruses have the motifs characteristic of RNA-directed RNA polymerases (Koonin, E. V. and Dolja, V. V. (1993) *Crit. Rev. Biochem. Molec. Biol.* 28:375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett (1991) *Virology* 184:341-350; Bartenschlager et al. (1993) *J. Virol.* 67:3835-3844; Eckart et al. (1993) *Biochem. Biophys. Res. Comm.* 192:399-406; Grakoui et al. (1993) *J. Virol.* 67:2832-2843; Grakoui et al. (1993) *Proc. Natl. Acad. Sci. USA* 90:10583-10587; Hijikata et al. (1993) *J. Virol.* 67:4665-4675; Tome et al. (1993) *J. Virol.* 67:4017-4026). The NS4A protein, in both cases, acts as a cofactor with the NS3 serine protease (Bartenschlager et al. (1994) *J. Virol.* 68:5045-5055; Failla et al. (1994) *J. Virol.* 68: 3753-3760; Xu et al. (1997) *J. Virol.* 71:5312-5322). The NS3 protein of both viruses also functions as a helicase (Kim et al. (1995) *Biochem. Biophys. Res. Comm.* 215: 160-166; Jin and Peterson (1995) *Arch. Biochem. Biophys.,* 323:47-53; Warrener and Collett (1995) *J. Virol.* 69:1720-1726). Finally, the NS5B proteins of pestiviruses and hepaciviruses have the predicted RNA-directed RNA polymerases activity (Behrens et al. (1996) *EMBO.* 15:12-22; Lechmann et al. (1997) *J. Virol.* 71:8416-8428; Yuan et al. (1997) *Biochem. Biophys. Res. Comm.* 232:231-235; Hagedorn, PCT WO 97/12033; Zhong et al. (1998) *J. Virol.* 72.9365-9369).

Treatment of HCV Infection with Interferon

Interferons (IFNs) have been commercially available for the treatment of chronic hepatitis for nearly a decade. IFNs are glycoproteins produced by immune cells in response to viral infection. IFNs inhibit replication of a number of viruses, including HCV, and when used as the sole treatment for hepatitis C infection, IFN can in certain cases suppress serum HCV-RNA to undetectable levels. Additionally, IFN can normalize serum amino transferase levels. Unfortunately, the effect of IFN is temporary and a sustained response occurs in only 8%-9% of patients chronically infected with HCV (Gary L. Davis. Gastroenterology 18:S104-S114, 2000). Most patients, however, have difficulty tolerating interferon treatment, which causes severe flu-like symptoms, weight loss, and lack of energy and stamina.

A number of patents disclose Flaviviridae, including HCV, and treatments using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696. A number of patents also disclose pegylated forms of interferon, such as U.S. Pat. Nos. 5,747,646, 5,792,834 and 5,834,594 to Hoffmann-La Roche; PCT Publication No. WO 99/32139 and WO 99/32140 to Enzon; WO 95/13090 and U.S. Pat. Nos. 5,738,846 and 5,711,944 to Schering; and U.S. Pat. No. 5,908,621 to Glue et al.

Interferon alpha-2a and interferon alpha-2b are currently approved as monotherapy for the treatment of HCV. ROFERON®-A (Roche) is the recombinant form of interferon alpha-2a. PEGASYS® (Roche) is the pegylated (i.e. polyethylene glycol modified) form of interferon alpha-2a. INTRON®A (Schering Corporation) is the recombinant form of Interferon alpha-2b, and PEG-INTRON® (Schering Corporation) is the pegylated form of interferon alpha-2b.

Other forms of interferon alpha, as well as interferon beta, gamma, tau and omega are currently in clinical development for the treatment of HCV. For example, INFERGEN (interferon alphacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, and interferon gamma, interferon tau, and interferon gamma-1b by InterMune are in development.

Ribavirin

Ribavirin (1-β-D-ribofuranosyl-1-1,2,4-triazole-3-carboxamide) is a synthetic, non-interferon-inducing, broad spectrum antiviral nucleoside analog sold under the trade name, Virazole (The Merck Index, 11th edition, Editor: Budavari, S., Merck & Co., Inc., Rahway, N.J., p1304, 1989). U.S. Pat. No. 3,798,209 and RE29,835 disclose and claim ribavirin. Ribavirin is structurally similar to guanosine, and has in vitro activity against several DNA and RNA viruses including Flaviviridae (Gary L. Davis. *Gastroenterology* 118: 5104-5114, 2000).

Ribavirin reduces serum amino transferase levels to normal in 40% of patients, but it does not lower serum levels of HCV-RNA (Gary L. Davis, 2000). Thus, ribavirin alone is not effective in reducing viral RNA levels. Additionally, ribavirin has significant toxicity and is known to induce anemia. Ribavirin is not approved for monotherapy against HCV. It has been approved in combination with interferon alpha-2a or interferon alpha-2b for the treatment of HCV.

Ribavirin is a known inosine monophosphate dehydrogenease inhibitor that does not have specific anti-HCV activity in the HCV replicon system (Stuyver et al. *Journal of Virology,* 2003, 77, 10689-10694).

Combination of Interferon and Ribavirin

The current standard of care for chronic hepatitis C is combination therapy with an alpha interferon and ribavirin. The combination of interferon and ribavirin for the treatment of HCV infection has been reported to be effective in the treatment of interferon naïve patients (Battaglia, A. M. et al., *Ann. Pharmacother.* 34:487-494, 2000), as well as for treatment of patients when histological disease is present (Berenguer, M. et al. *Antivir. Ther.* 3(Suppl. 3):125-136, 1998). Studies have shown that more patients with hepatitis C respond to pegylated interferon-alpha/ribavirin combination therapy than to combination therapy with unpegylated interferon alpha. However, as with monotherapy, significant side effects develop during combination therapy, including hemolysis, flu-like symptoms, anemia, and fatigue. (Gary L. Davis, 2000). Combination therapy with PEG-INTRON® (peginterferon alpha-2b) and REBETOL® (Ribavirin, USP) capsules are available from Schering Corporation. REBETOL® (Schering Corporation) has also been approved in combination with INTRON® A (Interferon alpha-2b, recombinant, Schering Corporation). Roche's PEGASYS® (pegylated interferon alpha-2a) and COPEGUS® (ribavirin), as well as Three River Pharmacetical's Ribosphere® are also approved for the treatment of HCV.

PCT Publication Nos. WO 99/59621, WO 00/37110, WO 01/81359, WO 02/32414 and WO 03/024461 by Schering Corporation disclose the use of pegylated interferon alpha and ribavirin combination therapy for the treatment of HCV. PCT Publication Nos. WO 99/15194, WO 99/64016, and WO 00/24355 by Hoffmann-La Roche Inc. also disclose the use of pegylated interferon alpha and ribavirin combination therapy for the treatment of HCV.

Additional Methods to Treat Flaviviridae Infections

The development of new antiviral agents for Flaviviridae infections, especially hepatitis C, is currently underway. Specific inhibitors of HCV-derived enzymes such as protease, helicase, and polymerase inhibitors are being developed. Drugs that inhibit other steps in HCV replication are also in development, for example, drugs that block production of HCV antigens from the RNA (IRES inhibitors), drugs that prevent the normal processing of HCV proteins (inhibitors of glycosylation), drugs that block entry of HCV into cells (by blocking its receptor) and nonspecific cytoprotective agents that block cell injury caused by the virus infection. Further, molecular approaches are also being developed to treat hepatitis C, for example, ribozymes, which are enzymes that break down specific viral RNA molecules, antisense oligonucleotides, which are small complementary segments of DNA that bind to viral RNA and inhibit viral replication, and RNA interference techniques are under investigation (Bymock et al. *Antiviral Chemistry & Chemotherapy*, 11:2; 79-95 (2000); De Francesco et al. in *Antiviral Research*, 58: 1-16 (2003); and Kronke et al., *J. Virol.*, 78:3436-3446 (2004).

Bovine viral diarrhea virus (BVDV) is a pestivirus belonging to the family Flaviviridae and has been used as a surrogate for in vitro testing of potential antiviral agents. While activity against BVDV may suggest activity against other flaviviruses, often a compound can be inactive against BVDV and active against another flavivirus. Sommadossi and La Colla have revealed ("Methods and compositions for treating flaviviruses and pestiviruses", PCT WO 01/92282) that ribonucleosides containing a methyl group at the 2' "up" position have activity against BVDV. However, it is unclear whether these compounds can inhibit other flaviviruses, including HCV in cell culture or at the HCV NS5B level. Interestingly while this publication discloses a large number of compounds that are 2'-methyl-2'-X-ribonucleosides, where X is a halogen, fluorine is not considered. Furthermore, a synthetic pathway leading to nucleosides halogenated at the 2' "down" position is not shown by these inventors.

Dengue virus (DENV) is the causative agent of Dengue hemorrhagic fever (DHF). According to the World Health Organization (WHO), two fifths of the world population are now at risk for infection with this virus. An estimated 500,000 cases of DHF require hospitalization each year with a mortality rate of 5% in children.

West Nile virus (WNV), a flavivirus previously known to exist only in intertropical regions, has emerged in recent years in temperate areas of Europe and North America, presenting a threat to public health. The most serious manifestation of WNV infection is fatal encephalitis in humans. Outbreaks in New York City and sporadic occurrences in the Southern United States have been reported since 1999.

There is currently no preventive treatment of HCV, Dengue virus (DENV) or West Nile virus infection. Currently approved therapies, which exist only against HCV, are limited. Examples of antiviral agents that have been identified as active against the hepatitis C virus include:

Protease Inhibitors:

Substrate-based NS3 protease inhibitors (Attwood et al., PCT WO 98/22496, 1998; Attwood et al., *Antiviral Chemistry and Chemotherapy* 1999, 10, 259-273; Attwood et al., Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734) are being investigated.

Non-substrate-based NS3 protease inhibitors such as 2,4, 6-trihydroxy-3-nitro-benzamide derivatives (Sudo K. et al., *Biochemical and Biophysical Research Communications*, 1997, 238, 643-647; Sudo K. et al. *Antiviral Chemistry and Chemotherapy*, 1998, 9, 186), including RD3-4082 and RD3-4078, the former substituted on the amide with a 14 carbon chain and the latter processing a para-phenoxyphenyl group are also being investigated.

SCH 68631, a phenanthrenequinone, is an HCV protease inhibitor (Chu M. et al., Tetrahedron Letters 3 7:7229-7232, 1996). In another example by the same authors, SCH 351633, isolated from the fungus *Penicillium griseofulvum*, was identified as a protease inhibitor (Chu M. et al., *Bioorganic and Medicinal Chemistry Letters* 9:1949-1952). Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, α-chymotrypsin, chymase and subtilisin (Qasim M. A. et al., *Biochemistry* 36:1598-1607, 1997).

Several U.S. patents disclose protease inhibitors for the treatment of HCV. For example, U.S. Pat. No. 6,004,933 to Spruce et al. discloses a class of cysteine protease inhibitors for inhibiting HCV endopeptidase 2. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al. Peptides as NS3 serine protease inhibitors of HCV are disclosed in WO 02/008251 to Corvas International, Inc. and WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 to Schering Corporation. Imidazoleidinones as NS3 serine protease inhibitors of HCV are disclosed in WO 02/08198 to Schering Corporation and WO 02/48157 to Bristol Myers Squibb. WO 98/17679 to Vertex Pharmaceuticals and WO 02/48116 to Bristol Myers Squibb also disclose HCV protease inhibitors.

Thiazolidine derivatives which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193;

Thiazolidines and benzanilides identified in Kakiuchi N. et al. *J. EBS Letters* 421, 217-220; Takeshita N. et al. *Analytical Biochemistry*, 1997, 247, 242-246;

A phenanthrenequinone possessing activity against protease in a SDS-PAGE and autoradiography assay isolated from the fermentation culture broth of *Streptomyces* sp., Sch 68631 (Chu M. et al., *Tetrahedron Letters*, 1996, 37, 7229-7232), and Sch 351633, isolated from the fungus *Penicillium griseofulvum*, which demonstrates activity in a scintillation proximity assay (Chu M. et al., *Bioorganic and Medicinal Chemistry Letters* 9, 1949-1952);

Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

Nucleotide polymerase inhibitors and gliotoxin (Ferrari R. et al. *Journal of Virology*, 1999, 73, 1649-1654), and the natural product cerulenin (Lohmann V. et al, *Virology*, 1998, 249, 108-118);

Antisense phosphorothioate oligodeoxynucleotides (S-ODN) complementary to sequence stretches in the 5' noncoding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257);

Inhibitors of IRES-dependent translation (Ikeda N. et al., Agent for the prevention and treatment of hepatitis C, Japanese Patent Pub. JP-8268890; Kai Y. et al. Prevention and treatment of viral diseases, Japanese Patent Pub. JP-101 01591);

Ribozymes, such as nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.;

Nucleoside analogs have also been developed for the treatment of Flaviviridae infections.

Idenix Pharmaceuticals discloses the use of certain branched nucleosides in the treatment of flaviviruses (including HCV) and pestiviruses in International Publication Nos. WO 01/90121 and WO 01/92282. Specifically, a method for the treatment of hepatitis C virus infection (and flaviviruses and pestiviruses) in humans and other host animals is disclosed in the Idenix publications that includes administering an effective amount of a biologically active 1',2',3' or 4'-branched β-D or β-L nucleosides or a pharmaceutically acceptable salt or derivative thereof, administered either alone or in combination with another antiviral agent, optionally in a pharmaceutically acceptable carrier.

WO 2004/002422 to Idenix published Jan. 8, 2004 discloses a family of 2'-methyl nucleosides for the treatment of flavivirus infections. WO 2004/002999 to Idenix, published Jan. 8, 2004 discloses a series of 2' or 3' prodrugs of 1',2',3', or 4' branch nucleosides for the treatement of flavivirus infections including HCV infections.

Other patent applications disclosing the use of certain nucleoside analogs to treat hepatitis C virus infection include: PCT/CAOO/01316 (WO 01/32153; filed Nov. 3, 2000) and PCT/CAOI/00197 (WO 01/60315; filed Feb. 19, 2001) filed by BioChem Pharma, Inc. (now Shire Biochem, Inc.); PCT/USO2/01531 (WO 02/057425; filed Jan. 18, 2002) and PCT/U502/03086 (WO 02/057287; filed Jan. 18, 2002) filed by Merck & Co., Inc., PCT/EPOT/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48 165 by Pharmasset, Ltd.

WO 2004/007512 to Merck & Co. discloses a number of nucleoside compounds disclosed as inhibitors of RNA-dependent RNA viral polymerase. The nucleosides disclosed in this publication are primarily 2'-methyl-2'-hydroxy substituted nucleosides. WO 02/057287 to Merck et al. published Jul. 25, 2002, discloses a large genus of pyrimidine derivative nucleosides of the 2'-methyl-2' hydroxy substitutions. WO 2004/009020 to Merck et al. discloses a series of thionucleoside derivatives as inhibitors of RNA dependent RNA viral polymerase. WO 03/105770 to Merck et al. discloses a series of carbocyclic nucleoside derivatives that are useful for the treatment of HCV infections.

PCT Publication No. WO 99/43691 to Emory University, entitled "2'-Fluoronucleosides" discloses the use of certain 2'-fluoronucleosides to treat HCV. U.S. Pat. No. 6,348,587 to Emory University entitled "2'-fluoronucleosides" discloses a family of 2'-fluoronucleosides useful for the treatment of hepatitis B, HCV, HIV and abnormal cellular proliferation. The 2' substitutent is disclosed to be in either the "up" or "down" position.

Eldrup et al. (Oral Session V, Hepatitis C Virus, Flaviviridae; 16th International Conference on Antiviral Research (Apr. 27, 2003, Savannah, Ga.)) described the structure activity relationship of 2'-modified nucleosides for inhibition of HCV.

Bhat et al. (Oral Session V, Hepatitis C Virus, Flaviviridae; 16$^{th}$ International Conference on Antiviral Research (Apr. 27, 2003, Savannah, Ga.); p A75) describe the synthesis and pharmacokinetic properties of nucleoside analogues as possible inhibitors of HCV RNA replication. The authors report that 2'-modified nucleosides demonstrate potent inhibitory activity in cell-based replicon assays.

Olsen et al. (Oral Session V, Hepatitis C Virus, Flaviviridae; 16$^{th}$ International Conference on Antiviral Research (Apr. 27, 2003, Savannah, Ga.) p A76) also described the effects of the 2'-modified nucleosides on HCV RNA replication.

Other miscellaneous compounds including 1-amino-alkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846, 964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2,3-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056, 961), and piperidenes (U.S. Pat. No. 5,830,905 to Diana et al.).

Other compounds currently in preclinical or clinical development for treatment of hepatitis C virus infection include: Interleukin-10 by Schering-Plough, IP-SOI by Interneuron, Merimebodib (VX-497) by Vertex, AMANTADINE® (Symmetrel) by Endo Labs Solvay, HEPTAZYME® by RPI, IDN-6556 by Idun Pharma., XTL-002 by XTL., HCV/MFS9 by Chiron, CIVACIR® (hepatitis C Immune Globulin) by NABI, LEVOVIRIN® by ICN/Ribapharm, VIRAMIDINE® by ICN/Ribapharm, ZADAXIN® (thymosin alpha-1) by SciClone, thymosin plus pegylated interferon by Sci Clone, CEPLENE® (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc., JTK 003 by AKROS Pharma, BILN-2061 by Boehringer Ingelheim, CellCept (mycophenolate mofetil) by Roche, T67, a f3-tubulin inhibitor, by Tularik, a therapeutic vaccine directed to E2 by Innogenetics, FK788 by Fujisawa Healthcare, Inc., 1 dB 1016 (Siliphos, oral silybin-phosphatdylcholine phytosome), RNA replication inhibitors (VP50406) by ViroPharma/Wyeth, therapeutic vaccine by Intercell, therapeutic vaccine by Epimmune/Genencor, IRES inhibitor by Anadys, ANA 245 and ANA 246 by Anadys, immunotherapy (Therapore) by Avant, protease inhibitor by Corvas/SChering, helicase inhibitor by Vertex, fusion inhibitor by Trimeris, T cell therapy by CellExSys, polymerase inhibitor by Biocryst, targeted RNA chemistry by PTC Therapeutics, Dication by Immtech, Int., protease inhibitor by Agouron, protease inhibitor by Chiron/Medivir, antisense therapy by AVI BioPharma, antisense therapy by Hybridon, hemopurifier by Aethlon Medical, therapeutic vaccine by Merix, protease inhibitor by Bristol-Myers Squibb/Axys, Chron-VacC, a therapeutic vaccine, by Tripep, UT 231 B by United Therapeutics, protease, helicase and polymerase inhibitors by Genelabs Technologies, IRES inhibitors by Immusol, R803 by Rigel Pharmaceuticals, INFERGEN® (interferon alpha-con-1) by InterMune, OMNIFERON® (natural interferon) by Viragen, ALBUFERON® by Human Genome Sciences, REBIF® (interferon beta-la) by Ares-Serono, Omega Interferon by BioMedicine, Oral Interferon Alpha by Amarillo Biosciences, interferon gamma, interferon tau, and Interferon gamma-1b by InterMune. Rigel Pharmaceuticals is developing a non-nucleoside HCV polymerase inhibitor, R803, that shows promise as being synergistic with IFN and ribavirin.

A summary of several investigational drugs, including several discussed above, that are currently in various phases of development for the treatment of HCV, are summarized below:

| Drug | Mechanism/Target | Company | U.S. Status |
|---|---|---|---|
| BILN-2061 | NS3 Serine-protease inhibitor | Boehringer Ingelheim | Phase II |
| ISIS 14803 | Antisense/Prevent Translation of RNA | ISIS/Elan | Phase II |
| Viramidine | Prodrug of Ribavirin | Ribapharm | Phase II |
| NM283 | Inhibitor of HCV RNA Polymerase | Idenix | Phase II/III |
| VX-497 | IMPDH Inhibitor | Vertex | Phase I/II |
| JKT-003 | Inhibitor of HCV RNA Polymerase | Japan Tobacco/ Akros | Phase I/II |
| Levovirin | L-Ribavirin analog | Ribapharm/Roche | Phase I/II |
| Isatoribine; ANA245 | Nucleoside analog Interact with TLR7 receptor | Anadys | Phase I |
| Albuferon | Immune modulator | Human Genome Sciences | Phase I |
| Peg-Infergen | Immune modulator | Intermune | Phase I |
| VX-950 | Inhibitor of HCV NS3-4A protease | Vertex | Preclinical |
| SCH 6 | Inhibitor of HCV NS3-4A protease | Schering Plough | Preclinical |
| R803 | Inhibitor of HCV RNA polymerase | Rigel | Phase I |
| HCV-086 | — | ViroPharma/Wyeth | Phase I |
| R1479 | Inhibitor of HCV RNA polymerase | Roche | Phase I |

Nucleoside prodrugs have been previously described for the treatment of other forms of hepatitis. WO 00/09531 and WO 01/96353 to Idenix Pharmaceuticals, discloses 2'-deoxy-β-L-nucleosides and their 3'-prodrugs for the treatment of HBV. U.S. Pat. No. 4,957,924 to Beauchamp discloses various therapeutic esters of acyclovir.

In light of the fact that HCV infection has reached epidemic levels worldwide, and has tragic effects on the infected patient, there remains a strong need to provide new effective pharmaceutical agents to treat hepatitis C that have low toxicity to the host.

Further, given the rising threat of other flaviviridae infections, there remains a strong need to provide new effective pharmaceutical agents that have low toxicity to the host.

SUMMARY OF THE INVENTION

There is currently no preventive treatment of Hepatitis C virus (HCV), Dengue virus (DENV) or West Nile virus (WNV) infection, and currently approved therapies, which exist only against HCV, are limited. Design and development of pharmaceutical compounds is essential, especially those that are synergistic with other approved and investigational Flaviviridae, and in particular HCV, therapeutics for the evolution of treatment standards, including more effective combination therapies.

The present invention provides a (2'R)-2'-deoxy-2'-fluoro-2'-C-methyl nucleoside (β-D or β-L), or its pharmaceutically acceptable salt or prodrug thereof, and the use of such compounds for the treatment of a host infected with a virus belonging to the Flaviviridae family, including hepatitis C, West Nile Virus and yellow fever virus. In addition, the nucleosides of the present invention show actively against rhinovirus. Rhinoviruses (RVs) are small (30 nm), nonenveloped viruses that contain a single-strand ribonucleic acid (RNA) genome within an icosahedral (20-sided) capsid. RVs belong to the Picornaviridae family, which includes the genera Enterovirus (polioviruses, coxsackieviruses groups A and B, echoviruses, numbered enteroviruses) and Hepatovirus (hepatitis A virus). Approximately 101 serotypes are identified currently. Rhinoviruses are most frequently associated with the common cold, nasopharyngitis, croup, pneumonia, otitis media and asthma exacerbations.

The inventor has made the unexpected discovery that the 2' substitutions on the β-D or β-L nucleosides of the present invention impart greater specificity for hepatitis C virus as well as exhibiting lower toxicity following administration to a host. The invention also includes a method for treating a Flaviviridae infection, including hepatitis C virus, West Nile Virus and yellow fever virus and rhinovirus infection, that includes the administration of an anti-virally effective amount of a β-D or β-L nucleoside disclosed herein, or its pharmaceutically acceptable salt or prodrug, optionally in a pharmaceutically acceptable carrier or diluent, optionally in combination or alternation with another effective antiviral agent.

The nucleosides of the present invention, possess the unique properties of having greater specificity for the hepatitis C virus and lower toxicity in culture or when administered into an animal. One potential, but non-limiting reason for this is the presence of the 2'-fluoro substitution on the ribose ring. For example, U.S. Pat. No. 6,348,587 to Schinazi et al., discloses a family of 2'-fluoro nucleoside compounds that are useful in the treatment of hepatitis C virus infection. In contrast, are 2'-methyl substitutions such as found in 2'-C-methylcytidine as shown in WO 2004/02999 to Idenix wherein the 2'-methyl substitution on the nucleoside ring at the 2' position is not specific to hepatitis C.

Thus, in one aspect, the antivirally effective nucleoside is a (2'R)-2'-deoxy-2'-fluoro-2'-C-methyl nucleoside (β-D or β-L) or its pharmaceutically acceptable salt or prodrug thereof of the general formula:

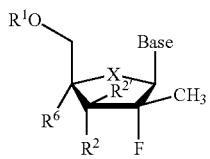

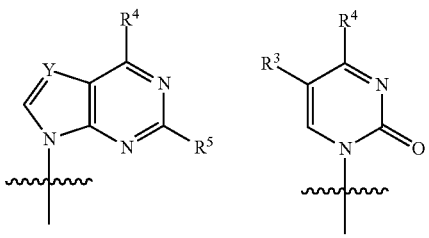

wherein

1. Base is a naturally occurring or modified purine or pyrimidine base;

2. X is O, S, $CH_2$, Se, NH, N-alkyl, CHW (R,S, or racemic), $C(W)_2$, wherein W is F, Cl, Br, or I;

3. $R^1$ and $R^7$ are independently H, phosphate, including 5'-monophosphate, diphosphate, triphosphate, or a stabilized phosphate prodrug, H-phosphonate, including stabilized H-phosphonates, acyl, including optionally substituted phenyl and lower acyl, alkyl, including lower alkyl, O-substituted carboxyalkylamino or its peptide derivatives, sulfonate ester, including alkyl or arylalkyl sulfonyl, including methanesulfonyl and benzyl, wherein the phenyl group is optionally substituted, a lipid, including a phospholipid, an L or D-amino acid, a carbohydrate, a peptide, a cholesterol, or other pharmaceutically acceptable leaving group which when administered in vivo is capable of providing a compound wherein $R^1$ is H or phosphate; $R^2$ is OH or phosphate; $R^1$ and $R^2$ or $R^7$ can also be linked with cyclic phosphate group; and 4. $R^2$ and $R^{2'}$ are independently H, $C_{1-4}$ alkyl, $C_{1-4}$ alkenyl, $C_{1-4}$ alkynyl, vinyl, $N_3$, CN, Cl, Br, F, I, $NO_2$, $C(O)O(C_{1-4}$ alkyl), $C(O)O(C_{1-4}$ alkyl), $C(O)O(C_{1-4}$ alkynyl), $C(O)O(C_{1-4}$ alkenyl), $O(C_{1-4}$ acyl), $O(C_{1-4}$ alkyl), $O(C_{1-4}$ alkenyl), $S(C_{1-4}$ acyl), $S(C_{1-4}$ alkyl), $S(C_{1-4}$ alkynyl), $S(C_{1-4}$ alkenyl), $SO(C_{1-4}$ acyl), $SO(C_{1-4}$ alkyl), $SO(C_{1-4}$ alkynyl), $SO(C_{1-4}$ alkenyl), $SO_2(C_{1-4}$ acyl), $SO_2(C_{1-4}$ alkyl), $SO_2(C_{1-4}$ alkynyl), $SO_2(C_{1-4}$ alkenyl), $O_3S(C_{1-4}$ acyl), $O_3S(C_{1-4}$ alkyl), $O_3S(C_{1-4}$ alkenyl), $NH_2$, $NH(C_{1-4}$ alkyl), $NH(C_{1-4}$ alkenyl), $NH(C_{1-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{1-4}$ alkynyl), $C(O)O(C_{1-4}$ alkenyl), $O(C_{1-4}$ acyl), $O(C_{1-4}$ alkyl), $O(C_{1-4}$ alkenyl), $S(C_{1-4}$ acyl), $S(C_{1-4}$ alkyl), $S(C_{1-4}$ alkynyl), $S(C_{1-4}$ alkenyl), $SO(C_{1-4}$ acyl), $SO(C_{1-4}$ alkyl), $SO(C_{1-4}$ alkynyl), $SO(C_{1-4}$ alkenyl), $SO_2(C_{1-4}$ acyl), $SO_2(C_{1-4}$ alkyl), $SO_2(C_{1-4}$ alkynyl), $SO_2(C_{1-4}$ alkenyl), $O_3S(C_{1-4}$ acyl), $O_3S(C_{1-4}$ alkyl), $O_3S(C_{1-4}$ alkenyl), $NH_2$, $NH(C_{1-4}$ alkyl), $NH(C_{1-4}$ alkenyl), $NH(C_{1-4}$ alkynyl), $NH(C_{1-4}$ acyl), $N(C_{1-4}$ alkyl)$_2$, $N(C_{1-4}$ acyl)$_2$, $R^2$ and $R^{2'}$ can be together to form a vinyl optionally substituted by one or two of $N_3$, CN, Cl, Br, F, I, $NO_2$; $OR^7$ and 5. $R^6$ is an optionally substituted alkyl (including lower alkyl), cyano (CN), $CH_3$, $OCH_3$, $OCH_2CH_3$, hydroxy methyl ($CH_2OH$), fluoromethyl($CH_2F$), azido ($N_3$), CHCN, $CH_2N_3$, $CH_2NH_2$, $CH_2NHCH_3$, $CH_2N(CH_3)_2$, alkyne (optionally substituted), or fluoro.

In various aspects of the invention, the Base can be selected from wherein

FIG. 1 Y is N or CH.

FIG. 2 $R^3$, $R^4$ and $R^5$ are independently H, halogen (including F, Cl, Br, I), OH, OR', SH, SR', $NH_2$, NHR', NR'$_2$, lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as CH=$CH_2$, halogenated (F, Cl, Br, I) lower alkenyl of $C_2$-$C_6$ such as CH=CHCl, CH=CHBr and CH=CHI, lower alkynyl of $C_2$-$C_6$ such as C≡CH, halogenated (F, Cl, Br, I) lower alkynyl of $C_2$-$C_6$, lower alkoxy of $C_1$-$C_6$ such as $CH_2OH$ and $CH_2CH_2OH$, halogenated (F, Cl, Br, I) lower alkoxy of $C_1$-$C_6$, $CO_2H$, $CO_2R'$, $CONH_2$, CONHR', CONR'$_2$, CH=CHCO$_2$H, CH=CHCO$_2$R';

wherein R' is an optionally substituted alkyl of $C_1$-$C_{12}$ (particularly when the alkyl is, an amino acid residue), cycloalkyl, optionally substituted alkynyl of $C_2$-$C_6$, optionally substituted lower alkenyl of $C_2$-$C_6$, or optionally substituted acyl.

In still another aspect, the (2'R)-2'-deoxy-2'-fluoro-2'-C-methyl nucleoside or its pharmaceutically acceptable salt or prodrug thereof can be of the formula:

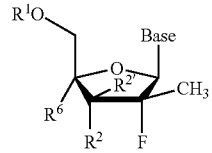

wherein

FIG. 1 Base, Y, R', $R^2$, $R^{2'}$, $R^3$, $R^4$, $R^5$, $R^6$, $R^7$ and R' are as described above.

Various aspects of the present invention also include pharmaceutical compositions comprising any of the (2'R)-2'-deoxy-2'-fluoro-2'-C-methyl nucleoside (β-D or β-L) described herein or their pharmaceutically acceptable salts or prodrugs thereof and a pharmaceutically acceptable carrier.

The present invention also provides in various aspects, methods for the treatment or prophylaxis of hepatitis C virus infection, West Nile virus infection, a yellow fever viral infection or a rhinovirus infection comprising administering to a host an antivirally effective amount of a (2'R)-2'-deoxy-2'-fluoro-2'-C-methyl nucleoside disclosed herein. The invention also includes methods for treating or preventing Flaviviridae infection, including all members of the Hepacivirus genus (HCV), Pestivirus genus (BVDV, CSFV, BDV), or Flavivirus genus (Dengue virus, Japanese encephalitis virus group (including West Nile Virus), and Yellow Fever virus).

In various aspects, the (2'R)-2'-deoxy-2'-fluoro-2'-C-methyl β-D-nucleoside has an $EC_{50}$ (effective concentration to achieve 50% inhibition) when tested in an appropriate cell-based assay, of less than 15 micromolar, and more particularly, less than 10 or 5 micromolar. In other aspects, the nucleoside is enantiomerically enriched.

The present invention also provides methods for the treatment or prophylaxis of a hepatitis C virus infection, West Nile virus infection, a yellow fever viral infection or a rhinovirus infection in a host comprising administering an effective amount of a (2′R)-2′-deoxy-2′-fluoro-2′-C-methyl nucleosides (β-D or β-L) disclosed herein, or its pharmaceutically acceptable salt or prodrug thereof, in combination or alternation with one or more other effective antiviral agent(s), optionally in a pharmaceutically acceptable carrier or diluent thereof, as described herein. Nonlimiting examples of the types of antiviral agents or their prodrugs that can be used in combination with the compounds disclosed herein include, but are not limited to: interferon, including interferon alpha 2a, interferon alpha 2b, a pegylated interferon, interferon beta, interferon gamma, interferon tau and interferon omega; an interleukin, including interleukin 10 and interleukin 12; ribavirin; interferon in combination with ribavirin; a protease inhibitor including NS3 inhibitor; a helicase inhibitor; a polymerase inhibitor; gliotoxin; an IRES inhibitor; and antisense oligonucleotide; a thiazolidine derivative; a benzanilide, a ribozyme; another nucleoside, nucleoside prodrug or nucleoside derivative; a 1-amino-alkylcyclohexane; an antioxidant including vitamin E; squalene; amantadine; a bile acid; N-(phosphonoacetyl)-L-aspartic acid; a benzenedicarboxamide; polyadneylic acid; a benzimidazoles; thymosin; a beta tubulin inhibitor; a prophylactic vaccine; silybin-phosphatidlycholine phytosome; and mycophenolate.

The following non-limiting aspects illustrate some general methodology to obtain the nucleosides of the present invention. Specifically, the synthesis of the present nucleosides can be achieved by either of two general means:

(a) alkylating the appropriately modified carbohydrate building block, subsequent fluorination, followed by coupling to form the nucleosides of the present invention (Scheme 1) or (b) glycosylation to form the nucleoside followed by alkylation and fluorination of the pre-formed nucleosides of the present invention (Scheme 2).

In addition, the L-enantiomers corresponding to the compounds of the invention can be prepared following the same general methods (Schemes 1 or 2), beginning with the corresponding L-carbohydrate building block or nucleoside L-enantiomer as the starting material.

Thus, the present invention includes at least the following general features:

A. β-D and β-L nucleosides of the general formulas disclosed, or their pharmaceutically acceptable salts or prodrugs thereof, as described herein;

B. processes for the preparation of the β-D and β-L nucleosides of the general formula disclosed, or their pharmaceutically acceptable salts or prodrugs thereof, as described herein;

C. pharmaceutical compositions comprising a β-D or β-L nucleoside of the general formulas disclosed, or its pharmaceutically acceptable salt or prodrug thereof, in a pharmaceutically acceptable carrier or diluent thereof, as described herein, for the treatment or prophylaxis of a viral infection in a host;

D. pharmaceutical compositions comprising a β-D or β-L nucleoside of the general formulas disclosed, or its pharmaceutically acceptable salt or prodrug thereof, in combination with one or more other effective antiviral agent(s), optionally in a pharmaceutically acceptable carrier or diluent thereof, as described herein, for the treatment or prophylaxis of a viral infection in a host;

E. methods for the treatment or prophylaxis of a Flaviviridae infection, including hepatitis C virus, West Nile Virus and yellow fever virus and rhinovirus infection in a host comprising administering an effective amount of a β-D or β-L nucleoside of the general formulas disclosed, or its pharmaceutically acceptable salt or prodrug thereof, optionally in a pharmaceutically acceptable carrier or diluent thereof, as described herein;

F. methods for the treatment or prophylaxis of a Flaviviridae infection, including hepatitis C virus, West Nile Virus and yellow fever virus and rhinovirus infection in a host comprising administering an effective amount of a β-D or β-L nucleoside of the general formulas disclosed, or its pharmaceutically acceptable salt or prodrug thereof, in combination or alternation with one or more other effective antiviral agent(s), optionally in a pharmaceutically acceptable carrier or diluent thereof, as described herein;

G. use of a β-D or β-L nucleoside of the general formulas disclosed, or its pharmaceutically acceptable salt or prodrug thereof, optionally in a pharmaceutically acceptable carrier, as described herein, for the treatment or prophylaxis of a Flaviviridae infection, including hepatitis C virus, West Nile Virus and yellow fever virus and rhinovirus infection in a host;

H. use of a β-D or β-L nucleoside of the general formulas disclosed, or its pharmaceutically acceptable salt or prodrug thereof, in combination or alternation with one or more other effective antiviral agent(s), optionally in a pharmaceutically acceptable carrier, as described herein, for the treatment or prophylaxis of a Flaviviridae infection, including hepatitis C virus, West Nile Virus and yellow fever virus and rhinovirus infection in a host;

I. use of a β-D or β-L nucleoside of the general formulas disclosed, or its pharmaceutically acceptable salt or prodrug thereof, optionally in a pharmaceutically acceptable carrier, as described herein, in the manufacture of a medicament for the treatment or prophylaxis of a Flaviviridae infection, including hepatitis C virus, West Nile Virus and yellow fever virus and rhinovirus infection in a host;

J. use of a β-D or β-L nucleoside of the general formulas disclosed, or its pharmaceutically acceptable salt or prodrug thereof, in combination or alternation with one or more other effective antiviral agent(s), optionally in a pharmaceutically acceptable carrier, as described herein, in the manufacture of a medicament for the treatment or prophylaxis of a Flaviviridae infection, including hepatitis C virus, West Nile Virus and yellow fever virus and rhinovirus infection in a host;

K. use of a β-D or β-L nucleoside of the general formulas disclosed, or its pharmaceutically acceptable salt or prodrug thereof, optionally in a pharmaceutically acceptable carrier or diluent, as described herein, in a medical therapy, i.e. as antiviral for example for the treatment or prophylaxis of a Flaviviridae infection, including hepatitis C virus, West Nile Virus and yellow fever virus and rhinovirus infection;

L. use of a β-D or β-L nucleoside of the general formulas disclosed, as described herein, or its pharmaceutically acceptable salt or prodrug thereof, i.e. as antiviral agent, in combination or alternation with one or more other effective therapeutic agent(s), i.e. another antiviral agent, optionally in a pharmaceutically acceptable carrier or diluent, as described herein, in a medical therapy, for example for the treatment or prophylaxis of a Flaviviridae infection, including hepatitis C virus, West Nile Virus and yellow fever virus and rhinovirus infection in a host.

DETAILED DESCRIPTION OF THE INVENTION

Figure 1A:
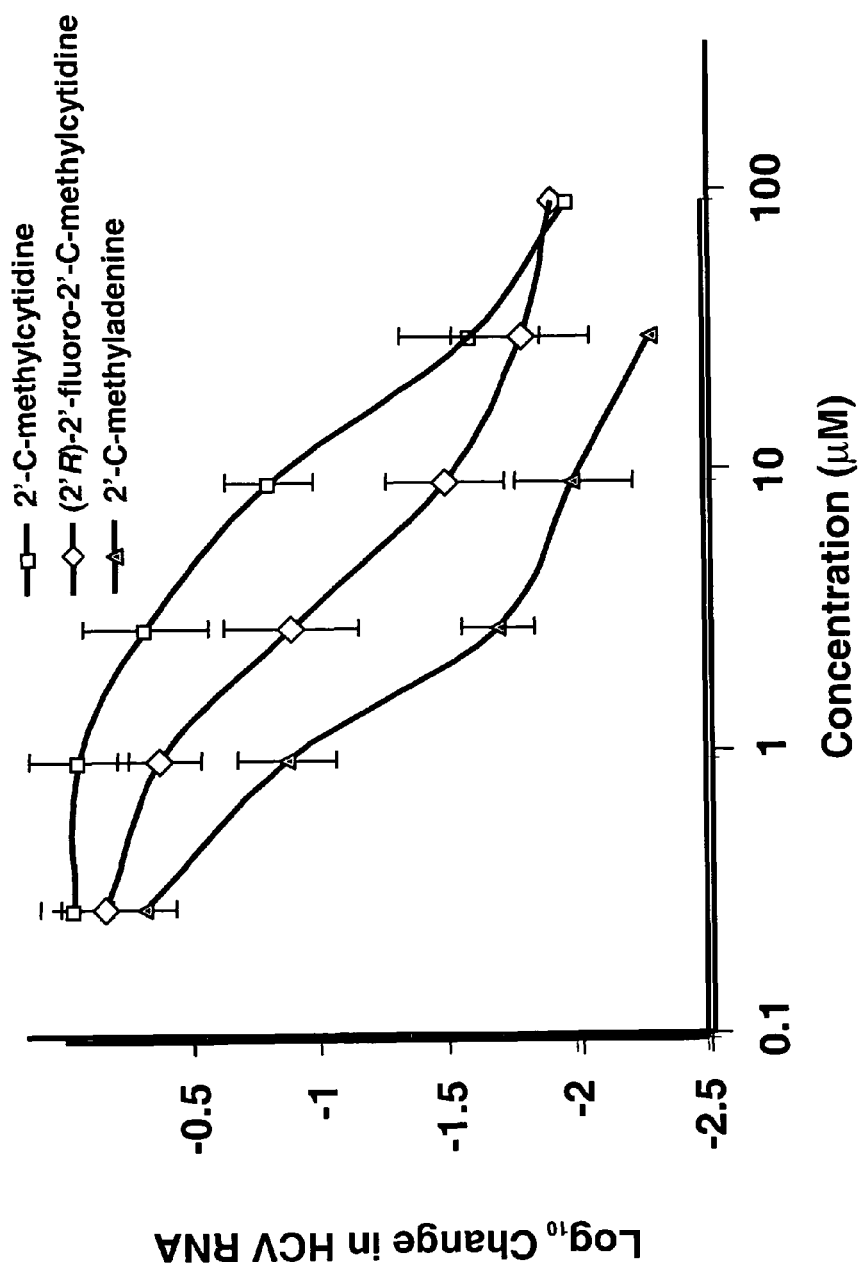
FIG. 1 is a graphical depiction of the dose-dependent reduction of the replicon HCV RNA based on the treatment with β-D-(2'R)-2'-deoxy-2'-fluoro-2'-C-methylcytidine. (A): The viral reduction was compared to the reduction of cellular RNA levels (ribosomal RNA) to obtain therapeutic index values. $EC_{90}$ which represents the effective concentration 90% at 96 hours following the dose dependent administration of (2'R)-2'-deoxy-2'-fluoro-2'-C-methylcytidine was determined to be 5 μM. (B): HCV RNA was significantly reduced in a dose-dependent manner for 7 days following treatment with 25 μM.

Various embodiments of the invention are now described in detail. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing the compositions and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The present invention provides (2'R)-2'-deoxy-2'-fluoro-2'-C-methyl nucleosides and their pharmaceutically acceptable salts and prodrugs for the treatment of hepatitis C virus infection, West Nile virus infection, a yellow fever viral infection or a rhinovirus infection in a host.

The disclosed compounds or their pharmaceutically acceptable derivatives or salts or pharmaceutically acceptable formulations containing these compounds are useful in the prevention and treatment of HCV infections. In addition, these compounds or formulations can be used prophylactically to prevent or retard the progression of clinical illness in individuals who are anti-HCV antigen positive or who have been exposed to HCV.

The compounds disclosed herein can be converted into a pharmaceutically acceptable ester by reaction with an appropriate esterifying agent, for example, an acid halide or anhydride. The compound or its pharmaceutically acceptable derivative can be converted into a pharmaceutically acceptable salt thereof in a conventional manner, for example, by treatment with an appropriate base. The ester or salt of the compound can be converted into the parent compound, for example, by hydrolysis.

Definitions

The term "independently" is used herein to indicate that the variable, which is independently applied, varies independently from application to application. Thus, in a compound such as $R^a XYR^a$, wherein $R^a$ is "independently carbon or nitrogen", both $R^a$ can be carbon, both $R^a$ can be nitrogen, or one $R^a$ can be carbon and the other $R^a$ nitrogen.

As used herein, the terms "enantiomerically pure" or "enantiomerically enriched" refers to a nucleoside composition that comprises at least approximately 95%, and preferably approximately 97%, 98%, 99% or 100% of a single enantiomer of that nucleoside.

As used herein, the term "substantially free of" or "substantially in the absence of" refers to a nucleoside composition that includes at least 85 or 90% by weight, preferably 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "alkyl," as used herein, unless otherwise specified, refers to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, or any other viable functional group that does not inhibit the pharmacological activity of this compound, either unprotected, or protected, as necessary, as known to those skilled in the art, for example, as taught in T. W. Greene and P. G. M. Wuts, "Protective Groups in Organic Synthesis," 3rd ed., John Wiley & Sons, 1999, hereby incorporated by reference.

The term "lower alkyl," as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred.

Similarly, when alkyl or lower alkyl is a suitable moiety, unsubstituted alkyl or lower alkyl is preferred.

The terms "alkylamino" or "arylamino" refer to an amino group that has one or two alkyl or aryl substituents, respectively.

The term "protected," as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis. Non-limiting examples include: C(O)-alkyl, C(O)Ph, C(O)aryl, $CH_3$, $CH_2$-alkyl, $CH_2$-alkenyl, $CH_2$Ph, $CH_2$-aryl, $CH_2$O-alkyl, $CH_2$O-aryl, $SO_2$-alkyl, $SO_2$-aryl, tert-butyldimethylsilyl, tert-butyldiphenylsilyl, and 1,3-(1,1,3,3-tetraisopropyldisiloxanylidene).

The term "aryl," as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

The term "lower acyl" refers to an acyl group in which the non-carbonyl moiety is lower alkyl.

The term "purine" or "pyrimidine" base includes, but is not limited to, adenine, $N^6$-alkylpurines, $N^6$-acylpurines (wherein acyl is C(O)(alkyl, aryl, alkylaryl, or arylalkyl)), $N^6$-benzylpurine, $N^6$-halopurine, $N^6$-vinylpurine, $N^6$-acetylenic purine, $N^6$-acyl purine, $N^6$-hydroxyalkyl purine, $N^6$-allylaminopurine, $N^6$-thioallyl purine, $N^6$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrimidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $N^4$-acetylcytosine, $N^4$-benzoylcytosine, $N^4$-alkyl pyrimidine, $C^5$-hydroxyalkyl purine, $C^5$-amidopyrimidine, $C^5$-cyanopyrimidine, $C^5$-iodopyrimidine, $C^6$-iodo-pyrimidine, $C^5$-Br-vinyl pyrimidine, $C^6$-Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" refers to a group of the formula C(O)R', wherein R' is an straight, branched, or cyclic alkyl (including lower alkyl), amino acid, aryl including phenyl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclopropylacetyl, cyclopropyl carboxy, propionyl, butyryl, hexanoyl, heptanoyl, octanoyl, neoheptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoroheptanoyl, 7H-dodecafluoroheptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoroethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl. When the term acyl is used, it is meant to be a specific and independent disclosure of acetyl, trifluoroacetyl, methylacetyl, cyclopropylacetyl, propionyl, butyryl, hexanoyl, heptanoyl, octanoyl, neo-heptanoyl, phenylacetyl, diphenylacetyl, ct-trifluoromethyl-phenylacetyl, bromoacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, 2-thiopheneacetyl, tert-butylacetyl, trichloroacetyl, monochloro-acetyl, dichloroacetyl, methoxybenzoyl, 2-bromo-propionyl, decanoyl, n-pentadecanoyl, stearyl, 3-cyclopentyl-propionyl, 1-benzene-carboxyl, pivaloyl acetyl, 1-adamantane-carboxyl, cyclohexane-carboxyl, 2,6-pyridinedicarboxyl, cyclopropane-carboxyl, cyclobutane-carboxyl, 4-methylbenzoyl, crotonyl, 1-methyl-1H-indazole-3-carbonyl, 2-propenyl, isovaleryl, 4-phenylbenzoyl.

The term "amino acid" includes naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-leucinyl, β-isoleucinyl, β-phenylalaninyl, β-tryptophanyl, β-methioninyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "host," as used herein, refers to a unicellular or multicellular organism in which the virus can replicate, including cell lines and animals, and preferably a human. Alternatively, the host can be carrying a part of the viral genome, whose replication or functions can be altered by the compounds of the present invention. The term host specifically refers to infected cells, cells transfected with all or part of the viral genome, and animals, in particular, primates and humans. In most animal applications of the present invention, the host is a human patient. Veterinary applications, in certain indications, however, are clearly anticipated by the present invention.

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

(1) Active Compound, and Physiologically Acceptable Derivatives and Salts Thereof A (2'R)-2'-deoxy-2'-fluoro-2'-C-methyl nucleoside or its pharmaceutically acceptable salt or prodrug thereof is provided of the structure:

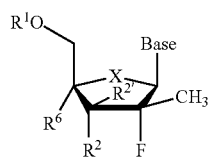

wherein Base refers to a naturally occurring or modified purine or pyrimidine base; X is O, S, $CH_2$, Se, NH, N-alkyl, CHW, $C(W)_2$, wherein W is F, Cl, Br, or I;

$R^1$ and $R^7$ are independently H, phosphate, including monophosphate, diphosphate, triphosphate, or a stabilized phosphate prodrug, H-phosphonate, including stabilized H-phosphonates, acyl, including optionally substituted phenyl and lower acyl, alkyl, including lower alkyl, O-substituted carboxyalkylamino or its peptide derivatives, sulfonate ester, including alkyl or arylalkyl sulfonyl, including methanesulfonyl and benzyl, wherein the phenyl group is optionally substituted, a lipid, including a phospholipid, an L or D-amino acid, a carbohydrate, a peptide, a cholesterol, or other pharmaceutically acceptable leaving group which when administered in vivo is capable of providing a compound wherein $R^1$ is H or phosphate; $R^2$ is OH or phosphate; $R^1$ and $R^2$ or $R^7$ can also be linked with cyclic phosphate group; and $R^2$ and $R^{2'}$ are independently H, $C_{1-4}$ alkyl, $C_{1-4}$ alkenyl, $C_{1-4}$ alkynyl, vinyl, $N_3$, CN, Cl, Br, F, I, $NO_2$, C(O)O($C_{1-4}$ alkyl), C(O)O($C_{1-4}$ alkyl), C(O)O($C_{1-4}$ alkynyl), C(O)O($C_{1-4}$ alkenyl), O($C_{1-4}$ acyl), O($C_{1-4}$ alkyl), O($C_{1-4}$ alkenyl), S($C_{1-4}$ acyl), S($C_{1-4}$ alkyl), S($C_{1-4}$ alkynyl), S($C_{1-4}$ alkenyl), SO($C_{1-4}$ acyl), SO($C_{1-4}$ alkyl), SO($C_{1-4}$ alkynyl), SO($C_{1-4}$ alkenyl), $SO_2$($C_{1-4}$ acyl), $SO_2$($C_{1-4}$ alkyl), $SO_2$($C_{1-4}$ alkynyl, $SO_2$($C_{1-4}$ alkenyl), $O_3S$($C_{1-4}$ acyl), $O_3S$($C_{1-4}$ alkyl), $O_3S$($C_{1-4}$ alkenyl), $NH_2$, NH($C_{1-4}$ alkyl), NH($C_{1-4}$ alkenyl), NH($C_{1-4}$ alkynyl), NH($C_{1-4}$ acyl), N($C_{1-4}$ alkyl)$_2$, N($C_{1-18}$ acyl)$_2$, wherein alkyl, alkynyl, alkenyl and vinyl are optionally substituted by $N_3$, CN, one to three halogen (Cl, Br, F, I), $NO_2$, C(O)O($C_{1-4}$ alkyl), C(O)O($C_{1-4}$ alkyl), C(O)O ($C_{1-4}$ alkynyl), C(O)O($C_{1-4}$ alkenyl), O($C_{1-4}$ acyl), O($C_{1-4}$ alkyl), O($C_{1-4}$ alkenyl), S($C_{1-4}$ acyl), S($C_{1-4}$ alkyl), S($C_{1-4}$ alkynyl), S($C_{1-4}$ alkenyl), SO($C_{1-4}$ acyl), SO($C_{1-4}$ alkyl), SO($C_{1-4}$ alkynyl), SO($C_{1-4}$ alkenyl), $SO_2$($C_{1-4}$ acyl), $SO_2$($C_{1-4}$ alkyl), $SO_2$($C_{1-4}$ alkynyl), $SO_2$ ($C_{1-4}$ alkenyl), $O_3S$($C_{1-4}$ acyl), $O_3S$($C_{1-4}$ alkyl), $O_3S$ ($C_{1-4}$ alkenyl), $NH_2$, NH($C_{1-4}$ alkyl), NH($C_{1-4}$ alkenyl), NH($C_{1-4}$ alkynyl), NH($C_{1-4}$ acyl), N($C_{1-4}$ alkyl)$_2$, N($C_{1-4}$ acyl)$_2$, OR$^7$, $R^2$ and $R^{2'}$ can be together to form a vinyl optionally substituted by one or two of $N_3$, CN, Cl, Br, F, I, $NO_2$; and $R^6$ is an optionally substituted alkyl (including lower alkyl), cyano (CN), $CH_3$, $OCH_3$, $OCH_2CH_3$, hydroxy methyl($CH_2OH$), fluoromethyl($CH_2F$), azido ($N_3$), CHCN, $CH_2N_3$, $CH_2NH_2$, $CH_2NHCH_3$, $CH_2N(CH_3)_2$, alkyne (optionally substituted), or fluoro.

In a second embodiment, a (2'R)-2'-deoxy-2'-fluoro-2'-C-methyl nucleoside or its pharmaceutically acceptable salt or prodrug thereof is provided of the structure:

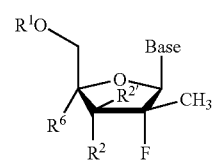

wherein Base, $R^1$, $R^2$, $R^{2'}$, $R^6$ and $R^7$ are as defined above.

A third embodiment provides a (2'R)-2'-deoxy-2'-fluoro-2'-C-methyl nucleoside or its pharmaceutically acceptable salt or prodrug thereof of the structure:

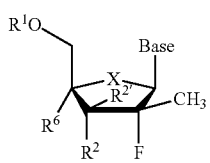

wherein X, R¹, R², R²', R⁶ and R⁷ are as defined above, and Base is selected from

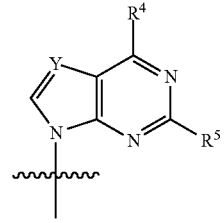

(a)

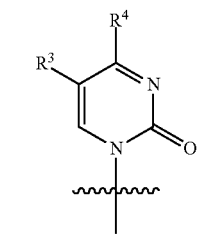

(b)

Y is N or CH;

R³, R⁴ and R⁵ are independently H, halogen (including F, Cl, Br, I), OH, OR', SH, SR', NH2, NHR', NR'$_2$, lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as $CH=CH_2$, halogenated (F, Cl, Br, I) lower alkenyl of $C_2$-$C_6$ such as CH=CHCl, CH=CHBr and CH=CHI, lower alkynyl of $C_2$-$C_6$ such as C≡CH, halogenated (F, Cl, Br, I) lower alkynyl of $C_2$-$C_6$, lower alkoxy of $C_1$-$C_6$ such as $CH_2OH$ and $CH_2CH_2OH$, halogenated (F, Cl, Br, I) lower alkoxy of $C_1$-$C_6$, $CO_2H$, $CO_2R'$, $CONH_2$, CONHR', CONR'$_2$, CH=CHCO$_2$H, CH=CHCO$_2$R';

R' is an optionally substituted alkyl of $C_1$-$C_{12}$ (particularly when the alkyl is an amino acid residue), cycloalkyl, optionally substituted alkynyl of $C_2$-$C_6$, optionally substituted lower alkenyl of $C_2$-$C_6$, or optionally substituted acyl.

In a fourth embodiment, a (2'R)-2'-deoxy-2'-fluoro-2'-C-methyl nucleoside or its pharmaceutically acceptable salt or prodrug thereof is provided of the structure:

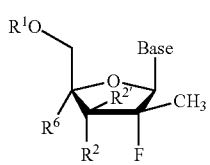

wherein Base is selected from

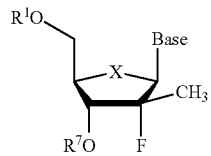

(a)

(b)

and, wherein R¹, R², R²', R³, R⁴, R⁵, R⁶ and Y are as defined above.

A fifth embodiment provides a (2'R)-2'-deoxy-2'-fluoro-2'-C-methyl nucleoside or its pharmaceutically acceptable salt or prodrug thereof of the structure:

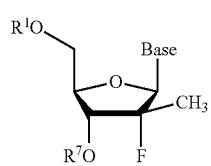

wherein Base refers to a naturally occurring or modified purine or pyrimidine base;

R⁷ is independently H, phosphate, including monophosphate, diphosphate, triphosphate, or a stabilized phosphate prodrug, H-phosphonate, including stabilized H-phosphonates, acyl, including optionally substituted phenyl and lower acyl, alkyl, including lower alkyl, O-substituted carboxyalkylamino or its peptide derivatives, sulfonate ester, including alkyl or arylalkyl sulfonyl, including methanesulfonyl and benzyl, wherein the phenyl group is optionally substituted, a lipid, including a phospholipid, an L or D-amino acid, a carbohydrate, a peptide, a cholesterol, or other pharmaceutically acceptable leaving group which when administered in vivo is capable of providing a compound wherein R¹ or R⁷ is independently H or phosphate; R¹ and R⁷ can also be linked with cyclic phosphate group; and wherein X and R¹ are as defined above.

In a sixth embodiment, a (2'R)-2'-deoxy-2'-fluoro-2'-C-methyl nucleoside or its pharmaceutically acceptable salt or prodrug thereof is provided of the structure:

wherein Base refers to a naturally occurring or modified purine or pyrimidine base; and wherein $R^1$ and $R^7$ are as defined above.

A seventh embodiment provides a (2'R)-2'-deoxy-2'-fluoro-2'-C-methyl nucleoside or its pharmaceutically acceptable salt or prodrug thereof of the structure:

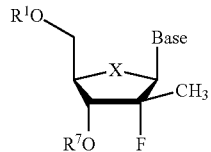

wherein Base is selected from

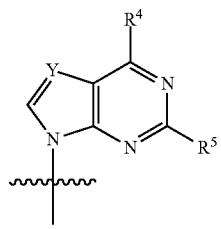

(a)

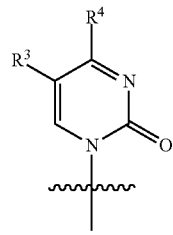

(b)

and wherein X, Y, $R^1$, $R^3$, $R^4$, $R^5$, $R^7$ and R' are as defined above.

In an eighth embodiment, a (2'R)-2'-deoxy-2'-fluoro-2'-C-methyl nucleoside or its pharmaceutically acceptable salt or prodrug thereof is provided of the structure:

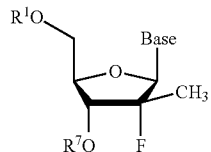

wherein Base is selected from

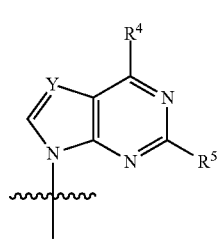

(a)

-continued

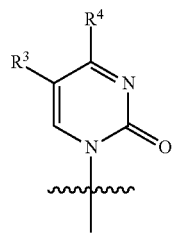

(b)

and, wherein Y, $R^1$, $R^3$, $R^4$, $R^5$, $R^7$ and R' are as defined above.

A ninth embodiment provides a (2'R)-2'-deoxy-2'-fluoro-2'-C-methyl nucleoside or its pharmaceutically acceptable salt or prodrug thereof of the structure:

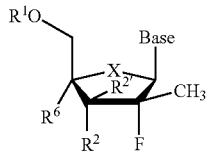

wherein Base is:

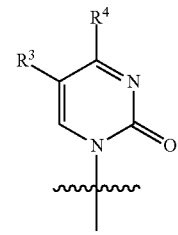

and wherein X is defined as above, $R^1$ is H, $R^2$ is OH, $R^2$ is H, $R^3$ is H, $R^4$ is $NH_2$ or OH, and $R^6$ is H.

In a tenth embodiment, a (2'R)-2'-deoxy-2'-fluoro-2'-C-methyl nucleoside or its pharmaceutically acceptable salt or prodrug thereof is provided of the structure:

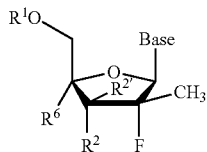

wherein Base is:

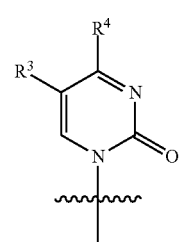

and wherein $R^1$ is H, $R^2$ is OH, $R^{2'}$ is H, $R^3$ is H, $R^4$ is $NH_2$ or OH, and $R^6$ is H.

An eleventh embodiment provides a (2'R)-2'-deoxy-2'-fluoro-2'-C-methyl nucleoside or its pharmaceutically acceptable salt or prodrug thereof of the structure:

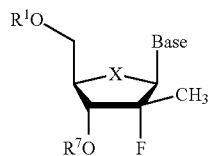

wherein Base is:

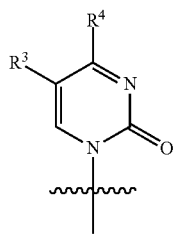

and wherein X is defined as above, $R^1$ is H, $R^3$ is H, $R^4$ is $NH^2$ or OH, $R^6$ is H, and $R^7$ is H.

In a twelfth embodiment, a (2'R)-2'-deoxy-2'-fluoro-2'-C-methyl nucleoside or its pharmaceutically acceptable salt or prodrug thereof is provided of the structure:

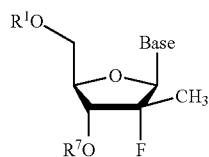

wherein Base is:

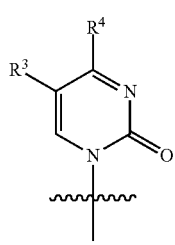

and wherein $R^1$ is H, $R^3$ is H, $R^4$ is $NH_2$ or OH, and $R^7$ is H.

A thirteenth embodiment provides a (2'R)-2'-deoxy-2'-fluoro-2'-C-methyl nucleoside or its pharmaceutically acceptable salt or prodrug thereof of the structure:

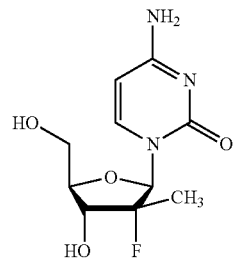

In a fourteenth embodiment, a (2'R)-2'-deoxy-2'-fluoro-2'-C-methyl nucleoside, its pharmaceutically acceptable salt or prodrug thereof is provided by the structure:

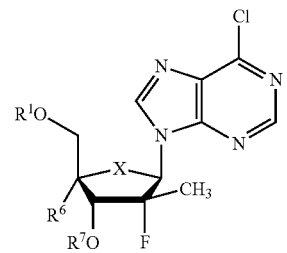

wherein X, $R^1$, $R^6$ and $R^7$ are as defined above.

In a fifteenth embodiment, a (2'R)-2'-deoxy-2'-fluoro-2'-C-methyl nucleoside, its pharmaceutically acceptable salt or prodrug thereof is provided by the structure:

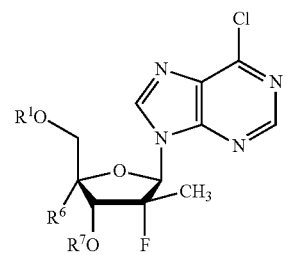

wherein $R^1$, $R^6$ and $R^7$ are as defined above.

In a sixteenth embodiment, a (2'R)-2'-deoxy-2'-fluoro-2'-C-methyl nucleoside nucleoside, its pharmaceutically acceptable salt or prodrug thereof is provided by the structure:

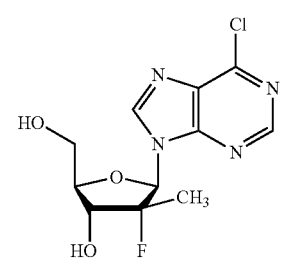

In a seventeenth embodiment, a (2'R)-2'-deoxy-2'-fluoro-2'-C-methyl nucleoside, its pharmaceutically acceptable salt or prodrug thereof is provided by the structure:

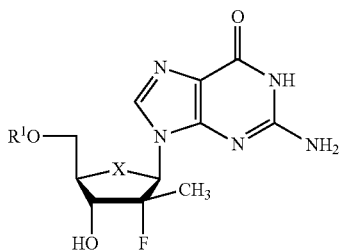

wherein X and R¹ are as defined above.

In an eighteenth embodiment, a (2'R)-2'-deoxy-2'-fluoro-2'-C-methyl nucleoside, its pharmaceutically acceptable salt or prodrug thereof is provided by the structure:

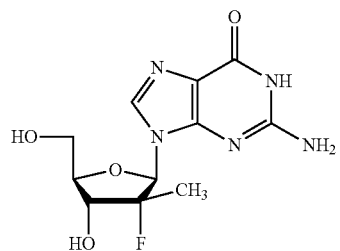

In a nineteenth embodiment, a (2'R)-2'-deoxy-2'-fluoro-2'-C-methyl nucleoside, its pharmaceutically acceptable salt or prodrug thereof is provided by the structure:

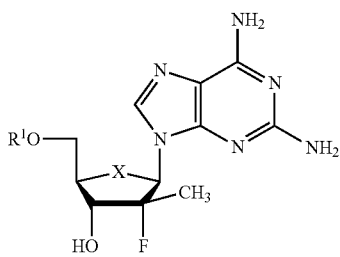

wherein X and R¹ are as defined above.

In a twentieth embodiment, a (2'R)-2'-deoxy-2'-fluoro-2'-C-methyl nucleoside, its pharmaceutically acceptable salt or prodrug thereof is provided by the structure:

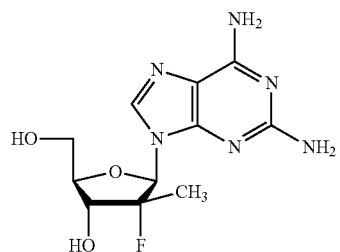

The present invention also contemplates 5'-triphosphate triphosphoric acid ester derivates of the 5'-hydroxyl group of a nucleoside compound of the present invention having the following general structural formula:

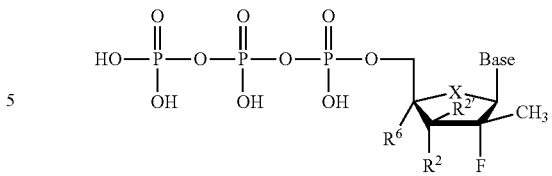

wherein Base, X, $R^2$, $R^{2'}$, and $R^6$ are as defined as above.

The compounds of the present invention are also intended to include pharmaceutically acceptable salts of the triphosphate ester as well as pharmaceutically acceptable salts of 5'-diphosphate and 5'-monophosphate ester derivatives of the following structural formulas, respectively.

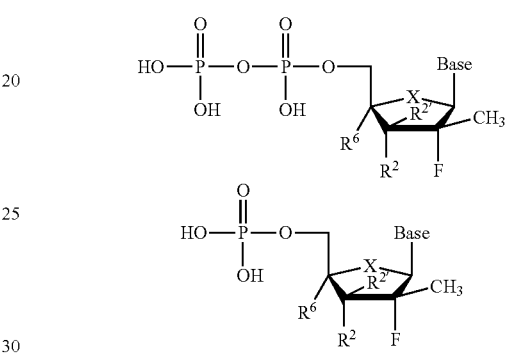

wherein Base, X, $R^2$, $R^{2'}$ and $R^6$ are as defined above.

Further non-limiting examples of phosphoric acid derivatives are the nucleosides of the present invention are shown below:

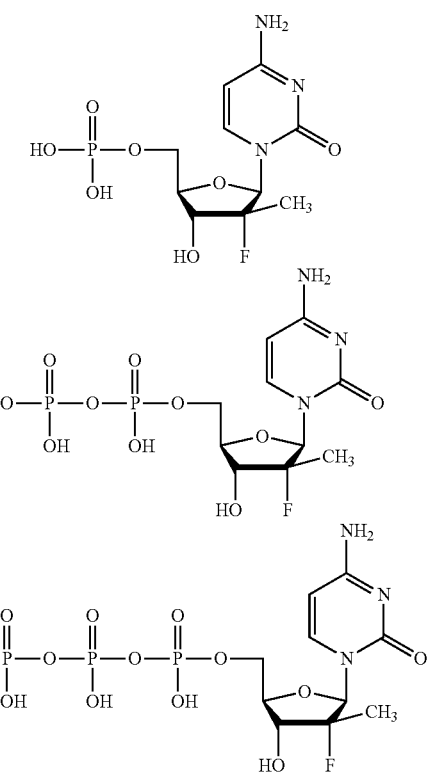

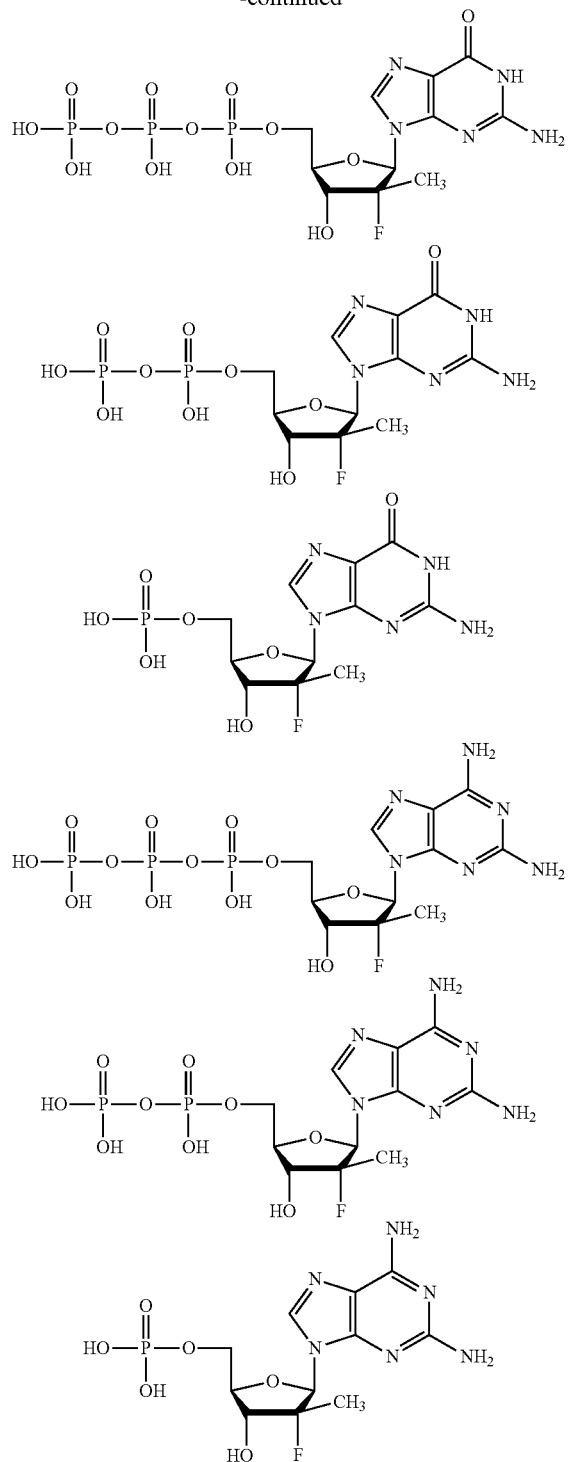

The present invention also contemplates that any phosphate nucleoside derivative can include a 5'-(S-acyl-2-thioethyl)phosphate or "SATE" mono or di-ester derivative of the 5'-monophosphates.

Alternative embodiments are also contemplated wherein the N-4 amino group on a phosphate nucleoside derivative can be replaced with H, F, Cl, Br or I.

Additional embodiments include 3' and/or 5' prodrugs as described in more detail herein.

In the various embodiments, the fluorinated derivatives are preferred. Fluorine is viewed as "isosteric" with hydrogen because of its size (Van der Waals radii for H is 1.20 Å and for F 1.35 Å). However, the atomic weight (18.998) and electronegativity of fluorine (4.0 [Pauling's scale], 4.000 [Sanderson's scale]) are more similar to oxygen (3.5 [Pauling], 3.654 [Sanderson]) than hydrogen (2.1 [Pauling], 2.592 [Sanderson]) (March, J., "Advances in Organic Chemistry: Reactions, Mechanisms, and Structure" Third edition, 1985, p. 14., Wiley Interscience, New York). Fluorine is known to be capable of forming a hydrogen bond, but unlike a hydroxyl group (which can act both as proton acceptor and proton donor) fluorine acts only as a proton acceptor. On the other hand, 2'-fluoro-ribonucleosides can be viewed as analogues of both ribonucleosides and deoxynucleosides. They may be better recognized by viral RNA polymerase at the triphosphate level than by the host RNA polymerase thus selectively inhibiting the viral enzyme.

(2) Pharmaceutically Acceptable Salts and Prodrugs

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art.

In particular, examples of pharmaceutically acceptable salts are organic acid addition salts formed with acids, which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1-17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses*. 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3'-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. Nos. 5,149,794; 5,194,654; 5,223,263; 5,256,641; 5,411,947; 5,463,092; 5,543,389; 5,543,390; 5,543,391; and 5,554,728, all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

(3) Pharmaceutical Compositions

Pharmaceutical compositions based upon a β-D or β-L, compound disclosed herein or its pharmaceutically acceptable salt or prodrug can be prepared in a therapeutically effective amount for treating a Flaviviridae infection, including hepatitis C virus, West Nile Virus, yellow fever virus, and a rhinovirus infection, optionally in combination with a pharmaceutically acceptable additive, carrier or excipient. The therapeutically effective amount may vary with the infection or condition to be treated, its severity, the treatment regimen to be employed, the pharmacokinetics of the agent used, as well as the patient treated.

In one aspect according to the present invention, the compound according to the present invention is formulated preferably in a mixture with a pharmaceutically acceptable carrier. In general, it is preferable to administer the pharmaceutical composition in orally administrable form, but formulations may be administered via parenteral, intravenous, intramuscular, transdermal, buccal, subcutaneous, suppository or other route. Intravenous and intramuscular formulations are preferably administered in sterile saline. One of ordinary skill in the art may modify the formulation within the teachings of the specification to provide numerous formulations for a particular route of administration without rendering the compositions of the present invention unstable or compromising its therapeutic activity. In particular, a modification of a desired compound to render it more soluble in water or other vehicle, for example, may be easily accomplished by routine modification (salt formulation, esterification, etc.).

In certain pharmaceutical dosage forms, the prodrug form of the compound, especially including acylated (acetylated or other) and ether derivatives, phosphate esters and various salt forms of the present compounds, is preferred. One of ordinary skill in the art will recognize how to readily modify the present compound to a prodrug form to facilitate delivery of active compound to a targeted site within the host organism or patient. The artisan also will take advantage of favorable pharmacokinetic parameters of the prodrug form, where applicable, in delivering the desired compound to a targeted site within the host organism or patient to maximize the intended effect of the compound in the treatment of a Flaviviridae infection, including hepatitis C virus, West Nile Virus, yellow fever virus, and a rhinovirus infection.

The amount of compound included within therapeutically active formulations, according to the present invention, is an effective amount for treating the infection or condition, in preferred embodiments, a Flaviviridae infection, including hepatitis C virus, West Nile Virus, yellow fever virus, and a rhinovirus infection. In general, a therapeutically effective amount of the present compound in pharmaceutical dosage form usually ranges from about 50 mg to about 2,000 mg or more, depending upon the compound used, the condition or infection treated and the route of administration. For purposes of the present invention, a prophylactically or preventively effective amount of the compositions, according to the present invention, falls within the same concentration range as set forth above for therapeutically effective amount and is usually the same as a therapeutically effective amount.

Administration of the active compound may range from continuous (intravenous drip) to several oral administrations per day (for example, Q.I.D., B.I.D., etc.) and may include oral, topical, parenteral, intramuscular, intravenous, subcutaneous, transdermal (which may include a penetration enhancement agent), buccal and suppository administration, among other routes of administration. Enteric-coated oral tablets may also be used to enhance bioavailability and stability of the compounds from an oral route of administration. The most effective dosage form will depend upon the pharmacokinetics of the particular agent chosen, as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably mixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated for sustained release by standard techniques. The use of these dosage forms may significantly impact the bioavailability of the compounds in the patient.

For parenteral formulations, the carrier will usually comprise sterile water or aqueous sodium chloride solution, though other ingredients, including those that aid dispersion, also may be included. Where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

In particularly preferred embodiments according to the present invention, the compounds and compositions are used to treat, prevent or delay the onset of a Flaviviridae infection, including hepatitis C virus, West Nile Virus, yellow fever virus, and a rhinovirus infection. The present compounds are preferably administered orally, but may be administered parenterally, topically or in suppository form.

The compounds according to the present invention, because of their low toxicity to host cells in certain instances, may be advantageously employed prophylactically to prevent a Flaviviridae infection, including hepatitis C virus, West Nile Virus, yellow fever virus, and a rhinovirus infection or to prevent the occurrence of clinical symptoms associated with the viral infection or condition. Thus, the present invention also encompasses methods for the prophylactic treatment of viral infection, and in particular a Flaviviridae infection, including hepatitis C virus, West Nile Virus, yellow fever virus, and a rhinovirus infection. In this aspect, according to the present invention, the present compositions are used to prevent or delay the onset of a Flaviviridae infection, including hepatitis C virus, West Nile Virus, yellow fever virus, and a rhinovirus infection. This prophylactic method comprises administration to a patient in need of such treatment, or who is at risk for the development of the virus or condition, an amount of a compound according to the present invention effective for alleviating, preventing or delaying the onset of the viral infection or condition. In the prophylactic treatment according to the present invention, it is preferred that the antiviral compound utilized should be low in toxicity and preferably non-toxic to the patient. It is particularly preferred in this aspect of the present invention that the compound that is used should be maximally effective against the virus or condition and should exhibit a minimum of toxicity to the patient. In the case of a Flaviviridae infection, including hepatitis C virus, West Nile Virus, yellow fever virus, and a rhinovirus infection, compounds according to the present invention, which may be used to treat these disease states, may be administered within the same dosage range for therapeutic treatment (i.e., about 250 micrograms up to 1 gram or more from one to four times per day for an oral dosage form) as a prophylactic agent to prevent the proliferation of the viral infection, or alternatively, to prolong the onset of the viral infection, which manifests itself in clinical symptoms.

In addition, compounds according to the present invention can be administered in combination or alternation with one or more antiviral agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

(4) Stereoisomerism and Polymorphism

It is appreciated that nucleosides of the present invention have several chiral centers and may exist in and be isolated in optically active and racemic forms. Some compounds may exhibit polymorphism. It is to be understood that the present invention encompasses any racemic, optically active, diastereomeric, polymorphic, or stereoisomeric form, or mixtures thereof, of a compound of the invention, which possess the useful properties described herein. It being well known in the art how to prepare optically active forms (for example, by resolution of the racemic form by recrystallization techniques, by synthesis from optically-active starting materials, by chiral synthesis, or by chromatographic separation using a chiral stationary phase).

Carbons of the nucleoside are chiral, their nonhydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a nonnaturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the nonnaturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following.

i. physical separation of crystals—a technique whereby macroscopic crystals of the individual enantiomers are manually separated. This technique can be used if crystals of the separate enantiomers exist, i.e., the material is a conglomerate, and the crystals are visually distinct;

ii. simultaneous crystallization—a technique whereby the individual enantiomers are separately crystallized from a solution of the racemate, possible only if the latter is a conglomerate in the solid state;

iii. enzymatic resolutions—a technique whereby partial or complete separation of a racemate by virtue of differing rates of reaction for the enantiomers with an enzyme; enzymatic asymmetric synthesis—a synthetic technique whereby at least one step of the synthesis uses an enzymatic reaction to obtain an enantiomerically pure or enriched synthetic precursor of the desired enantiomer; chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries; diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer; vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

vii. kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions; enantiospecific synthesis from non-racemic precursors—a synthetic technique whereby the desired enantiomer is obtained from non-chiral starting materials and where the stereochemical integrity is not or is only minimally compromised over the course of the synthesis; chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions; chiral gas chromatography—a technique whereby the racemate is volatilized and enantiomers are separated by virtue of their differing interactions in the gaseous mobile phase with a column containing a fixed non-racemic chiral adsorbent phase; extraction with chiral solvents—a technique whereby the enantiomers are separated by virtue of preferential dissolution of one enantiomer into a particular chiral solvent; transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through. Chiral chromatography, including simulated moving bed chromatography, is used in one embodiment. A wide variety of chiral stationary phases are commercially available.

Some of the compounds described herein contain olefinic double bonds and unless otherwise specified, are meant to include both E and Z geometric isomers.

In addition, some of the nucleosides described herein, may exist as tautomers, such as, keto-enol tautomers. The individual tautomers as well as mixtures thereof are intented to be encompassed within the compounds of the present invention as illustrated below.

A (2'R)-2'-deoxy-2'-fluoro-2'-C-methylcytidine:

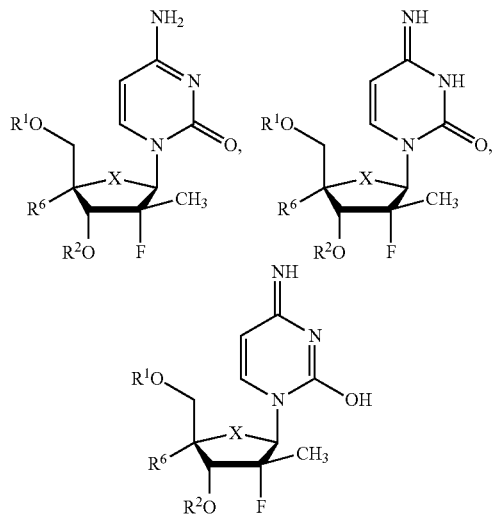

A (2'R)-2'-deoxy-2'-fluoro-2'-C-methylguanosine:

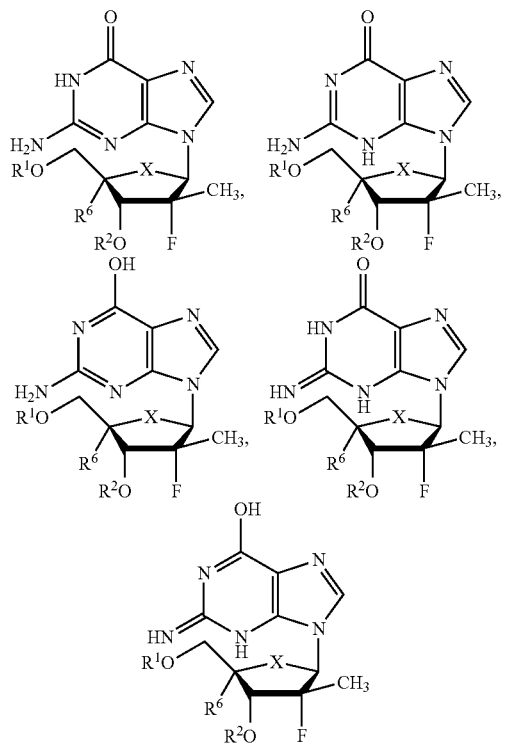

A (2'R)-2-amino-2'-deoxy-2'-fluoro-2'-C-methyladenosine:

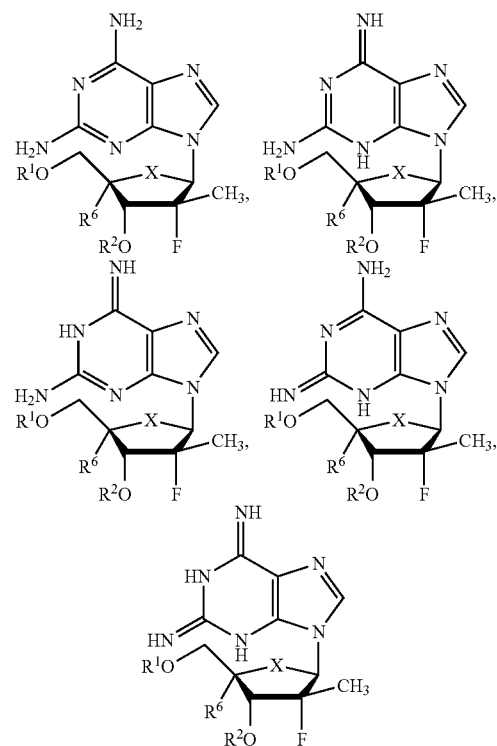

In each example above, the first drawn structure is the preferred form.

(5) Prodrugs and Derivatives

The active compound can be administered as any salt or prodrug that upon administration to the recipient is capable of providing directly or indirectly the parent compound, or that exhibits activity itself. Nonlimiting examples are the pharmaceutically acceptable salts (alternatively referred to as "physiologically acceptable salts"), and a compound, which has been alkylated, acylated, or otherwise modified at the 5'-position, or on the purine or pyrimidine base (a type of "pharmaceutically acceptable prodrug"). Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

Pharmaceutically Acceptable Salts

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed by addition of acids, which form a physiological acceptable anion, for example, tosylate, methanesulfonate, acetate, citrate, malonate, tartrate, succinate, benzoate, ascorbate, α-ketoglutarate, α-glycerophosphate, formate, fumarate, propionate, glycolate, lactate, pyruvate, oxalate, maleate, and salicylate. Suitable inorganic salts may also be formed, including, sulfate, nitrate, bicarbonate, carbonate salts, hydrobromate and phosphoric acid. In a preferred embodiment, the salt is a mono- or di-hydrochloride salt.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made. In one embodiment, the salt is a hydrochloride, hydrobromide, or mesylate salt of the compound. In another embodiment, the pharmaceutically acceptable salt is a dihydrochloride, dihydrobromide, or dimesylate salt.

Nucleotide Prodrug Formulations

The nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono-, di- or triphosphate of the nucleoside reduces polarity and allows passage into cells. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, Antiviral Research, 1995, 27:1-17. Any of these can be used in combination with the disclosed nucleosides to achieve a desired effect.

In an alternative embodiment, the nucleoside is delivered as a phosphonate or a SATE derivative.

The active nucleoside can also be provided as a 2'-, 3'- and/or 5'-phosphoether lipid or a 2'-, 3'- and/or 5'-ether lipid. Non-limiting examples are described include the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." AIDS Res. Hum. Retro Viruses. 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C A. Wallen, S. Piantadosi, and E. J. Modest. 1991. "Synthesis and evaluation of novel ether lipid nucleoside conjugates for anti-HIV activity." J. Med. Chem. 34:1408.1414; Hostetler, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymine diphosphate dimyristoylglycerol, a lipid prodrug of 3,-deoxythymine." AntInzicrob. Agents Chemother. 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." J. Biol. Chem. 265:61127.

Nonlimiting examples of U.S. patents that disclose suitable lipophilic substituents that can be covalently incorporated into the nucleoside, preferably at the 2'-, 3'- and/or 5'-OH position of the nucleoside or lipophilic preparations, include U.S. Pat. Nos. 5,149,794 (Sep. 22, 1992, Yatvin et al.); 5,194,654 (Mar. 16, 1993, Hostetler et al., 5,223,263 (Jun. 29, 1993, Hostetler et al.); 5,256,641 (Oct. 26, 1993, Yatvin et al.); 5,411,947 (May 2, 1995, Hostetler et al.); 5,463,092 (Oct. 31, 1995, Hostetler et al.); 5,543,389 (Aug. 6, 1996, Yatvin et al.); 5,543,390 (Aug. 6, 1996, Yatvin et al.); 5,543,391 (Aug. 6, 1996, Yatvin et al.); and 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0350287, EP 93917054.4, and WO 91/19721.

Aryl esters, especially phenyl esters, are also provided. Nonlimiting examples are disclosed in DeLambert et al., J. Med. Chem. 37: 498 (1994). Phenyl esters containing a carboxylic ester ortho to the phosphate are also provided. Khaninei and Torrence, J. Med. Chem.; 39:41094115 (1996). In particular, benzyl esters, which generate the parent compound, in some cases using substituents at the ortho- or para-position to accelerate hydrolysis, are provided. Examples of this class of prodrugs are described by Mitchell et al., J. Chem. Soc. Perkin Trans. 12345 (1992); Brook, et al. WO 91/19721; and Glazier et al. WO 91/1 9721.

Cyclic and noncyclic phosphonate esters are also provided. Nonlimiting examples are disclosed in Hunston et al., J. Med. Chem. 27: 440-444 (1984) and Starrett et al. J. Med. Chem. 37: 1857-1864 (1994). Additionally, cyclic 3',5'-phosphate esters are provided. Nonlimiting examples are disclosed in Meier et al. J. Med. Chem. 22: 811-815 (1979). Cyclic 1',3'-propanyl phosphonate and phosphate esters, such as ones containing a fused aryl ring, i.e. the cyclosaligenyl ester, are also provided (Meier et al., Bioorg. Med. Chem. Lett. 7: 99-104 (1997)). Unsubstituted cyclic 1',3'-propanyl esters of the monophosphates are also provided (Farquhar et al., J. Med. Chem. 26: 1153 (1983); Farquhar et al., J. Med. Chem. 28: 1358 (1985)) were prepared. In addition, cyclic 1',3'-propanyl esters substituted with a pivaloyloxy methyloxy group at C-1' are provided (Freed et al., Biochem. Pharmac. 38: 3193 (1989); Biller et al., U.S. Pat. No. 5,157,027).

Cyclic phosphoramidates are known to cleave in vivo by an oxidative mechanism. Therefore, in one embodiment of the present invention, a variety of substituted 1',3' propanyl cyclic phosphoramidates are provided. Non-limiting examples are disclosed by Zon, Progress in Med. Chem. 19, 1205 (1982).

Additionally, a number of 2'- and 3'-substituted proesters are provided. 2'-Substituents include methyl, dimethyl, bromo, trifluoromethyl, chloro, hydroxy, and methoxy; 3'-substituents including phenyl, methyl, trifluoromethyl, ethyl, propyl, i-propyl, and cyclohexyl. A variety of 1'-substituted analogs are also provided.

Cyclic esters of phosphorus-containing compounds are also provided. Non-limiting examples are described in the following:
- di and tri esters of phosphoric acids as reported in Nifantyev et al., Phosphorus, Sulfur Silicon and Related Eelements, 113: 1 (1996); Wijnberg et al., EP-180276 A1;
- phosphorus (III) acid esters. Kryuchkov et al., Izy. Akad. Nauk SSSR, Ser. Khim. 6:1244 (1987). Some of the compounds were claimed to be useful for the asymmetric synthesis of L-Dopa precursors. Sylvain et al., DE3S12781 A1;
- phosphoramidates. Shili et al., Bull. Inst. Chem. Acad. Sin, 41: 9 (1994); Edmundson et al., J. Chem. Res. Synop. 5:122 (1989); and
- phosphonates. Neidlein et al., Heterocycles 35: 1185 (1993).

$N^4$-acyl Prodrugs

The invention also provides $N^4$-acyl prodrugs. A non-limiting example of an $N^4$-acyl derivative of (2'R)-2'-F-2'-C-methylcytidine is shown below:

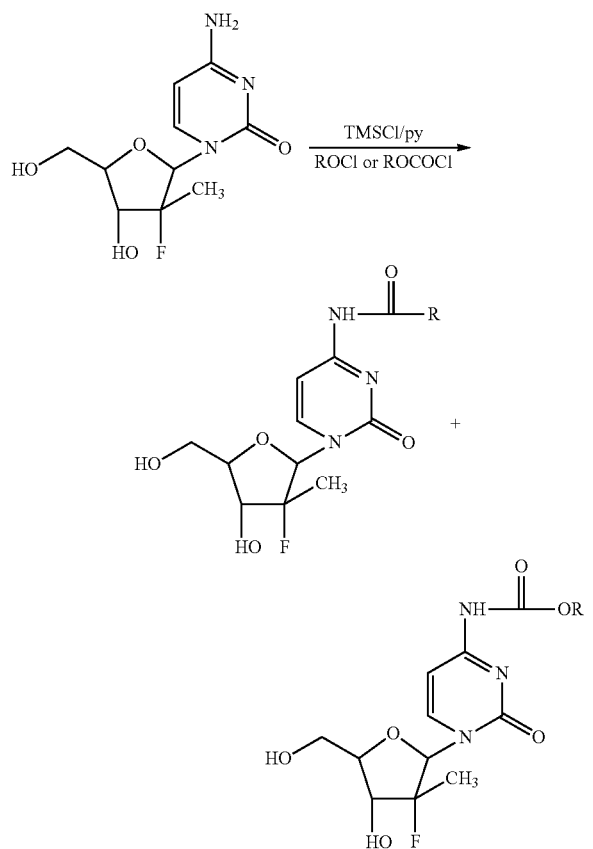

wherein R can be any acyl group as described herein.

The invention also contemplates other embodiments, wherein the prodrug of a (2'R)-2'-deoxy-2'-fluoro-2'-C-methyl nucleoside (β-D or β-L) includes biologically cleavable moieties at the 3' and/or 5' positions. Preferred moieties are natural of synthetic D or L amino acid esters, including D or L-valyl, though preferably L-amino acids esters, such as L-valyl, and alkyl esters including acetyl. Therefore, this invention specifically includes 3'-L or D-amino acid ester and 3',5'-L or D-diamino acid ester of (2'R)-2'-deoxy-2'-fluoro-2'-C-methyl nucleoside (β-D or β-L) nucleosides, preferably L-amino acid, with any desired purine or pyrimidine base, wherein the parent drug optionally has an $EC_{50}$ of less than 15 micromolar, and even more preferably less than 10 micromolar; 3'-(alkyl or aryl) ester or 3',5'-L-di(alkyl or aryl) ester of (2'R)-2'-deoxy-2'-fluoro-2'-C-methyl nucleoside (β-D or β-L) with any desired purine or pyrimidine base, wherein the parent drug optionally has an $EC_{50}$ of less than 10 or 15 micromolar; and prodrugs of 3',5'-diesters of (2'R)-2'-deoxy-2'-fluoro-2'-C-methyl nucleosides (β-D or β-L) wherein (i) the 3' ester is an amino acid ester and the 5'-ester is an alkyl or aryl ester; (ii) both esters are amino acid esters; (iii) both esters are independently alkyl or aryl esters; and (iv) the 3' ester is independently an alkyl or aryl ester and the 5'-ester is an amino acid ester, wherein the parent drug optionally has an $EC_{50}$ of less than 10 or 15 micromolar.

Non-limiting examples of prodrugs falling within the invention are:

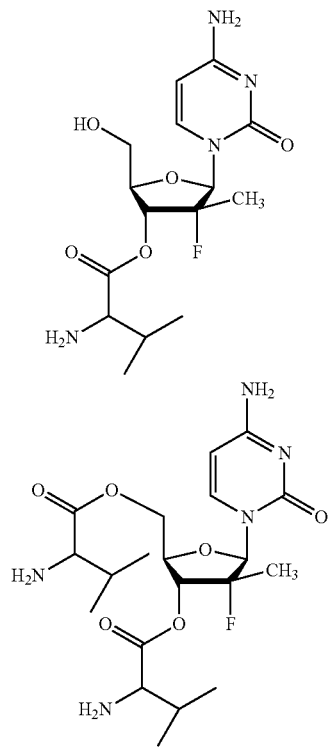

(6) Combination or Alternation Therapy

In another embodiment, for the treatment, inhibition, prevention and/or prophylaxis of any viral infection described herein, the active compound or its derivative or salt can be administered in combination or alternation with another antiviral agent. In general, in combination therapy, effective dosages of two or more agents are administered together, whereas during alternation therapy, an effective dosage of each agent is administered serially. The dosage will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

It has been recognized that drug-resistant variants of flaviviruses, pestiviruses or HCV can emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

For example, one skilled in the art will recognize that any antiviral drug or therapy can be used in combination or alternation with any nucleoside of the present invention. Any of the viral treatments described in the Background of the Invention can be used in combination or alternation with the compounds described in this specification. Nonlimiting examples of the types of antiviral agents or their prodrugs that can be used in combination with the compounds disclosed herein include: interferon, including interferon alpha 2a, interferon alpha 2b, a pegylated interferon, interferon beta, interferon gamma, interferon tau and interferon omega; an interleukin, including interleukin 10 and interleukin 12; ribavirin; interferon alpha or pegylated interferon alpha in combination with ribavirin or levovirin; levovirin; a protease inhibitor including an NS3 inhibitor, a NS3-4A inhibitor; a helicase inhibitor; a polymerase inhibitor including HCV RNA polymerase and NS5B polymerase inhibitor; gliotoxin; an IRES inhibitor; and antisense oligonucleotide; a thiazolidine derivative; a benzanilide, a ribozyme; another nucleoside, nucleoside prodrug or nucleoside derivative; a 1-amino-alkylcyclohexane; an antioxidant including vitamin E; squalene; amantadine; a bile acid; N-(phosphonoacetyl)-L-aspartic acid; a benzenedicarboxamide; polyadenylic acid; a benzimidazoles; thymosin; a beta tubulin inhibitor; a prophylactic vaccine; an immune modulator, an IMPDH inhibitor; silybin-phosphatidylcholine phytosome; and mycophenolate.

Further nonlimiting examples of the types of drugs or their prodrugs described above include: acyclovir (ACV), ganciclovir (GCV or DHPG) and its prodrugs (e.g. valyl-ganciclovir), E-5-(2-bromovinyl)-2'-deoxyuridine (BVDU), (E)-5-vinyl-1-β-D-arabonosyluracil (VaraU), (E) 5-(2-bromovinyl)-1-β-D-arabinosyluracil (BV-araU), 1-(2-deoxy-2-fluoro-β-D-arabinosyl)-5-iodocytosine (D-FIAC), 1-(2-deoxy-2-fluoro-β-L-arabinosyl)-5-methyluracil (L-FMAU, or clevudine), (5)-9-(3-hydroxy-2-phosphonylmethoxypropyl) adenine [(S)-HPMPA], (S)-9-(3-hydroxy-2-phosphonyl-methoxypropyl)-2,6-diaminopurine [(S)-HPMPDAP], (S)-1-(3-hydroxy-2-phosphonyl-methoxypropyl)cytosine [(S)-HPMPC, or cidofivir], and (2S,4S)-1-[2-(hydroxymethyl)-1,3-dioxolan-4-yl]-5-iodouracil (L-5-IoddU), entecavir, lamivudine (3TC), LdT, LdC, tenofovir, and adefovir, the (−)-enantiomer of 2-hydroxymethyl-5-(5-fluorocytosin-1-yl)-1,3-oxathiolane ((−)-FTC); the (−)-enantiomer of 2-hydroxymethyl-5-(cytosin-1-yl)-1,3-oxathiolane (3TC); carbovir, acyclovir, famciclovir, penciclovir, AZT, DDI, DDC, L-(−)-FMAU, D4T, amdoxovir, Reverset, Racivir, abacavir, L-DDA phosphate prodrugs, and β-D-dioxolanyl-6-chloropurine (ACP), non-nucleoside RT inhibitors such as nevirapine, MKC-442, DMP-226 (sustiva), protease inhibitors such as indinavir, saquinavir, Kaletra, atazanavir; and anti-HIV compounds such as BILN-2061, ISIS 14803; viramidine, NM 283, VX-497, JKT-003, levovirin, isatoribine, albuferon, Peg-infergen, VX-950, R803, HCV-086, R1479 and DMP45.

Pharmaceutical Compositions

Hosts, including humans, infected with pestivirus, flavivirus, HCV infection, or any other condition described herein, or another organism replicating through a RNA-dependent RNA viral polymerase, or for treating any other disorder described herein, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for a Flaviviridae infection, including hepatitis C virus, West Nile Virus and yellow fever virus and rhinovirus infection will be in the range from about 50 to about 2000 mg one to four times per day. Lower doses may be useful, and thus ranges can include from 50-1, 000 mg one to four times per day. The effective dosage range of the pharmaceutically acceptable salts and prodrugs can be calculated based on the weight of the parent nucleoside to be delivered. If the salt or prodrug exhibits activity in itself the effective dosage can be estimated as above using the weight of the salt or prodrug, or by other means known to those skilled in the art.

The compound is conveniently administered in unit any suitable dosage form, including but not limited to one containing 25 to 3000 mg, preferably 50 to 2000 mg of active ingredient per unit dosage form. An oral dosage of 50-1000 mg is usually convenient, including in one or multiple dosage forms of 50, 100, 200, 250, 300, 400, 500, 600, 700, 800, 900 or 1000 mgs. Also contemplated are doses of 0.1-50 mg, or 0.1-20 mg or 0.1-10.0 mg. Furthermore, lower doses may be utilized in the case of administration by a non-oral route, as, for example, by injection or inhalation.

Ideally the active ingredient should be administered to achieve peak plasma concentrations ($C_{max}$) of the active compound of from about 5.0 to 70 µM, preferably about 5.0 to 15 µM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

(7) Biological Methods

Antiviral Testing of Candidate Compounds with HCV Replicon System in Huh7 Cells.

Huh7 cells harboring the HCV replicon can be cultivated in DMEM media (high glucose, no pyruvate) containing 10% fetal bovine serum, 1× non-essential Amino Acids, Pen-Strep-Glu (100 units/liter, 100 microgram/liter, and 2.92 mg/liter, respectively) and 500 to 1000 microgram/milliliter G418. Antiviral screening assays can be done in the same media without G418 as follows: in order to keep cells in logarithmic growth phase, cells are seeded in a 96-well plate at low density, for example 1000 cells per well. The test compound is added immediately after seeding the cells and incubate for a period of 3 to 7 days at 37° C. in an incubator. Media is then removed, and the cells are prepared for total nucleic acid extraction (including replicon RNA and host RNA). Replicon RNA can then be amplified in a Q-RT-PCR protocol, and quantified accordingly. The observed differences in replicon HCV RNA levels compared to the untreated control is one way to express the antiviral potency of the test compound.

In another typical setting, a compound might reduce the viral RNA polymerase activity, but not the host RNA polymerase activity. Therefore, quantification of rRNA or beta-actin mRNA (or any other host RNA fragment) and comparison with RNA levels of the no-drug control is a relative measurement of the inhibitory effect of the test compound on cellular RNA polymerases.

Phosphorylation Assay of Nucleoside to Active Triphosphate

To determine the cellular metabolism of the compounds, Huh-7 cells are obtained from the American Type Culture Collection (Rockville, Md.), and are grown in 225 cm² tissue culture flasks in minimal essential medium supplemented with non-essential amino acids, 1% penicillin-streptomycin. The medium is renewed every three days, and the cells are sub cultured once a week. After detachment of the adherent monolayer with a 10 minute exposure to 30 mL of trypsin-EDTA and three consecutive washes with medium, confluent Huh-7 cells are seeded at a density of $2.5 \times 10^6$ cells per well in a 6-well plate and exposed to 10 µM of [$^3$H] labeled active compound (500 dpm/µmol) for the specified time periods. The cells are maintained at 37° C. under a 5% $CO_2$ atmosphere. At the selected time points, the cells are washed three times with ice-cold phosphate-buffered saline (PBS). Intracellular active compound and its respective metabolites are extracted by incubating the cell pellet overnight at −20° C. with 60% methanol followed by extraction with an additional 20 µL of cold methanol for one hour in an ice bath. The extracts are then combined, dried under gentle filtered air flow and stored at −20° C. until HPLC analysis.

Bioavailability Assay in Cynomolgus Monkeys

Within 1 week prior to the study initiation, the cynomolgus monkey is surgically implanted with a chronic venous catheter and subcutaneous venous access port (VAP) to facilitate blood collection and underwent a physical examination including hematology and serum chemistry evaluations and the body weight was recorded. Each monkey (six total) receives approximately 250 µCi of $^3$H-labeled compound combined with each dose of active compound at a dose level of 10 mg/kg at a dose concentration of 5 mg/mL, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. Blood samples are collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples are analyzed for the maximum concentration ($C_{max}$), time when the maximum concentration is achieved ($T_{max}$), area under the curve (AUC), half life of the dosage concentration ($T_{1/2}$), clearance (CL), steady state volume and distribution ($V_{ss}$) and bioavailability (F).

Bone Marrow Toxicity Assay

Human bone marrow cells are collected from normal healthy volunteers and the mononuclear population are separated by Ficoll-Hypaque gradient centrifugation as described previously by Sommadossi J-P, Carlisle R. "Toxicity of 3'-azido-3'-deoxythymidine and 9-(1,3-dihydroxy-2-propoxymethyl)guanine for normal human hematopoietic progenitor cells in vitro" Antimicrobial Agents and Chemotherapy 1987; 31:452-454; and Sommadossi J-P, Schinazi R F, Chu C K, Xie M-Y. "Comparison of cytotoxicity of the (−)- and (+)-enantiomer of 2',3'-dideoxy-3'-thiacytidine in normal human bone marrow progenitor cells" Biochemical Pharmacology 1992; 44:1921-1925. The culture assays for CFU-GM and BFU-E are performed using a bilayer soft agar or methylcellulose method. Drugs are diluted in tissue culture medium and filtered. After 14 to 18 days at 37° C. in a humidified atmosphere of 5% $CO_2$ in air, colonies of greater than 50 cells are counted using an inverted microscope. The results are presented as the percent inhibition of colony formation in the presence of drug compared to solvent control cultures.

Mitochondria Toxicity Assay

Fifty microliters of 2× drug dilutions were added per well in a 96 well plate. A "no drug" (media only) control was used to determine maximum amount of mitochondrial DNA produced and ribosomal DNA. 3TC @ 10 µM was used as a negative control, and ddC @10 µM was used as a toxic control. Ribosomal DNA levels were used to determine specific toxicicity to mitochondria or generally cytotoxicity. HepG2 cells (5,000 cells/well at 50 µl) were added to the plate. The plate was incubated at 37° C. in a humidified 5% $CO_2$ atmosphere for 7 days. After incubation, the supernatant was removed and stored for lactic acid quantification, and total DNA was extracted from cells as described in the RNeasy 96 handbook (February 1999), pages 22-23. No DNA digestions were performed, therefore total RNA and DNA were extracted.

The extracted DNA was amplified and the change in mitochondrial DNA and ribosomal DNA for each sample was determined. The fold difference in mitochondrial DNA normalized for ribosomal DNA relative to control was calculated.

Lactic acid quantification was performed by the D-Lactic Acid/L-Lactic acid test kit (Boehringer Mannheim/R-Biopharm/Roche). The total amount of lactic acid produced for each sample was found as well as the fold change in lactic acid production (% of lactic acid/% of rDNA) as described in the manufacturers instructions.

Cytotoxicity Assay

50 µl of 2× drug dilutions were added per well in a 96 well plate. Final concentrations of drug ranged from 1 to 100 µM. A "no drug" (media only) control was used to determine the minimum absorbance values and a "cells+media only" control was used for maximum absorbance value. A solvent control was also used. Cells were then added (PBM: $5\times10^4$ cells/well; CEM: $2.5\times10^3$ cells/well; Vero, HepG2, Huh-7, and Clone A: $5\times10^3$ cells/well) and incubated at 37° C. in a humidified 5% $CO_2$ atmosphere for 3-5 days (PBM: 5 days; CEM: 3 days, all others: 4 days). After incubation, 20 µl of MTS dye was added from Cell Titer Aqueous One Solution Cell Proliferation Assay to each well and the plate was re-incubated for 2-4 hours. The absorbance (490 nm) was then read on an ELISA plate reader using the media only/no cell wells as blanks. Percent inhibition was found and used to calculate the $CC_{50}$.

In Vivo Toxicity in Mice

In vivo toxicity was also determined following injections into female Swiss mice of the various nucleosides disclosed in the present invention. Intraperitoneal injections were given on days 0, day 1, day 2, day 3, and day 5 of varying doses of the particular nucleoside. Separate animals were injected with vehicle as control groups. In these studies, each dosing group contained 5-10 mice. The average weight change in each of the mice was measured as a sign of toxicity of the compound.

(BVDV) Yield Reduction Assay

Madin-Darby Bovine Kidney (MDBK) cells were grown in Dulbecco's modified eagle medium supplemented with 10% horse serum and 100n/ml penicillin-streptomycin. Cells were seeded in a 96-well plate at $5\times10^3$ cells/well and incubated for 72 h at 37° C. in a humidified 5% $CO_2$ atmosphere. Cells were infected with either cytopathic (NADL strain) or noncytopathic (SD-1 strain) BVDV at a virus dilution of $10^{-2}$ and incubated for 45 min. Cell monolayers were washed three times with medium. Fresh medium-containing test compounds in dose response concentrations or ribavirn, as a positive control, were added to cultures and medium containing no drug was added to the no-drug controls. After 72 h incubation, supernatant was collected and viral RNA was extracted using the QIAmp Viral RNA Mini Kit (Qiagen, Calif.). Viral load was determined by Q-RT-PCR using primers specific for either NADL or SD-1 (1).

(8) Synthetic Protocol

The following non-limiting embodiments illustrate some general methodologies to obtain the nucleosides of the present invention. Two representative general methods for the preparation of compounds of the present invention are outlined in Schemes 1 and 2 while more specific examples of these general methods are provided in Scheme 3 (Example 1), Scheme 4 (Example 2), Scheme 5 (Example 3), and Scheme 6 (Example 4). Scheme 1 represents a generalized process starting from a (2R) 2-deoxy-2-methyl-2-fluoro-carbohydrate and forms the nucleosides of the present invention by condensing with a nucleobase. Scheme 2 starts from a preformed, purine or pyrimidine nucleoside, optionally substituted at C-4' and constructs the C-2' (R) methyl, fluoro nucleosides of the present invention. While these schemes illustrate the syntheses of compounds of the present invention of general formulas (I) and (II) wherein there is a furanose ring in the β-D-ribo configuration, this is not intended to be a limitation on the scope of the process invention in any way, and they should not be so construed. Those skilled in the art of nucleoside and nucleotide synthesis will readily appreciate that known variations of the conditions and processes of the following preparative procedures and known manipulations of the nucleobase can be used to prepare these and other compounds of the present invention. Additionally, the L-enantiomers corresponding to the compounds of the invention can be prepared following the same methods, beginning with the corresponding L-carbohydrate building block or nucleoside L-enantiomer as the starting material.

1. Glycosylation of the Nucleobase with an Appropriately Modified Sugar

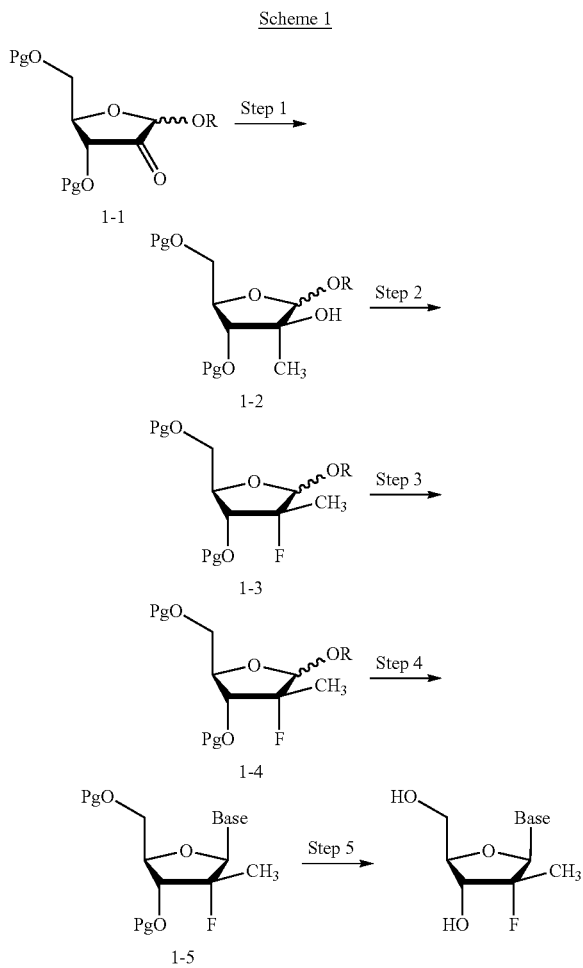

Pg = Protecting group
R = Lower alkyl, acyl, mesyl, benzoyl.
Base = as defined herein.

Step 1 in Scheme 1 introduces the 2-methyl group by using an appropriate alkylating agent such as methyllithium, trimethylaluminum, or methylmagnesium bromide in an anhydrous solvent such as tetrahydrofuran (THF), chloroform, or diethyl ether. Compounds 1-1 through 1-4 can be purely α or β or they may exist as an anomeric mixture containing both α and β anomers in any ratio. However, the preferred anomeric configuration of structure 1-1 is β.

Step 2 introduces the fluorine atom at the 2-position of the alkyl furanoside. This can be achieved by treatment of the tertiary alcohol, 1-2, with a commercially available fluorinating reagent such as (diethylamino)sulfur trifluoride (DAST) or Deoxofluor in an anhydrous, aprotic solvent such as tetrahydrofuran, chloroform, dichloromethane, or toluene. Preferably the stereochemistry proceeds with inversion of configuration at C-2. That is, starting from a C-2 hydroxyl "up" (or arabinofuranoside) in structure 1-2, the C-2 fluorine is "down" in the intermediate ribofuranoside 1-3.

In step 3, the optional protecting groups (Pg) can be deprotected and reprotected to groups more suitable for the remaining manipulations (T. W. Greene and P. G. M. Wuts, "Protective Groups in Organic Synthesis," 3rd ed., John Wiley & Sons, 1999). For example, benzyl ethers (Bn) may be difficult to remove in the protected nucleoside, 1-5 and may be deprotected and replaced with a group more facile to remove from the nucleoside of structural type 1-5. Furthermore, the anomeric position (C-1) can also be optionally manipulated to a suitable group for the coupling reaction with the nucleobase (step 4). Several methods for anomeric manipulations are established to those skilled in the art of nucleoside synthesis. Some non-limiting examples by treatment of the alkyl furanoside (1-3, R=alkyl) with a mixture of acetic anhydride, acetic acid, and a catalytic amount of sulfuric acid (acetolysis) to provide structure 1-4 where R=Ac, with optional protecting groups. Also, the alkyl group in 1-3 may be converted to an acetate, benzoate, mesylate, tosylate, triflate, or tosylate, for example, by first hydrolyzing the 1-Oalkyl group to a 1-hydroxyl group by using a mineral acid consisting of but not limited to sulfuric acid, hydrochloric acid, and hydrobromic acid or an organic acid consisting of but not limited to trifluoroacetic acid, acetic acid, and formic acid (at ambient temperature or elevated temperature). The reducing sugar could then be converted to the desired carbohydrate by treatment with acetyl chloride, acetic anhydride, benzyol chloride, benzoic anhydride, methanesulfonyl chloride, triflic anhydride, trifyl chloride, or tosyl chloride in the presence of a suitable base such as triethylamine, pyridine, or dimethylaminopyridine.

The nucleosidic linkage is constructed by treatment of intermediate 1-3 or 1-4 with the appropriate persilylated nucleobase in the presence of a lewis acid such as tin tetrachloride, titanium tetrachloride, trimethylsilyltriflate, or a mercury (II) reagent (HgO/HgBr$_2$) usually at an elevated temperature in an aprotic solvent such as toluene, acetonitrile, benzene, or a mixture of any or all of these solvents.

The optional protecting groups in the protected nucleosides or structural formula 1-5 can be cleaved following established deprotection methodologies (T. W. Greene and P. G. M. Wuts, "Protective Groups in Organic Synthesis," 3rd ed., John Wiley & Sons, 1999).

2. Modification of a Pre Formed Nucleoside

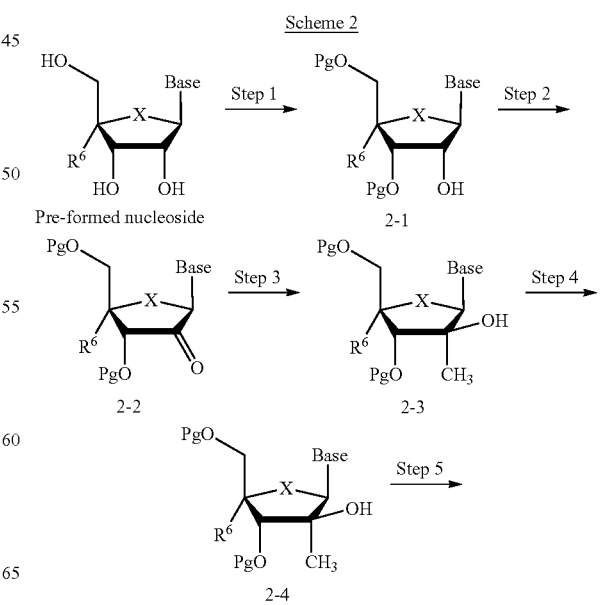

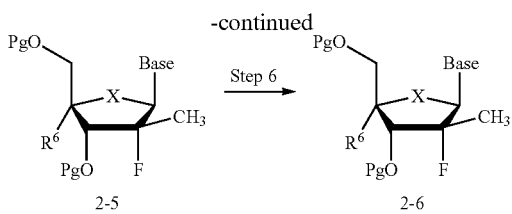

Pg = Protecting group
Base = as defined herein (optionally protected)
X = as defined herein
R[6] = as defined herein The starting material for this process is an appropriately substituted purine or pyrimidine nucleoside with a 2'-OH and 2'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by T. W. Greene and P. G. M. Wuts, "Protective Groups in Organic Synthesis," 3rd ed., John Wiley & Sons, 1999.

The purine or pyrimidine nucleoside can then be oxidized at the 2'-position with the appropriate oxidizing agent in a compatible solvent at a suitable temperature to yield the 2'-modified nucleoside. Possible oxidizing agents are a mixture of dimethylsulfoxide, trifluoroacetic anhydride or acetic anhydride (a Swern/Moffat oxidation), chromium trioxide or other chromate reagent, Dess-Martin periodinane, or by ruthenium tetroxide/sodium periodate.

The optionally protected nucleoside 2'-ketone is then alkylated using such alkylating agents methyllithium, trimethylaluminum, methylmagnesium bromide, or similar reagents in an anhydrous solvent such tetrahydrofuran (THF), chloroform, or diethyl ether usually at temperatures below 0° C. Compounds of the structural formula 2-3 are preferred to have the 2'(S) or 2'-methyl "down", 2'-OH "up" configuration.

The nucleoside of structure 2-3 can be deprotected and reprotected with a number of protecting groups such as an O-acyl (alkyl or aryl), O-sulfonyl, or an N-acyl (alkyl or aryl) for the base. This optional reprotection step need not be limited to protecting groups that function as chemical protecting groups. Other protecting groups such as long chain acyl groups of between 6 and 18 carbon units or amino acids can be introduced independently on the nucleobase or the sugar. The protecting groups can serve as prodrugs of the active substance.

Step 5 introduces the fluorine atom at the 2' position of the pre-formed nucleoside. This can be achieved by treatment of the tertiary alcohol, 2-4, with a commercially available fluorinating reagent such as (diethylamino)sulfur trifluoride (DAST) or Deoxofluor in an anhydrous, aprotic solvent such as tetrahydrofuran, chloroform, dichloromethane, or toluene. Preferably the stereochemistry proceeds with inversion of configuration at the 2' position. That is, starting from a C-2' hydroxyl "up" (or arabinonucleoside) in structure 2-4, the C-2' flourine is "down" in the intermediate nucleoside 2-5. The absolute configuration of a nucleoside of structure 2-4 is (2'S) while the absolute configuration of a nucleoside of structure 2-5 is (2'R).

Subsequently, the nucleosides of structural type 2-5 can be deprotected by methods well known to those skilled in the art, as taught by T. W. Greene and P. G. M. Wuts, "Protective Groups in Organic Synthesis," 3rd ed., John Wiley & Sons, 1999.

The following working examples provide a further understanding of the method of the present invention and further exemplify the general examples in Schemes 1 and 2 above. These examples are of illustrative purposes, and are not meant to limit the scope of the invention. Equivalent, similar or suitable solvents, reagents or reaction conditions may be substituted for those particular solvents, reagents or reaction conditions described without departing from the general scope of the method.

EXAMPLES

Example 1

Synthesis of (2'R)-2'-Deoxy-2'-Fluoro-2'-C-Methyl-cytidine Starting from a Carbohydrate

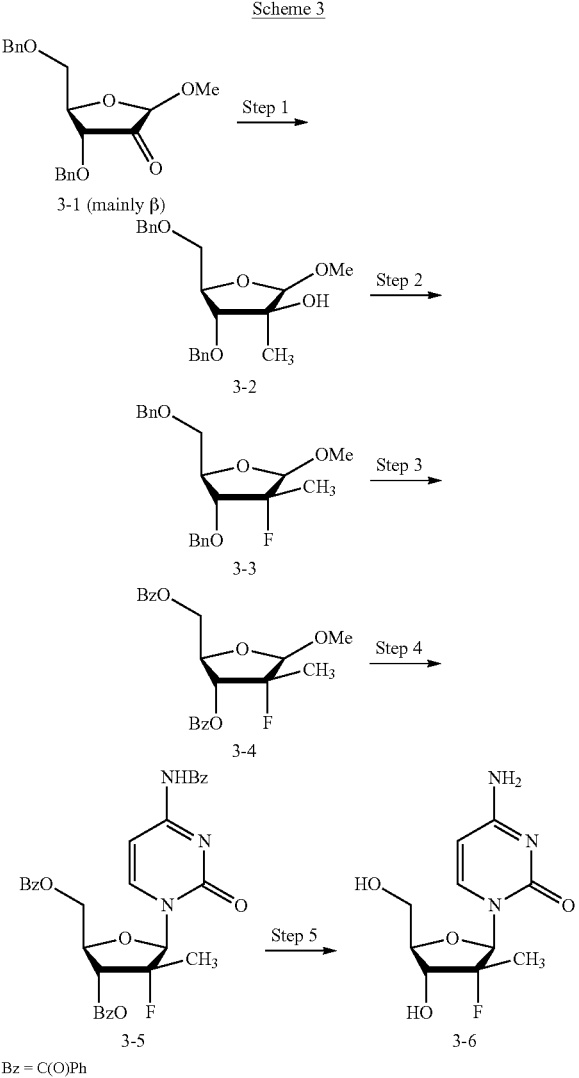

Bz = C(O)Ph
Bn = CH$_2$Ph

Step 1: Compound 3-1 (7.7 g, 0.022 mmol) was dissolved in anhydrous diethyl ether and cooled to −78° C. To this solution was added MeLi (30 mL, 1.6 M in diethyl ether). After the reaction was complete, the mixture was treated with ammonium chloride (1 M, 65 mL) and the organic phase was separated, dried (Na$_2$SO$_4$), filtered, and concentrated to dryness. Silica gel chromatography followed by crystallization from diethyl ether-hexanes afforded pure compound 3-2 (6.31 g). $^1$H NMR (400 MHz, CDCl$_3$): δ 1.40 (s, 3H), 3.41 (s, 3H), 3.49 (dd, 1H, J=10.3, 6.89 Hz), 3.57 (dd, 1H, J=10.3, 3.88 Hz), 3.84 (d, 1H, J=7.3 Hz), 4.03 (m, 1H), 4.48 (s, 1H), 4.58 (m, 3H), 4.83 (d, 1H, J=11.6 Hz), 7.31-7.36 (m, 10H); $^{13}$C NMR (100 MHz, CDCl$_3$): 18.4, 55.4, 72.2, 73.4, 79.5, 80.2, 84.7, 107.4, 127.7, 127.8, 127.83, 128.5, 138.2, 138.3.

Step 2: Compound 3-2 was dissolved in CH$_2$Cl$_2$ and was treated with DAST (4.0 mL, 30.3 mmol) at room temperature. The solution was stirred at room temp overnight. The so-obtained mixture was poured into sat NaHCO$_3$ (100 mL) and washed with sat NaHCO$_3$ (1×15 mL). The organic layer was further worked up in the usual manner. Silica gel chromatography (1:5 EtOAc-hexanes) gave crude compound 3-3 (0.671 g) that was sufficiently pure for the next step. $^1$H NMR (400 MHz, CDCl$_3$): δ 1.43 (d, 3H, J=22.8 Hz), 3.35 (s, 3H), 3.49 (dd, 1H, J=10.5, 5.4 Hz), 3.55 (dd, 1H, J=10.5, 4.1 Hz), 3.87 (dd, 1H, J=23.5, 7.5 Hz), 4.26 (m, 1H), 4.56 (d, 2H, J=6.9 Hz), 4.66 (d, 2H, J=8.2 Hz), 4.72 (d, 1H, J=10.8 Hz), 7.29-7.36 (m, 10H); $^{13}$C NMR (100 MHz, CDCl$_3$): δ 17.0 (d, J=24.4 Hz), 55.2 77.1, 73.4, 73.8, 77.3, 80.3, 81.2 (d, J=16 Hz), 99.7 (d, J=178.9 Hz), 106.8 (d, J=32.0 Hz), 127.7, 127.8, 128.1, 128.3, 128.5, 128.6, 137.8, 138.3; $^{19}$F NMR (100 MHz, CDCl$_3$): δ −8.2 (m, 1F).

Step 3: Compound 3-3 (0.39 g, 1.1 mmol) was dissolved in 1:2 EtOH-EtOAc and treated with Pd/C (~0.1 g) and cyclohexene (~1 mL). The mixture was heated to reflux overnight and then filtered through celite. The solvent was removed in vacuo and the residue was dissolved in pyridine (~5 mL). To this solution was added benzoyl chloride (0.22 mL, 1.83 mmol) and the mixture was stirred at room temp overnight. The pyridine was removed in vacuo and the residue was partitioned between CH$_2$Cl$_2$ and sat NaHCO$_3$ (10.0 mL). The organic phase was dried (Na$_2$SO$_4$), filtered, and the solution was concentrated to dryness. Column chromatography provided 0.350 g of pure compound 3-4. $^1$H NMR (400 MHz, CDCl$_3$): δ 1.53 (d, 3H, J=22.4 Hz), 3.39 (s, 3H), 4.46 (dd, 1H, J=11.6, 4.7 Hz), 4.58 (m, 1H), 4.65 (dd, 1H, J=11.6, 3.9 Hz), 4.87 (d, 1H, J=9.9 Hz), 5.64 (dd, 2H, J=24.1, 7.8 Hz), 7.29-7.36 (m, 10H); $^{19}$F NMR (100 MHz, CDCl$_3$): δ −7.5 (m, 1F).

Step 4: A solution of bis(trimethylsilyl)-N-benzoylcytosine (0.28 g, 0.77 mmol) and compound 3-4 (0.20 g, 0.5 mmol) in 1,2 dichloroethane (2 mL) and toluene (2 mL) was treated with TMSOTf (0.15 mL, 0.77 mmol). After most of the starting material disappeared as judged by TLC, the solution was cooled to room temp, washed with water (1×5 mL), brine (1×5 mL), dried (Na$_2$SO$_4$), filtered, and concentrated to dryness. Flash chromatography followed by crystallization from CH$_2$Cl$_2$-hexanes afforded compound 3-5 (68 mg). mp 241° C.; $^1$H NMR (400 MHz, CDCl$_3$): δ 1.49 (d, 3H, J=22.4 Hz), 4.64 (dd, 1H, J=12.9, 3.4 Hz), 4.73 (app d, 1H, J=9.5 Hz), 4.89 (dd, 1H, J=12.7, 2.2 Hz), 5.56 (dd, 1H, J=20.7, 8.6 Hz), 6.52 (d, 1H, J=15.9 Hz), 7.38-7.67 (m, 10H), 7.89 (d, 2H, J=6.9 Hz), 8.07-8.11 (m, 5H), 8.67 (s, 1H); $^{19}$F NMR (100 MHz, CDCl$_3$): δ 2.85 (m, 1F).

Step 5: Compound 3-5 (40 mg, 0.05 mmol) was dissolved in methanolic ammonia and stirred at room temp for 48 h. The solution was concentrated to dryness and chromatographed (SiO$_2$) eluting with 1:4 EtOH—CH$_2$Cl$_2$. The yield was about 12 mg of pure (2'R)-2'-deoxy-2'-fluoro-2'-C-methylcytidine, 3-6. $^1$H NMR (400 MHz, DMSO-d$_6$): δ 1.16 (d, 3H, J=22.0 Hz), 3.61 (dd, 1H, J=11.6, 5.2 Hz), 3.60-3.83 (m, 3H, J=10.5, 5.4 Hz), 5.24 (s, 1H, exchangeable with D$_2$O), 5.59 (s, 1H, exchangeable with D$_2$O), 5.71 (d, 1H, J=7.3 Hz), 6.08 (d, 1H, J=19.0 Hz), 7.24 (d, 1H, J=17.7 Hz, exchangeable with D$_2$O), 7.87 (d, 1H); $^{19}$F NMR (100 MHz, DMSO-d$_6$): δ 4.13 (m, 1F).

Example 2

Synthesis of (2'R)-2'-Deoxy-2'-Fluoro-2'-C-Methyl-cytidine Starting from Cytidine

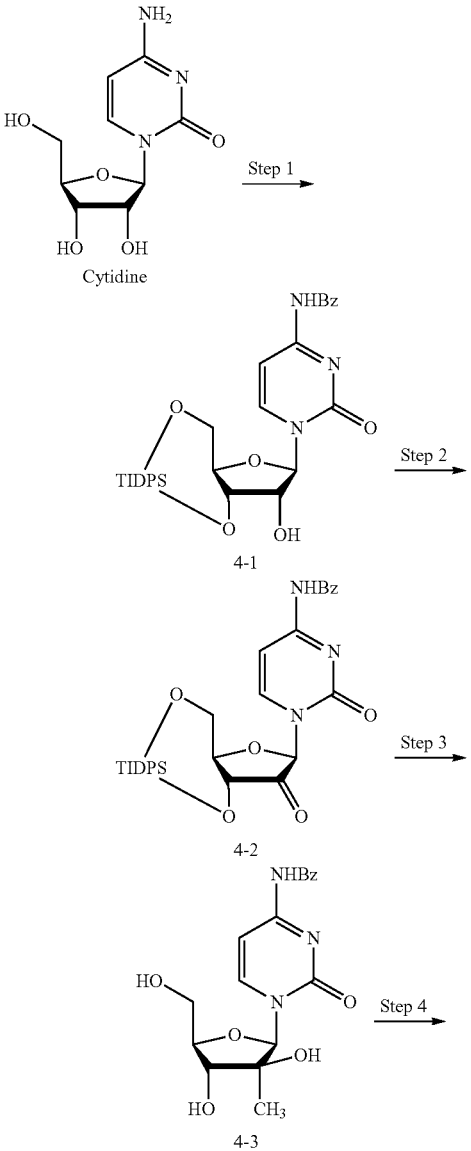

Scheme 4

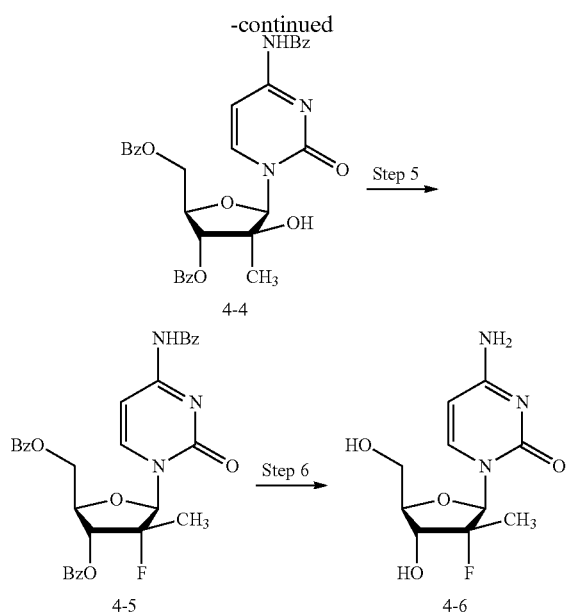

TIDPS = 1,3-(1,1,3,3-Tetraisopropyldisiloxanylidene)

Step 1: To a suspension of cytidine (100 g, 0.411 mol) in DMF (2.06 L) is added benzoic anhydride (102.4 g, 0.452 mol). The mixture was stirred at room temperature for 20 h. The DMF was removed in vacuo and the residue was triturated with diethyl ether. The resulting solid was collected by suction filtration and washed with diethyl ether (2×200 mL). Further drying in vacuo at room temperature gave the $N^4$ benzamide (140.6 g, 983%). A portion of this material (139.3 g, 0.401 mol) was dissolved in anhydrous pyridine (1.2 L) and was treated with 1,3-dichloro-1,1,3,3-tetraisopropyl-disiloxane (141.4 mL, 0.441 mol) at room temp. The solution was stirred at room temperature overnight. The mixture was concentrated to near dryness in vacuo and coevaporated with toluene (3×200 mL). The residue was treated with EtOAc (1.8 L) and washed with HCl (2×200 mL, 0.05 N), NaHCO$_3$ (5%, 2×400 mL). The organic layer was washed dried (Na$_2$SO$_4$), filtered, and evaporated to dryness. Compound 4-1 (256.5 g, >100%) was isolated as a white foam and used without further purification.

Step 2: Compound 4-1 (236.5 g, 0.40 mol) was dissolved in dry THF (1.22 L). Anhydrous dmso (180.8 mL, 2.1 mol) was added and the resulting solution was cooled to between −20° C. and −15° C. Trifluoroacetic anhydride (90.6 mL, 0.64 mol) was added dropwise over 45 minutes and the solution was stirred between −20° C. and −15° C. for 2 hrs after which anhydrous triethylamine (223.5 mL, 1.6 mol) was added over 20 min. The crude reaction containing ketone 4-2 was dissolved in EtOAc (500 mL), and the resulting solution was washed with H$_2$O (3×400 mL), dried (Na$_2$SO$_4$) and the solvents were removed in vacuo to give a yellow solid that was purified on a silica gel column eluting with a stepwise gradient of Et$_2$O (0-60%) in hexanes followed by a stepwise gradient of EtOAc (50-100%) in hexanes. The crude ketone so-obtained (~192 g) was crystallized from petroleum ether to give ketone 4-2 (138.91 g, 57.5% from cytidine) as a white solid and 22 g of unreacted starting material, 4-1, as a yellow solid.

Step 3: Compound 4-2 (48.57 g, 8.26 mmol) was dissolved in anhydrous toluene (~400 mL) and the solvent was removed in vacuo with exclusion of moisture. The residue was then further dried in vacuo (oil pump) for another 2 h. With strict exclusion of moisture, the residual foam was dissolved in anhydrous diethyl ether (1.03 L) under argon. The resulting solution was cooled to −78° C. under argon and MeLi (1.6 M, 258.0 mL, 0.413 mol) was added dropwise via additional funnel. After the addition was complete, the mixture was stirred for 2 h at −78° C. Aqueous 1 M NH$_4$Cl (500 mL) was added slowly. After warming to room temperature, the mixture was washed with H$_2$O (2×500 mL), dried (Na$_2$SO$_4$), and then concentrated to dryness to give a brown foam (~60 g, >100%).

The reaction was performed two more times using 37.62 g and 56.4 g of compound 4-2. The combined crude products (128.0 g, 0.212 mol) were dissolved in THF (1.28 L) and treated with concd HOAc (23 mL, 0.402 mol). To the solution was added TBAF (384.0 mL, 1 M in THF). The solution was stirred at room temp for 0.75 h and the mixture was treated with silica gel (750 g) and concentrated to dryness. The powder was placed on a silica gel column packed in CH$_2$Cl$_2$. Elution with 1:7 EtOH—CH$_2$Cl$_2$ afforded a dark waxy solid that was pre-adsorbed on silica gel (300 g) and chromatographed as before. Compound 4-3 (46.4 g, 53.0% from 4-2) was isolated as an off-white solid. $^1$H NMR (DMSO-d$_6$): δ 1.20 (s, 3H, CH$_3$), 3.62-3.69 (m, 2H,), 3.73-3.78 (m, 2H,), 5.19 (t, 1H, J=5.4 Hz, OH-5'), 5.25 (s, 1H, OH-2'), 5.52 (d, 1H, J=5.0 Hz, OH-3'), 5.99 (s, 1H, H-1'), 7.32 (d, 1H, J=5.8 Hz), 7.50 (Ψt, 2H, J=7.7 Hz), 7.62 (Ψt, 1H, J=7.3 Hz), 8.00 (d, 2H, J=7.3 Hz), 8.14 (d, 1H, J=6.9 Hz), 11.22 (s, 1H, NH). Anal. Calcd for C$_{17}$H$_{19}$N$_3$O$_6$.0.5 H$_2$O: C, 55.13; H, 5.44; N, 11.35. Found: C, 55.21; H, 5.47; N, 11.33.

Step 4: Compound 4-3 (46.0 g, 0.13 mol) was dissolved in anhydrous pyridine and concentrated to dryness in vacuo. The resulting syrup was dissolved in anhydrous pyridine under argon and cooled to 0° C. with stirring. The brown solution was treated with benzoyl chloride (30 mL, 0.250 mol) dropwise over 10 min. The ice bath was removed and stirring continued for 1.5 h whereby TLC showed no remaining starting material. The mixture was quenched by the addition of water (5 mL) and concentrated to dryness. The residue was dissolved in a minimal amount of CH$_2$Cl$_2$ and washed with satd NaHCO$_3$ (1×500 mL) and H$_2$O (1×500 mL). The organic phase was dried (Na$_2$SO$_4$) and filtered, concentrated to dryness and chromatographed on silica gel eluting with a stepwise gradient of EtOAc-hexanes (25-60%) to provide compound 4-4 as yellow foam (48.5 g, 67%). $^1$H NMR (CDCl$_3$): δ 1.64 (s, 3H, CH$_3$), 4.50 (m, 1H, H-4), 4.78-4.85 (m, 2H, H-5',5a'), 5.50 (d, 1H, J=3.4 Hz, H-3'), 6.42 (s, 1H, H-1'), 7.44-7.54 (m, 7H, Ar), 7.57-7.66 (m, 3H, Ar), 7.94 (d, 2H, J=7.8 Hz), 8.05-8.09 (m, 4H, Ar), 8.21 (d, 1H, J=7.3 Hz). Anal. Calcd for C$_{31}$H$_{27}$N$_3$O$_8$: C, 65.37; H, 4.78; N, 7.38. Found: C, 65.59; H, 4.79; N, 7.16.

Step 5: Compound 4-4 (7.50 g, 0.013 mol) was dissolved in anhydrous toluene (150 mL) under argon and cooled to −20° C. DAST (2.5 mL, 18.9 mmol) was added slowly and the cooling bath was removed after the addition was complete. Stirring was continued for 1 h and the mixture was poured into satd NaHCO$_3$ (100 mL) and washed until gas evolution ceased. The organic phase was dried (Na$_2$SO$_4$), concentrated, and purified by silica gel chromatography eluting with 1:1 EtOAc-hexanes. Yield was 1.22 g (16.3%) of pure 4-5 as a white solid. mp 241° C. (CH$_2$Cl$_2$-hexanes); $^1$H NMR (CDCl$_3$): δ 1.49 (d, 3H, J=22.4 Hz, CH$_3$), 4.64 (dd, 1H, J=3.44, 12.9 Hz, H-5'), 4.73 (d, 1H, J=9.5 Hz, H-4'), 4.90 (dd, 1H, J=2.4, 12.7 Hz, H-5a'), 5.56 (dd, 1H, J=8.6, 20.7 Hz, H-3'), 6.52 (d, 1H, J=18.0 Hz, H-1'), 7.47-7.57 (m, 7H, Ar), 7.62-7.71 (m, 3H, Ar), 7.89 (d, 2H, J=6.9 Hz), 8.07-8.11 (m, 5H, Ar), 8.67 (bs, 1H, NH). $^{19}$F NMR (CDCl$_3$): δ 3.3 (m).

Anal. Calcd for $C_{31}H_{26}FN_3O_7 \cdot 0.7 H_2O$: C, 63.74; H, 4.72; N, 7.20. Found: C, 63.71; H, 4.54; N, 7.20.

Step 6: Compound 4-5 (6.30 g, 0.011 mol) was suspended in methanolic ammonia (ca 7 N, 150 mL) and stirred at room temperature overnight. The solvent was removed in vacuo, co-evaporated with methanol (1×20 mL), and pre-adsorbed onto silica gel. The white powder was placed onto a silica gel column (packed in $CHCl_3$) and the column was eluted with 9% EtOH in $CHCl_3$, then 17% EtOH and finally 25% EtOH in $CHCl_3$. Concentration of the fractions containing the product, filtration through a 0.4 μm disk, and lyophillization from water afforded compound 4-6, 2.18 g (76%). $^1$H NMR (DMSO-$d_6$): δ 1.17 (d, 3H, J=22.3 Hz, $CH_3$), 3.63 (dd, 1H, J=2.7, 13.7 Hz, H-5'), 3.70-3.84 (m, 3H, H-3', H-4', H-5a'), 5.24 (app s, 1H, OH-3'), 5.60 (d, 1H, J=5.4 Hz, H-5'), 5.74 (d, 1H, J=7.71 Hz, H-5), 6.07 (d, 1H, J=18.9 Hz, H-1'), 7.31 (s, 1H, $NH_2$), 7.42 (s, 1H, $NH_2$), 7.90 (d, 1H, J=7.3 Hz, H-6). $^{19}$F NMR (DMSO-$d_6$): δ 2.60 (m). Anal. Calcd for $C_{10}H_{14}FN_3O_4 \cdot 1.4 H_2O$: C, 44.22; H, 5.95; N, 14.77. Found: C, 42.24; H, 5.63; N, 14.54. Compound 4-6 (0.10 g, 0.386 mmol) was converted to the hydrochloride salt by dissolving in water (2 mL) and adjusting the pH to approximately 3.0 with 1 M HCl. The water was removed in vacuo and the residue was crystallized from aqueous EtOH to give 4-6 as the hydrochloride salt (71.0 mg). mp 243° C. (dec); $^1$H NMR (DMSO-$d_6$): δ 1.29 (d, 3H, J=22.6 Hz, $CH_3$), 3.65 (dd, 1H, J=2.3, 12.7 Hz, H-5'), 3.76-3.90 (m, 3H, H-3', H-4', H-5a'), 5.96 (d, 1H, J=17.3 Hz, H-1'), 6.15 (d, 1H, J=7.9 Hz, H-5), 8.33 (d, 1H, J=7.9 Hz, H-6), 8.69 (s, 1.5H, NH), 9.78 (s, 1.5H, NH). $^{19}$F NMR (DMSO-$d_6$): δ 1.69 (m). Anal. Calcd for $C_{10}H_{14}FN_3O_4 \cdot HCl$: C, 40.62; H, 5.11; N, 14.21. Found: C, 40.80; H, 5.09; N, 14.23.

Example 3

Synthesis of (2'R)-6-Chloro-2'-Deoxy-2'-Fluoro-2'-C-Methylpurine Starting from 6-Chloropurine Riboside Scheme 5

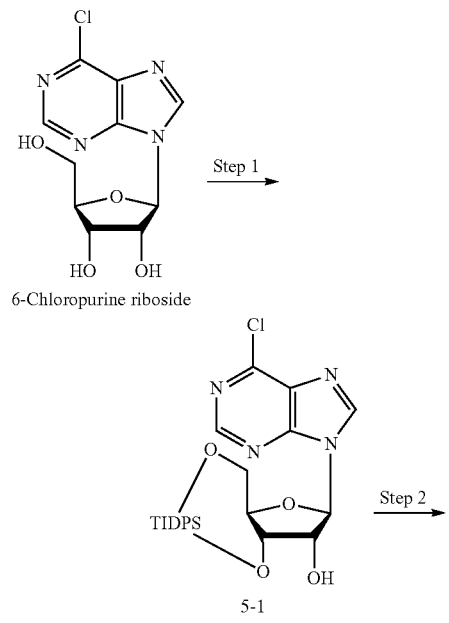

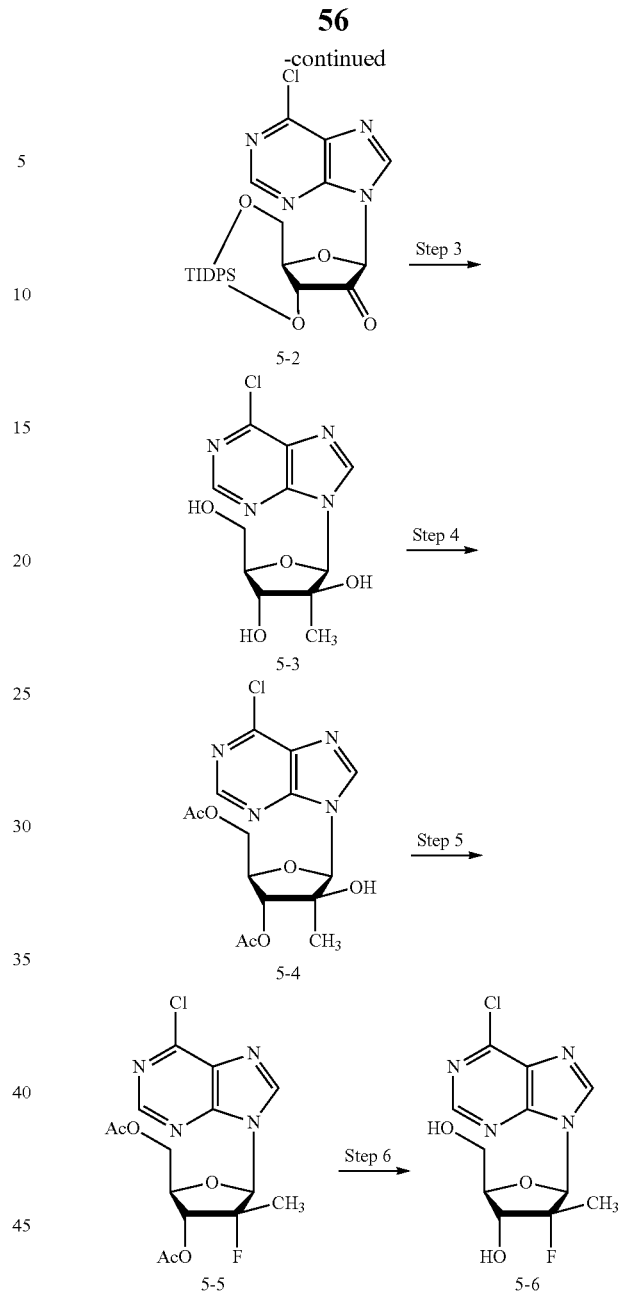

TIDPS = 1,3-(1,1,3,3-Tetraisopropyldisiloxanylidene)

Step 1: The nucleoside, 6-chloropurine riboside, (3.18 g, 11.09 mmol) was dissolved in anhydrous pyridine (300 mL) and was treated dropwise with 1,3-dichloro-1,1,3,3-tetraisopropyl-disiloxane (4.08 mL, 12.75 mmol) at 0° C. under an argon atmosphere. The solution was brought to room temp and stirred overnight. The mixture was concentrated to near dryness in vacuo, dissolved in a minimal amount of chloroform, and washed with HCl (100 mL, 0.05 N) and $NaHCO_3$ (5%, 100 mL). The organic layer was dried ($Na_2SO_4$), filtered, and evaporated to dryness to afford compound 5-1 as an amber glass (6.10 g, >100%) that was used without further purification. $^1$H NMR ($CDCl_3$): δ 1.01-1.13 (m, 24H), 4.03-4.18 (m, 3H), 4.58 (d, 1H, J=5.2 Hz), 5.01 (m, 1H), 6.07 (s, 1H), 8.31 (s, 1H), 8.71 (s, 1H).

Step 2: Compound 5-1 (7.13 g, 13.47 mmol) was dissolved in dry THF (35 mL). Anhydrous DMSO (5.11 mL, 72.06 mmol) was added and the resulting solution was cooled to between −20° C. and −15° C. Trifluoroacetic anhydride (3.06 mL, 21.69 mmol) was added dropwise over 45 minutes and the solution was stirred between −20° C. and −15° C. for 2 hrs after which anhydrous triethylamine (8.08 mL, 57.92 mmol) was added over 20 min. The crude reaction containing ketone 5-2 was dissolved in Et$_2$O (25 mL), and the resulting solution was washed with H$_2$O (2×50 mL), dried (Na$_2$SO$_4$) and the solvents were removed in vacuo to give a yellow solid that was purified on a silica gel column eluting with a stepwise stepwise gradient of 0-50% petroleum ether-diethyl ether afforded compound 5-2 as a mixture with the corresponding geminal diol. The glass was dissolved in CH$_2$Cl$_2$ and stirred over an excess of MgSO$_4$ for 36 h. The mixture, free from the geminal diol, was filtered, and evaporated to dryness to afford compound 5-2 as an amber glass (7.0 g, 97%). $^1$H NMR (CDCl$_3$): δ 1.01-1.13 (m, 24H), 4.09-4.22 (m, 3H), 5.55 (d, 1H, J=9.6 Hz), 5.80 (s, 1H), 8.19 (s, 1H), 8.61 (s, 1H).

Step 3: A solution of compound 5-2 (7.0 g, 13.26 mmol) in anhydrous tetrahydrofuran (45 mL) was cooled to −78° C. with stirring under an argon atmosphere. To the solution was added methylmagnesium bromide (15.85 mL, 3.0 M in ethyl ether) dropwise over a 30 min period. After stirring for an additional 3 h at −78° C., the reaction was quenched by the careful addition of aqueous 1 M NH$_4$Cl (50.0 mL). After warming to room temperature, the mixture was washed with H$_2$O (2×500 mL), dried (Na$_2$SO$_4$), and concentrated to dryness to give a brown foam (3.8 g) that was dissolved in tetrahydrofuran (50 mL) and treated with a solution of TBAF (18.9 mL, 1 M solution in THF) and glacial acetic acid (0.85 mL) at room temp. The solution was stirred at room temp for 2 h, concentrated to dryness, and purified by silica gel chromatography to give compound 5-3 (2.0 g, 50%).

Step 4: Compound 5-3 (0.491 g, 1.63 mmol) was dissolved in pyridine (3 mL) and treated with acetic anhydride (0.38 mL, 4.08 mL) at room temp. The solution was stirred at room temp for 2 h after which time, the solution was concentrated to dryness and treated with diethyl ether (10 mL) and water (5 mL). The organic layer was further washed with water (2×10 mL), dried (Na$_2$SO$_4$), filtered, and evaporated to dryness to give compound 5-4 as a foam (0.450 g, 91.0%). $^1$H NMR (CDCl$_3$): δ 1.39 (s, 3H), 2.15 (s, 3H), 2.21 (s, 3H), 4.27 (m, 1H), 4.49 (dd, 1H, J=4.2, 11.9 Hz), 4.57 (dd, 1H, J=6.16, 11.9 Hz), 5.14 (d, 1H, J=3.1 Hz), 6.25 (s, 1H), 8.54 (s, 1H), 8.75 (s, 1H).

Step 5: Compound 5-4 (0.100 g, 0.259 mmol) was dissolved in anhydrous toluene (3.0 mL) under argon and cooled to −20° C. DAST (0.2 mL, 1.55 mmol) was added slowly and the cooling bath was removed after the addition was complete. Stirring was continued for 1 h and the mixture was poured into satd NaHCO$_3$ (100 mL) and washed until gas evolution ceased. The organic phase was dried (Na$_2$SO$_4$), concentrated, and purified by silica gel chromatography eluting with 30% Et$_2$O-petroleum ether gave pure 5-5 (0.028 g, 27.9%). $^1$H NMR (CDCl$_3$): δ 1.24 (d, 3H, J=22.8 Hz), 2.20 (s, 3H), 2.22 (s, 3H), 4.41-4.55 (m, 3H), 4.47 (dd, 1H, J=9.2, 22.0 Hz), 6.37 (d, 1H, J=17.6 Hz), 8.45 (s, 1H), 8.82 (s, 1H).

Step 6: Compound 5-5 (0.018 g, 0.047 mmol) was dissolved in methanol (5 mL) and treated with a solution of sodium methoxide (3.6 mg, 0.67 mmol) in methanol (5 mL). The solution was stirred at room temp for 1 h, neutralized with concd acetic acid and chromatographed on silica gel eluting with a stepwise gradient of Et$_2$O/methanol (0-5%) to afford compound 5-6 (0.010 g, 70.9%). $^1$H NMR (CDCl$_3$): δ 1.23 (d, 3H, J=22.4 Hz), 4.04 (dd, 1H, J=2.11, 12.5 Hz), 4.17 (dd, 1H, J=1.5, 9.2 Hz,), 4.25 (dd, 1H, J=1.9, 12.3 Hz), 4.61 (dd, 1H, J=9.2, 22.3 Hz), 6.37 (d, 1H, J=17.3 Hz), 8.70 (s, 1H), 8.78 (s, 1H).

Example 4

Synthesis of (2'R)-2'-Deoxy-2'-Fluoro-2'-C-Methyladenosine Starting from (2'R)-6-Chloro-2'-Deoxy-2'-Fluoro-2'-C-Methylpurine

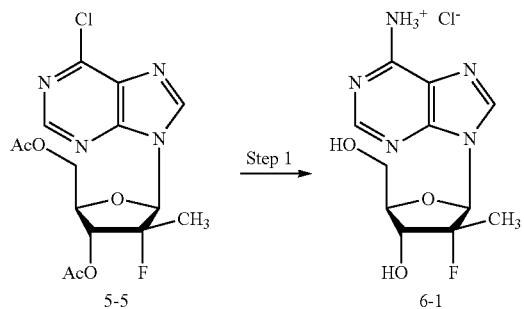

Step 1: Compound 5-5 (0.100 g, 0.26 mmol) was heated in a pressure tube with methanolic ammonia (ca. 7 N, 25 mL) at 80° C. for 12 h. The crude reaction was pre-adsorbed onto silica gel and purified by column chromatography eluting with a stepwise gradient of Et$_2$O-MeOH (0-5%). The impure product was converted to the hydrochloride salt by dissolving the compound in a minimal amount of ethanol and treating the solution with 0.5 mL of a 0.6 M HCl solution. Concentration to near dryness gave compound 6-1 as off-white crystals (0.020 g, 24.2%). NMR (CD$_3$OD): δ 1.19 (d, 3H, J=22.3 Hz), 3.88 (dd, 1H, J=2.7, 12.7 Hz), 4.06 (dd, 1H, J=2.1, 12.5 Hz,), 4.11 (app d, 1H, J=9.2 Hz), 4.35 (dd, 1H, J=9.4, 24.5 Hz), 6.35 (d, 1H, J=16.5 Hz), 8.43 (s, 1H), 8.85 (s, 1H).

Example 5

Antiviral Activity of (2'R)-2'-Deoxy-2'-Fluoro-2'-C-Methylcytidine

HCV Replicon Assay

Figure 1B:
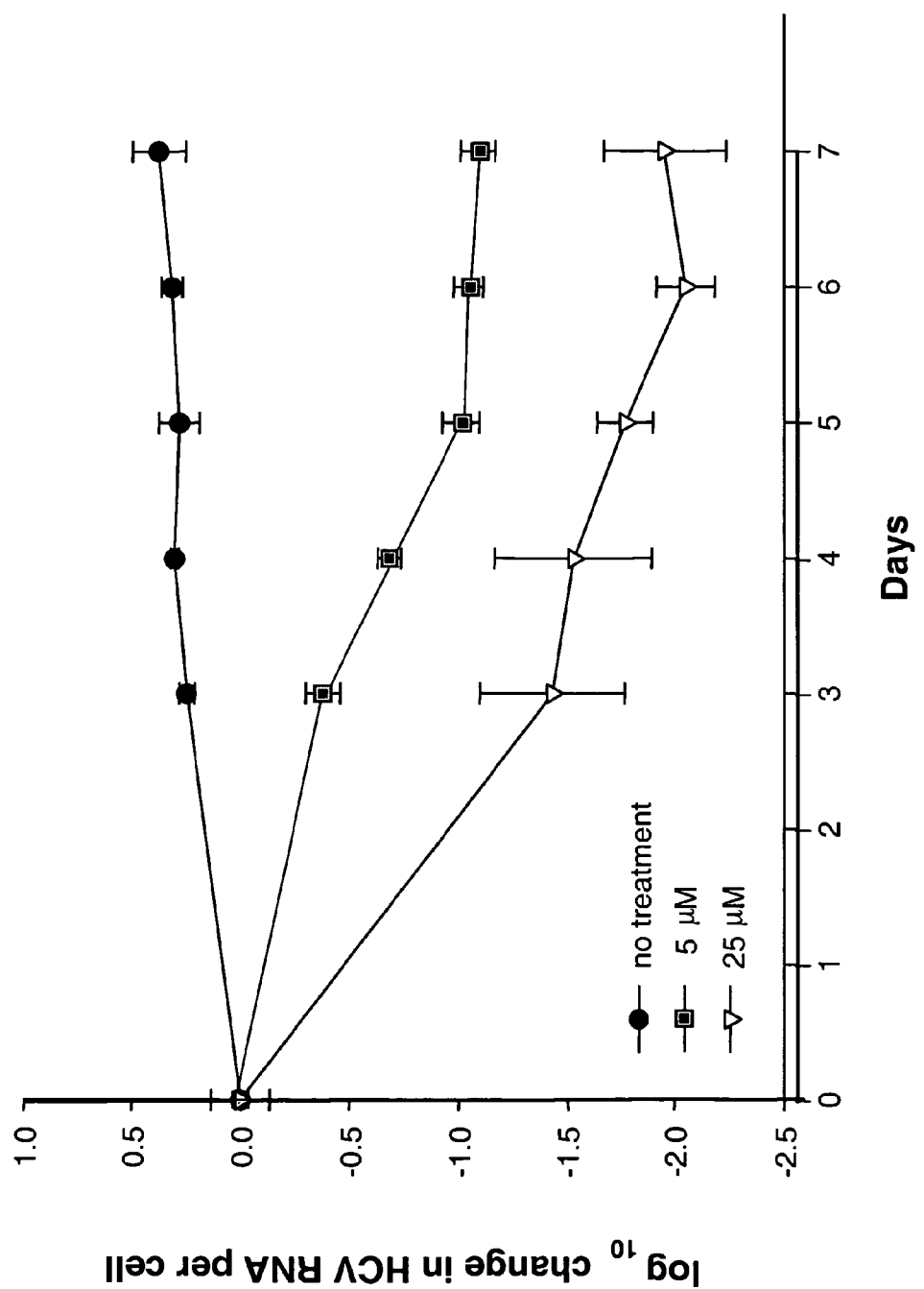

The anti-flavivirus activity of the compounds was determined as described by Stuyver, et al. ("Ribonucleoside analogue that blocks replication of bovine viral diarrhea and hepatitis C viruses in culture", Antimicrobial Agents and Chemotherapy 47:244-254 (2003)). The compound was dissolved in DMSO and added to the culture media at final concentrations ranging from 3 to 100 μM. A 4-days incubation resulted in dose-dependant reduction of the replicon HCV RNA (FIG. 1A). A 1-log reduction of replicon RNA (or EC$_{90}$ value) was reached at approximately 2.5 μM. Measurement of the reduction of rRNA gave an indication of the inhibitory effect on cellular polymerases. Subtraction of this cellular toxicity value from the antiviral values resulted in the therapeutic index line and EC$_{90}$ value. Based on these calculations, an average EC90 value, corrected for cellular toxicity, of approximately 2.5 was obtained. FIG. 1A shows the dose-dependant reduction of the replicon HCV RNA based on the treatment with (2'R)-2'-deoxy-2'-fluoro-2'-C-methylcytidine. The viral reduction was compared to the reduction of cellular RNA levels (ribosomal RNA) to obtain therapeutic index values. EC$_{90}$ represents the effective concentration 90% at 96 hours following the dose dependant administration of (2'R)-2'-deoxy-2'-fluoro-2'-C-methylcytidine. FIG. 1B shows the prolonged reduction in replicon HCV RNA up to 7 days following treatment with 5 and 25

The activity of (2'R)-2'-deoxy-2'-fluoro-2'-C-methylcytidine in the replicon system is summarized in Table 1. The EC$_{90}$ values for (2'R)-2'-deoxy-2'-fluoro-2'-C-methylcytidine as well as 2'-C-methylcytidine and 2'-C-methyladenosine are shown for three separate replicon clones (HCV-WT (Wild Type), 9-13 and 21-5) as well as two other clones (S282T and rRNA). The EC$_{90}$ values for (2'R)-2'-deoxy-2'-fluoro-2'-C-methylcytidine were in the range of 1.6 to 4.6 μM for the replicon clones. In contrast the EC$_{90}$ values for 2'-C-methylcytidine were in the range of 6.6-37.4 μM. Interestingly, the EC$_{90}$ values for 2'-C-methyladenosine were comparable to those of (2'R)-2'-deoxy-2'-fluoro-2'-C-methylcytidine. The activity of (2'R)-2'-deoxy-2'-fluoro-2'-C-methylcytidine and 2'-C-methylcytidine in other replicons tested is shown in Table 2.

Polymerase Assay

Table 3 shows the potency of (2'R)-2'-deoxy-2'-fluoro-2'-C-methylcytidine-5'-triphosphate (TP) in the NS5B polymerase assay. The inhibitory concentration 50% was determined to be in the range of 1.7 to 7.7 μM.

Toxicity

A summary of the toxicity data for (2'R)-2'-deoxy-2'-fluoro-2'-C-methylcytidine using the mitochondrial toxicity assay is shown in Tables 6 and 7. Table 7 shows the lack of effects of (2'R)-2'-deoxy-2'-fluoro-2'-C-methylcytidine and 2'-C-methylcytidine on mitochondrial DNA synthesis and lack of effects on lactic acid increase in this assay. Results shows the relative lack of toxicity of (2'R)-2'-deoxy-2'-fluoro-2'-C-methylcytidine. Table 6 shows a cytotoxicity analysis in various cell lines (Clone A, Huh7, HepG2, MDBK, PBM, CEM, Vero, MRC-5). Cytotoxic concentration 50% (CC$_{50}$) was greater than 75-100 μM in all clones tested for (2'R)-2'-deoxy-2'-fluoro-2'-C-methylcytidine as well as 2'-C-methylcytidine. In contrast is the relative toxicity of 2'-C-methyladenosine.

The effects the nucleoside analogs tested on human bone marrow cells is depicted in Table 9. As shown, the IC$_{50}$ values for 2'-methyl-2'-fluorocytidine were significantly higher (98.2, BFU-E) and 93.9 (CFU-GM) as compared to 2'-methylcytadine or AZT. Results show that 2'-methyl-2'-fluorocytidine was significantly less toxic than compared to the other nucleoside compounds.

Animal Studies

Figure 2:
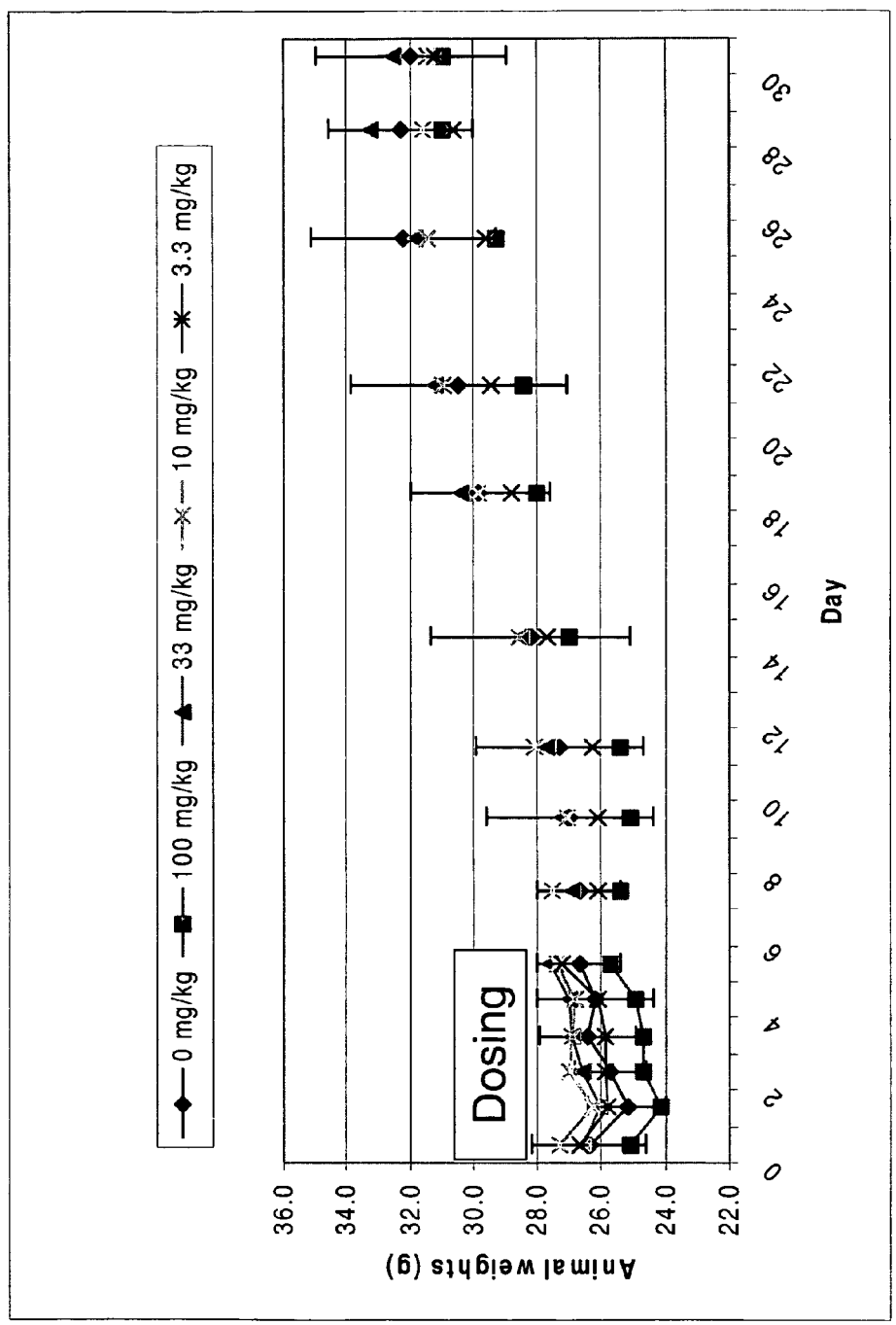
FIG. 2 depicts the average weight change (%) of female Swiss mice in the toxicity study of β-D-(2'R)-2'-deoxy-2'-fluoro-2'-C-methylcytidine at various doses. Intraperitoneal injections were given on days 0 to day 5 of the 0, 3.3, 10, 33, 100 mg/kg. Each dosing group contained 5 mice and no mice died during the 30-day study.

FIG. 2 depicts the average weight change (%) of female Swiss mice in vivo the toxicity analysis of (2'R)-2'-deoxy-2'-fluoro-2'-C-methylcytidine at various doses. Intraperitoneal injections were given on days 0 to day 5 of the 0, 3.3, 10, 33, 100 mg/kg. Each dosing group contained 5 mice and no mice died during the 30-day study. No significant toxicity was observed in the mice.

Figure 3:
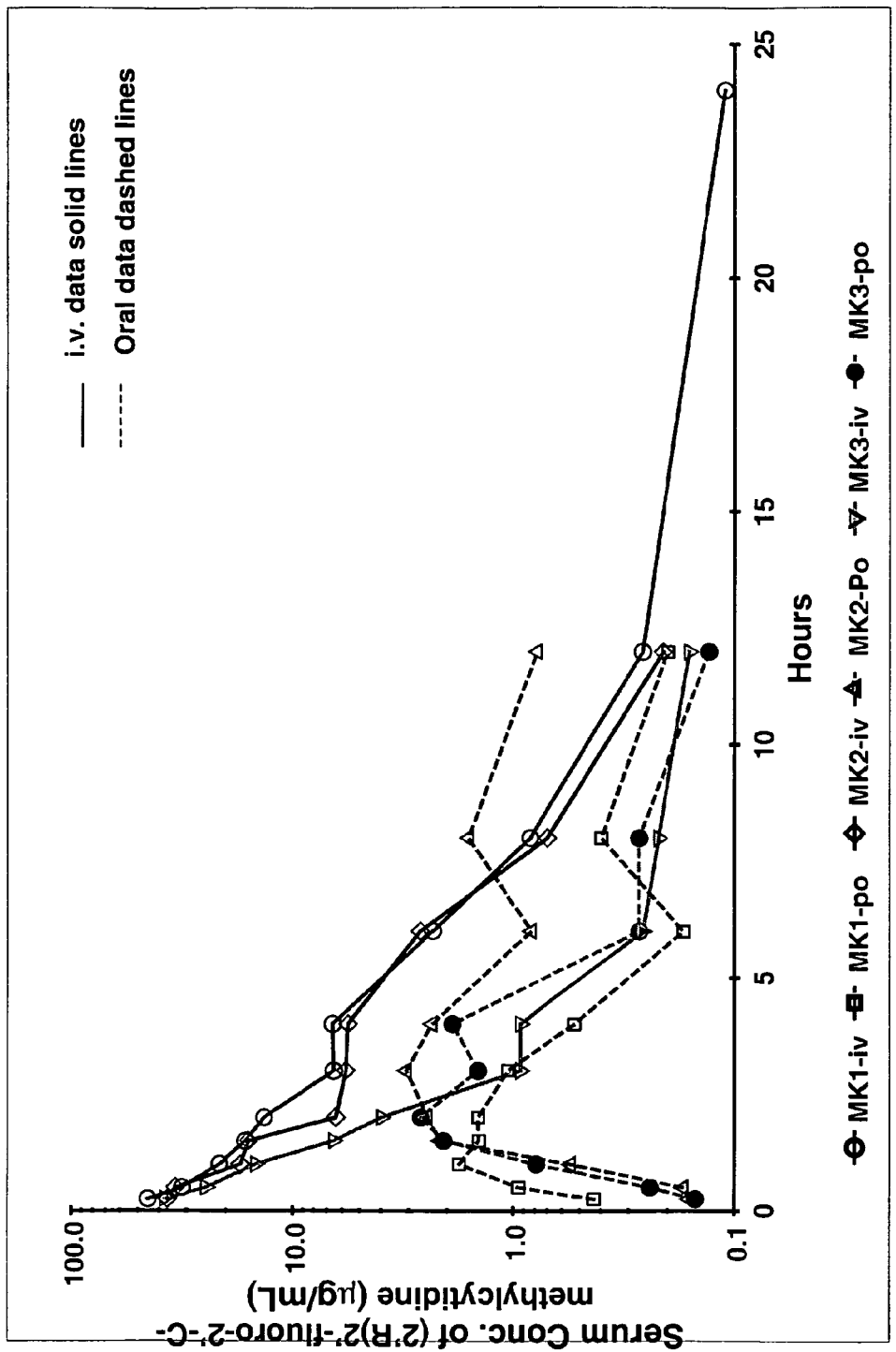
FIG. 3 depicts the pharmacokinetics of β-D-(2'R)-2'-deoxy-2'-fluoro-2'-C-methylcytidine in Rhesus monkeys given a single dose (33.3 mg/kg) oral or intravenous dose of β-D-(2'R)-2'-deoxy-2'-fluoro-2'-C-methylcytidine.

FIG. 3 and Table 6 summarize the pharmacokinetic parameters of (2'R)-2'-deoxy-2'-fluoro-2'-C-methylcytidine in Rhesus monkeys given a single dose (33.3 mg/kg) oral (Table 6, FIG. 3) or intravenous dose (FIG. 3) of (2'R)-2'-deoxy-2'-fluoro-2'-C-methylcytidine.

Other Antiviral Activity

Summary of the range of antiviral activity of (2'R)-2'-deoxy-2'-fluoro-2'-C-methylcytidine is shown in Table 4. Table shows that in addition to HCV virus (2'R)-2'-deoxy-2'-fluoro-2'-C-methylcytidine shows activity against Rhinovirus, West Nile virus, Yellow Fever virus, and Dengue virus.

Table 5 shows the lack of activity of (2'R)-2'-deoxy-2'-fluoro-2'-C-methylcytidine on HCV surrogate models BVDV as well as other viruses including HIV, HBV and Corona virus. In contrast, 2'-C-methylcytidine and 2'-C-methyladenosine show greater activity in the HCV surrogate model, BVDV. These results show the necessity for screening this series of compounds against the HCV replicon system versus surrogate HCV systems.

TABLE 1

Summary of the Anti-HCV Replicon Activity of (2'R)-2'-deoxy-2'-fluoro-2'-C-methylcytidine*

| Replicon | (2'R)-2'-deoxy-2'-fluoro-2'-C-methylcytidine | 2'-C-methylcytidine | 2'-C-methyladenosine |
| --- | --- | --- | --- |
| HCV-WT 1b | 4.6 ± 2.0 | 21.9 ± 4.3 | 2.1 ± 0.27 |
| S282T mut. 1b | 30.7 ± 11.7 | 37.4 ± 12.1 | >100 |
| 9-13 (subgenomic) | 4.6 ± 2.3 | 13.0 | 0.7 |
| 21-5 (full-length) | 1.6 ± 0.7 | 6.6 | 0.6 |

*Values represent EC$_{90}$ (μM)

TABLE 2

Activity of (2'R)-2'-deoxy-2'-fluoro-2'-C-methylcytidine and 2'-C-methylcytidine in other Replicons

| | (2'R)-2'-deoxy-2'-fluoro-2'-C-methylcytidine | | | 2'-C-methylcytidine | | |
| --- | --- | --- | --- | --- | --- | --- |
| | | IC$_{90}$ (μM) | | | IC$_{90}$ (μM) | |
| | EC$_{90}$ | | | EC$_{90}$ | | |
| Replicon | (μM) | GAPDH | MTT | (μM) | GAPDH | MTT |
| 1b (Ntat) | 3.8 | >100 | >100 | 27.2 | >100 | >100 |
| 1b (Btat) | 11.5 | >100 | >100 | 31.1 | >100 | >100 |
| 1a (pp1aSI-7) | 34.7 | >100 | >100 | 35.0 | >100 | >100 |

TABLE 3

HCV 1b NS5B Polymerase Assay (IC$_{50}$, μM)

| | (2'R)-2'-deoxy-2'-fluoro-2'-C-methylcytidine TP | 2'-C-methylcytidine TP | 2'-C-methyladenosine TP |
| --- | --- | --- | --- |
| Wild-Type NS5B | 1.7 ± 0.4$^a$ 7.7 ± 1.2$^b$ | 6.0 ± 0.5 | 20.6 ± 5.2 |
| S282T | 2.0$^a$ 8.3 ± 2.4$^c$ | 26.9 ± 5.5 | >100 |

$^a$Values determined using batch 1;
$^b$Value determined using batch 2 and 3; and
$^c$Value determined using batch 2.

TABLE 4

Summary of Antiviral Activity of (2'R)-2'-deoxy-2'-fluoro-2'-C-methylcytidine

| Virus | Cell | EC$_{50}$, CPE (μM) | EC$_{50}$, NR$^a$ (μM) | CC$_{50}$, CPE (μM) | CC$_{50}$, NR$^a$ (μM) |
| --- | --- | --- | --- | --- | --- |
| West Nile | Vero | 32 | 12 | >100 | 32 |
| Dengue Type 2 | Vero | 32/55 | >100/>100 | >100 | >100 |

TABLE 4-continued

Summary of Antiviral Activity of
(2'R)-2'-deoxy-2'-fluoro-2'-C-methylcytidine

| Virus | Cell | $EC_{50}$, CPE (μM) | $EC_{50}$, $NR^a$ (μM) | $CC_{50}$, CPE (μM) | $CC_{50}$, $NR^a$ (μM) |
|---|---|---|---|---|---|
| Yellow Fever | Vero | 19/3.2 | 32/12 | >100 | >100 |
| Influenza A (H1N1) | MDCK | >100 | >100 | >100 | >100 |
| Influenza A (H3N2) | MDCK | >100 | >100 | >100 | >100 |
| Influenza B | MDCK | >100 | >100 | >100 | >100 |
| Rhinovirus Type 2 | KB | 25 | 20 | >100 | >100 |
| VEE | Vero | >100 | >100 | >100 | >100 |
| SARSCoV | Vero | >100 | >100 | >100 | >100 |

$^a$NR = Neutral Red.

TABLE 5

Summary of Antiviral Activity of
(2'R)-2'-deoxy-2'-fluoro-2'-C-methylcytidine

| Virus | (2'R)-2'-deoxy-2'-fluoro-2'-C-methylcytidine ($EC_{90}$, μM) | 2'-C-methylcytidine ($EC_{90}$, μM) | 2'-C-methyladenosine ($EC_{90}$, μM) |
|---|---|---|---|
| BVDVncp | >22 | 0.5 | 1.2 |
| BVDVcp | >100 | 2 | 1.5 |
| RSV | >100 | >100 | >100 |
| $HIV^a$ | >100 | ND | ND |
| HBV | >10 | >10 | ND |
| Coronavirus 229E | >100 | ND | ND |

ND = Not determined.

TABLE 6

Cytotoxicity Studies$^a$

| Cell Line | (2'R)-2'-deoxy-2'-fluoro-2'-C-methylcytidine $CC_{50}$, μM | 2'-C-methylcytidine $CC_{50}$, μM | 2'-C-methyladenosine $CC_{50}$, μM |
|---|---|---|---|
| CloneA | >100 | >100 | 37 |
| Huh7 | >100 | >100 | 30 |
| HepG2 | 75 | >100 | 58 |
| MDBK | >100 | >100 | |
| PBM | >100 | | |
| CEM | >100 | | |
| Vero | >100 | | |
| MRC-5 | >100 | | |

$^a$Results determined using MTS assay.

TABLE 7

Mitochondrial Toxicity Study

| Compound | mtDNA Synthesis ($IC_{50}$, μM) | Lactic Acid Increase |
|---|---|---|
| (2'R)-2'-deoxy-2'-fluoro-2'-C-methylcytidine | >25 | No effect ≧33 μM |
| 2'-C-methylcytidine | >25 | No effect ≧33 μM |

TABLE 8

Preliminary PK Parameters in Rhesus Monkeys Following
a Single Oral Dose of
(2'R)-2'-deoxy-2'-fluoro-2'-C-methylcytidine at 33.3 mg/kg

| Parameter | Units | Mean ± SD |
|---|---|---|
| $C_{max}$ | μM | 9.6 ± 2.7 |
| $T_{max}$ | hours | 2 ± 1 |
| $AUC_{0-last}$ | μM × h | 44.2 ± 22.2 |
| $T^{1/2}$ | hours | 3.9 ± 0.1 |
| Bioavailability | F. % | 21 ± 11 |

TABLE 9

Effect of Nucleoside Analogs on Human Bone Marrow Cells

| Compound (β-D-analog) | BFU-E $IC_{50}$ (μM) | CFU-GM $IC_{50}$ (μM) |
|---|---|---|
| 2'-fluoro-2'-C-methylcytidine | 98.2 | 93.9 |
| 2'-C-methylcytidine | 20.1 | 13.2 |
| AZT | 0.08 | 0.95 |

The invention claimed is:

1. A method of inhibiting the proliferation of hepatitis C virus in a human subject infected with the virus comprising providing to the subject an antivirally effective amount of a compound of the structure:

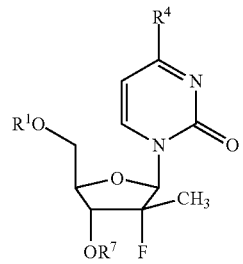

or its pharmaceutically acceptable salt
wherein $R^1$ and $R^7$ are both H;
and
$R^4$ is $NH_2$.

2. A method of inhibiting the proliferation of a hepatitis C virus in a human subject infected with the virus comprising providing to the subject an antivirally effective amount of a compound of the structure:

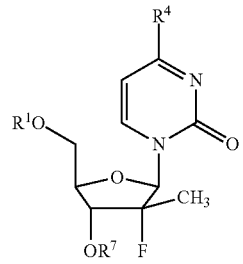

or its pharmaceutically acceptable salt
wherein $R^1$ is monophosphate; $R^7$ is H; and $R^4$ is $NH_2$.

3. A method of inhibiting the proliferation of hepatitis C virus in a human subject infected with the virus comprising providing to the subject an antivirally effective amount of a compound of the structure:

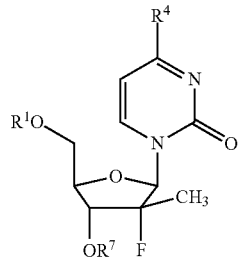

or its pharmaceutically acceptable salt wherein $R^1$ is diphosphate; $R^7$ is H; and $R^4$ is $NH_2$.

4. A method of inhibiting the proliferation of hepatitis C virus in a human subject infected with the virus comprising providing to the subject an antivirally effective amount of a compound of the structure:

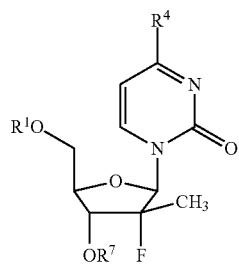

or its pharmaceutically acceptable salt wherein $R^1$ is triphosphate; $R^7$ is H; and $R^4$ is $NH_2$.

5. A method of inhibiting the proliferation of hepatitis C virus in a human subject infected with the virus comprising providing to the subject an antivirally effective amount of a compound of the structure:

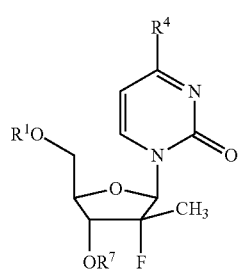

or its pharmaceutically acceptable salt wherein $R^1$ is an H-phosphonate; $R^7$ is H; and $R^4$ is $NH_2$.

6. A method of inhibiting the proliferation of hepatitis C virus in a human subject infected with the virus comprising providing to the subject an antivirally effective amount of a compound of the structure:

or its pharmaceutically acceptable salt wherein $R^1$ and $R^7$ are both H; and $R^4$ is OH.

7. A method of inhibiting the proliferation of hepatitis C virus in a human subject infected with the virus comprising providing to the subject an antivirally effective amount of a compound of the structure:

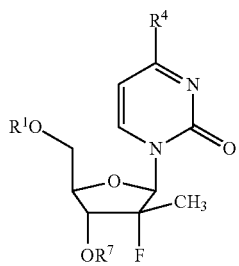

or its pharmaceutically acceptable salt wherein $R^1$ is monophosphate; $R^7$ is H; and $R^4$ is OH.

8. A method of inhibiting the proliferation of hepatitis C virus in a human subject infected with the virus comprising providing to the subject an antivirally effective amount of a compound of the structure:

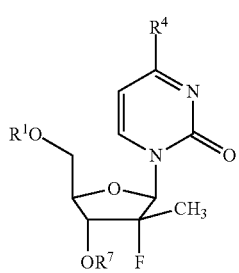

or its pharmaceutically acceptable salt wherein $R^1$ is diphosphate; $R^7$ is H; and $R^4$ is OH.

9. A method of inhibiting the proliferation of hepatitis C virus in a human subject infected with the virus comprising providing to the subject an antivirally effective amount of a compound of the structure:

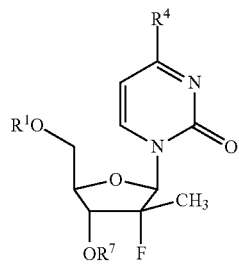

or its pharmaceutically acceptable salt
wherein $R^1$ is triphosphate; $R^7$ is H; and $R^4$ is OH.

10. A method of inhibiting the proliferation of hepatitis C virus in a human subject infected with the virus comprising providing to the subject an antivirally effective amount of a compound of the structure:

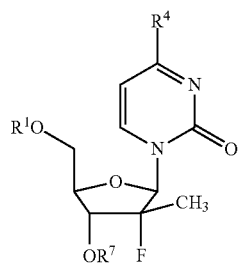

or its pharmaceutically acceptable salt
wherein $R^1$ is an H-phosphonate; $R^7$ is H; and $R^4$ is OH.

11. A method for the treatment of a hepatitis C infection, comprising:
providing to a human in need thereof an antivirally effective amount of a compound of the structure:

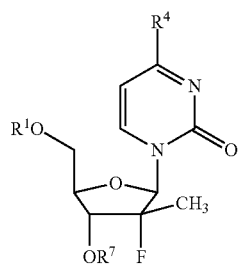

or its pharmaceutically acceptable salt
wherein $R^1$ and $R^7$ are both H; and
$R^4$ is $NH_2$.

12. A method for the treatment of a hepatitis C infection, comprising:
providing to a human in need thereof an antivirally effective amount of a compound of the structure:

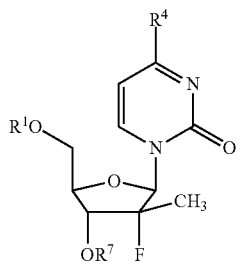

or its pharmaceutically acceptable salt
wherein
$R^1$ is monophosphate and $R^7$ is H; and
$R^4$ is $NH_2$.

13. A method for the treatment of a hepatitis C infection, comprising:
providing to a human in need thereof an antivirally effective amount of a compound of the structure:

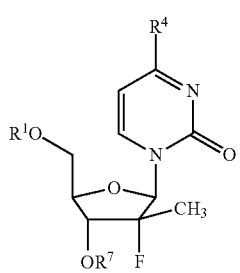

or its pharmaceutically acceptable salt
wherein $R^1$ is diphosphate and $R^7$ is H; and
$R^4$ is $NH_2$.

14. A method for the treatment of a hepatitis C infection, comprising:
providing to a human in need thereof an antivirally effective amount of a compound of the structure:

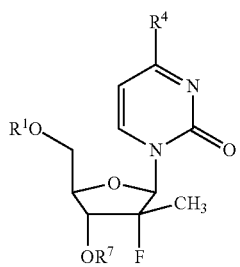

or its pharmaceutically acceptable salt
wherein $R^1$ is triphosphate and $R^7$ is H; and
$R^4$ is $NH_2$.

15. A method for the treatment of a hepatitis C infection, comprising:
providing to a human in need thereof an antivirally effective amount of a compound of the structure:

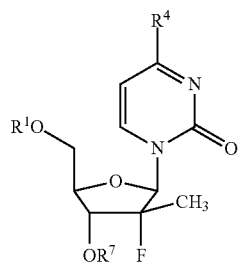

or its pharmaceutically acceptable salt
wherein $R^1$ is H-phosphonate and $R^7$ is H; and
$R^4$ is $NH_2$.

16. A method for the treatment of a hepatitis C infection, comprising:
providing to a human in need thereof an antivirally effective amount of a compound of the structure:

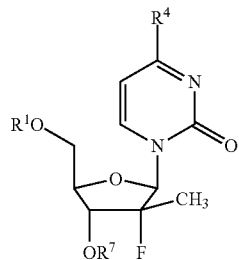

or its pharmaceutically acceptable salt
wherein $R^1$ and $R^7$ are both H; and
$R^4$ is OH.

17. A method for the treatment of a hepatitis C infection, comprising:
providing to a human in need thereof an antivirally effective amount of a compound of the structure:

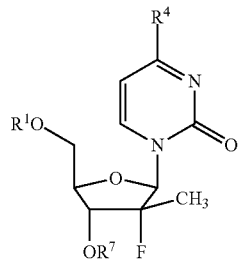

or its pharmaceutically acceptable salt
wherein $R^1$ is monophosphate and $R^7$ is H; and
$R^4$ is OH.

18. A method for the treatment of a hepatitis C infection, comprising:
providing to a human in need thereof an antivirally effective amount of a compound of the structure:

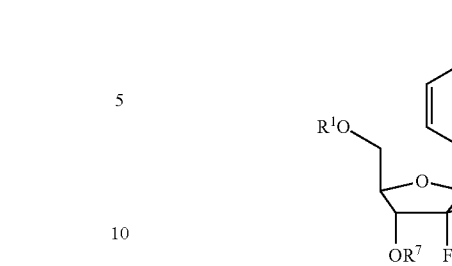

or its pharmaceutically acceptable salt
wherein $R^1$ is diphosphate and $R^7$ is H; and
$R^4$ is OH.

19. A method for the treatment of a hepatitis C infection, comprising:
providing to a human in need thereof an antivirally effective amount of a compound or its-pharmaceutically acceptable salt of the structure:

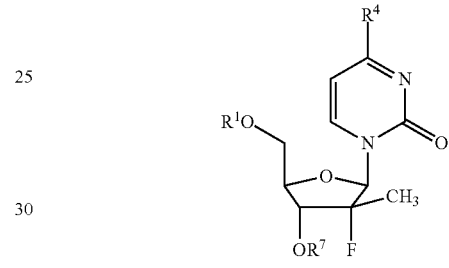

or its pharmaceutically acceptable salt
wherein $R^1$ is triphosphate and $R^7$ is H; and
$R^4$ is OH.

20. A method for the treatment of a hepatitis C infection, comprising:
providing to a human in need thereof an antivirally effective amount of a compound of the structure:

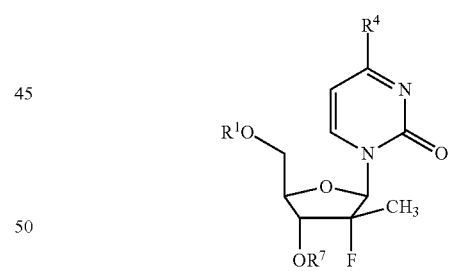

or its pharmaceutically acceptable salt
wherein $R^1$ is H-phosphonate and $R^7$ is H; and
$R^4$ is OH.

21. A method as recited in any one of the preceding claims, wherein the antivirally effective amount of the compound is administered in combination or alternation with at least one treatment selected from the group consisting of an antiviral treatment, an antibacterial treatment, an anticancer treatment, and interferon.

* * * * *